US012729385B2

(12) United States Patent
Dai et al.

(10) Patent No.: US 12,729,385 B2
(45) Date of Patent: Sep. 8, 2026

(54) RECOMBINANT ADENO-ASSOCIATED VIRUS COMPOSITIONS AND METHODS FOR PRODUCING SAME

(71) Applicant: Prevail Therapeutics, Inc., New York, NY (US)

(72) Inventors: Yong Dai, Northborough, MA (US); Jingmin Zhou, Wallingford, PA (US); Garrett Daniels, Croton on Hudson, NY (US); Jonathan Chan, Jersey City, NJ (US); Jorge Haller, Tarrytown, NY (US); Stuart Nelson, New York, NY (US)

(73) Assignee: PREVAIL THERAPEUTICS, INC., New York, NY (US)

( * ) Notice: Subject to any disclaimer, the term of this patent is extended or adjusted under 35 U.S.C. 154(b) by 478 days.

(21) Appl. No.: 17/502,979

(22) Filed: Oct. 15, 2021

(65) Prior Publication Data

US 2022/0119843 A1 Apr. 21, 2022

Related U.S. Application Data

(60) Provisional application No. 63/092,179, filed on Oct. 15, 2020.

(51) Int. Cl.

| | |
|---|---|
| ***C12N 15/86*** | (2006.01) |
| ***A61K 38/47*** | (2006.01) |
| ***C12N 5/07*** | (2010.01) |
| ***C12N 7/00*** | (2006.01) |
| ***C12N 9/24*** | (2006.01) |

(52) U.S. Cl.

CPC .............. *C12N 15/86* (2013.01); *A61K 38/47* (2013.01); *C12N 5/0601* (2013.01); *C12N 7/00* (2013.01); *C12N 9/2402* (2013.01); *C12Y 302/01045* (2013.01); *C12N 2710/14043* (2013.01); *C12N 2750/14143* (2013.01); *C12N 2750/14151* (2013.01)

(58) Field of Classification Search

CPC ..................... C12N 15/86; C12N 7/00; C12N 2710/14043; C12N 2750/14143; C12N 2710/14143; C12N 2750/14141; C12N 2750/14152

See application file for complete search history.

(56) References Cited

U.S. PATENT DOCUMENTS

| | | | | |
|---|---|---|---|---|
| 8,945,918 | B2 | 2/2015 | Chen | |
| 10,689,625 | B2 | 6/2020 | Abeliovich et al. | |
| 10,837,028 | B2 | 11/2020 | Abeliovich et al. | |
| 11,060,113 | B2 | 7/2021 | Abeliovich et al. | |
| 11,414,676 | B2 | 8/2022 | Chen | |
| 11,655,460 | B2 | 5/2023 | Abeliovich et al. | |
| 11,661,585 | B2 | 5/2023 | Abeliovich et al. | |
| 11,802,294 | B2 * | 10/2023 | Abeliovich | C07K 14/435 |
| 11,807,849 | B2 | 11/2023 | Abeliovich et al. | |
| 11,903,985 | B2 | 2/2024 | Abeliovich et al. | |
| 2018/0155697 | A1 | 6/2018 | Wu et al. | |
| 2019/0002842 | A1 * | 1/2019 | Lock | C12N 7/02 |
| 2020/0231954 | A1 | 7/2020 | Abeliovich et al. | |
| 2020/0231970 | A1 | 7/2020 | Abeliovich et al. | |
| 2020/0276335 | A1 | 9/2020 | Abeliovich et al. | |
| 2020/0282080 | A1 | 9/2020 | Abeliovich et al. | |
| 2020/0308554 | A1 | 10/2020 | Abeliovich et al. | |
| 2020/0316221 | A1 | 10/2020 | Gao et al. | |
| 2020/0318115 | A1 | 10/2020 | Abeliovich et al. | |
| 2020/0332265 | A1 | 10/2020 | Abeliovich et al. | |
| 2020/0338148 | A1 | 10/2020 | Abeliovich et al. | |
| 2021/0317474 | A1 * | 10/2021 | Kaspar | A61K 9/0019 |
| 2021/0332385 | A1 | 10/2021 | Abeliovich et al. | |
| 2023/0287358 | A1 | 9/2023 | Abeliovich | |
| 2023/0310654 | A1 | 10/2023 | Abeliovich et al. | |
| 2023/0346979 | A1 | 11/2023 | Abeliovich et al. | |
| 2024/0123003 | A1 | 4/2024 | Abeliovich et al. | |

FOREIGN PATENT DOCUMENTS

| | | | | |
|---|---|---|---|---|
| WO | WO 2007/084773 | A2 | 7/2007 | |
| WO | WO-2011094198 | A1 * | 4/2011 | C12N 15/86 |
| WO | WO-2019084068 | A1 | 5/2019 | |

OTHER PUBLICATIONS

Zolotukhin, S., Byrne, B., Mason, E. et al. Recombinant adeno-associated virus purification using novel methods improves infectious titer and yield. Gene Ther 6, 973-985 (Year: 1999).*

Robert M. Kotin, Large-scale recombinant adeno-associated virus production, Human Molecular Genetics, vol. 20, Issue R1, pp. R2-R6 (Year: 2011).*

Mahley RW, Weisgraber KH, Huang Y. Apolipoprotein E: structure determines function, from atherosclerosis to Alzheimer's disease to AIDS. J Lipid Res. Suppl(Suppl):S183-8. (Year: 2009).*

Dawson TM, Dawson VL. The role of parkin in familial and sporadic Parkinson's disease. Mov Disord. Suppl 1(01):S32-9. (Year: 2010).*

Dept. of Health, Education, and Welfare Public Health Service, Food and Drug Admin. Inspection Technical Guide, Ch. 40 "Bacterial Endotoxins/Pyrogens" Published Mar. 20, 1985, Updated Nov. 17, 2014 (Year: 2014).*

Continuation of Reference U: Website URL <https://www.fda.gov/inspections-compliance-enforcement-and-criminal-investigations/inspection-technical-guides/bacterial-endotoxinspyrogens> (Year: 2014).*

Geisler, Christoph, and Donald L. Jarvis. "Adventitious viruses in insect cell lines used for recombinant protein expression." Protein expression and purification 144 (2018): 25-32. (Year: 2018).*

(Continued)

*Primary Examiner* — Teresa E Knight
*Assistant Examiner* — Michael Angelo Riga
(74) *Attorney, Agent, or Firm* — Brian C. Cholewa

(57) ABSTRACT

Disclosed herein are compositions comprising recombinant adeno-associated virus (rAAV), as well as recombinant baculovirus systems and methods of using the same for producing and purifying such compositions. Also disclosed herein are assays for testing the titer and potency of such compositions.

22 Claims, 3 Drawing Sheets

Specification includes a Sequence Listing.

(56) References Cited

OTHER PUBLICATIONS

Kondratov, Oleksandr, et al. "Direct head-to-head evaluation of recombinant adeno-associated viral vectors manufactured in human versus insect cells." Molecular Therapy 25.12 (2017): 2661-2675. (Year: 2017).*

International Search Report and Written Opinion for International Application No. PCT/US2021/055243, mailed Sep. 1, 2022, 21 pages.

Tomono et al., "Ultracentrifugation-free chromatography-mediated large-scale purification of recombinant adeno-associated virus serotype 1 (rAAV1)," Molecular Therapy—Methods & Clinical Development, 2016, 3(15058):1-8.

Chen, "Intron Splicing-mediated Expression of AAV Rep and Cap Genes and Production of AAV Vectors in Insect Cells," Molecular Therapy, May 2008, 16(5):924-930.

Liu, et al., "Using a fed-batch culture strategy to enhance rAAV production in the baculovirus/insect cell system," Journal of Bioscience and Bioengineering, 2010, 110(2):187-193.

Wu, et al., "A Recombinant Baculovirus Efficiently Generates Recombinant Adeno-Associated Virus Vectors in Cultured Insect Cells and Larvae," Molecular Therapy: Methods & Clinical Development, Sep. 2018, 10:38-47.

Smith, R. et al., "A Simplified Baculovirus-AAV Expression Vector System Coupled With One-step Affinity Purification Yields High-titer rAAV Stocks From Insect Cells," Mol Ther., Nov. 2009, 17(11):1888-1896.

Urabe, M. et al., "Insect Cells as a Factory to Produce Adeno-Associated Virus Type 2 Vectors," Human Gene Therapy, Nov. 1, 2002, 13:1935-1943.

* cited by examiner

FIG. 1

| | Replicates 1-4 | | | | Replicates 1-4 | | | | Replicates 1-4 | | | |
|---|---|---|---|---|---|---|---|---|---|---|---|---|
| | 1 | 2 | 3 | 4 | 5 | 6 | 7 | 8 | 9 | 10 | 11 | 12 |
| A | RS dilution 1 | RS dilution 1 | RS dilution 1 | RS dilution 1 | TS 1 dilution 1 | TS 1 dilution 1 | TS 1 dilution 1 | TS 1 dilution 1 | TS 2 dilution 1 | TS 2 dilution 1 | TS 2 dilution 1 | TS 2 dilution 1 |
| B | RS dilution 2 | RS dilution 2 | RS dilution 2 | RS dilution 2 | TS 1 dilution 2 | TS 1 dilution 2 | TS 1 dilution 2 | TS 1 dilution 2 | TS 2 dilution 2 | TS 2 dilution 2 | TS 2 dilution 2 | TS 2 dilution 2 |
| C | RS dilution 3 | RS dilution 3 | RS dilution 3 | RS dilution 3 | TS 1 dilution 3 | TS 1 dilution 3 | TS 1 dilution 3 | TS 1 dilution 3 | TS 2 dilution 3 | TS 2 dilution 3 | TS 2 dilution 3 | TS 2 dilution 3 |
| D | RS dilution 4 | RS dilution 4 | RS dilution 4 | RS dilution 4 | TS 1 dilution 4 | TS 1 dilution 4 | TS 1 dilution 4 | TS 1 dilution 4 | TS 2 dilution 4 | TS 2 dilution 4 | TS 2 dilution 4 | TS 2 dilution 4 |
| E | RS dilution 5 | RS dilution 5 | RS dilution 5 | RS dilution 5 | TS 1 dilution 5 | TS 1 dilution 5 | TS 1 dilution 5 | TS 1 dilution 5 | TS 2 dilution 5 | TS 2 dilution 5 | TS 2 dilution 5 | TS 2 dilution 5 |
| F | RS dilution 6 | RS dilution 6 | RS dilution 6 | RS dilution 6 | TS 1 dilution 6 | TS 1 dilution 6 | TS 1 dilution 6 | TS 1 dilution 6 | TS 2 dilution 6 | TS 2 dilution 6 | TS 2 dilution 6 | TS 2 dilution 6 |
| G | FB | FB | FB | FB | FB | FB | FB | FB | FB | FB | FB | FB |
| H | Blank | Blank | Blank | Blank | Blank | Blank | Blank | Blank | Blank | Blank | Blank | Blank |

| ID | Relative Potency |
| --- | --- |
| Sample 1 | <0.37 |
| Sample 2 | 2.53 |
| Sample 3 | 0.74 |
| Sample 4 | 3.96 |
| Sample 5 | 1.00 |

| Sample | Relative Potency (to TOX lot) |
| --- | --- |
| Sample 1 | 626% |
| Sample 2 | 474% |
| Sample 3 | 131% |

SEQUENCE LISTING

<160> NUMBER OF SEQ ID NOS: 12

<210> SEQ ID NO 1
<211> LENGTH: 536
<212> TYPE: PRT
<213> ORGANISM: Homo sapiens

<400> SEQUENCE: 1

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln

-continued

```
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510
```

```
Asp Pro Ala Val Gly Phe Leu Glu Thr Ile Ser Pro Gly Tyr Ser Ile
        515                 520                 525

His Thr Tyr Leu Trp Arg Arg Gln
    530                 535


<210> SEQ ID NO 2
<211> LENGTH: 1608
<212> TYPE: DNA
<213> ORGANISM: Artificial Sequence
<220> FEATURE:
<223> OTHER INFORMATION: Codon-optimized Glucocerebrosidase

<400> SEQUENCE: 2

atggaattca gcagccccag cagagaggaa tgccccaagc ctctgagccg ggtgtcaatc     60

atggccggat ctctgacagg actgctgctg cttcaggccg tgtcttgggc ttctggcgct    120

agaccttgca tccccaagag cttcggctac agcagcgtcg tgtgcgtgtg caatgccacc    180

tactgcgaca gcttcgaccc tcctaccttt cctgctctgg gcaccttcag cagatacgag    240

agcaccagat ccggcagacg gatggaactg agcatgggac ccatccaggc caatcacaca    300

ggcactggcc tgctgctgac actgcagcct gagcagaaat tccagaaagt gaaaggcttc    360

ggcggagcca tgacagatgc cgccgctctg aatatcctgg ctctgtctcc accagctcag    420

aacctgctgc tcaagagcta cttcagcgag gaaggcatcg gctacaacat catcagagtg    480

cccatggcca gctgcgactt cagcatcagg acctacacct acgccgacac acccgacgat    540

ttccagctgc acaacttcag cctgcctgaa gaggacacca agctgaagat ccctctgatc    600

cacagagccc tgcagctggc acaaagaccc gtgtcactgc tggcctctcc atggacatct    660

cccacctggc tgaaaacaaa tggcgccgtg aatggcaagg gcagcctgaa aggccaacct    720

ggcgacatct accaccagac ctgggccaga tacttcgtga agttcctgga cgcctatgcc    780

gagcacaagc tgcagttttg ggccgtgaca gccgagaacg aaccttctgc tggactgctg    840

agcggctacc cctttcagtg cctgggcttt acacccgagc accagcggga ctttatcgcc    900

cgtgatctgg gacccacact ggccaatagc acccaccata atgtgcggct gctgatgctg    960

gacgaccaga gactgcttct gccccactgg gctaaagtgg tgctgacaga tcctgaggcc   1020

gccaaatacg tgcacggaat cgccgtgcac tggtatctgg actttctggc ccctgccaag   1080

gccacactgg gagagacaca cagactgttc cccaacacca tgctgttcgc cagcgaagcc   1140

tgtgtgggca gcaagttttg ggaacagagc gtgcggctcg gcagctggga tagaggcatg   1200

cagtacagcc acagcatcat caccaacctg ctgtaccacg tcgtcggctg gaccgactgg   1260

aatctggccc tgaatcctga aggcggccct aactgggtcc gaaacttcgt ggacagcccc   1320

atcatcgtgg acatcaccaa ggacaccttc tacaagcagc ccatgttcta ccacctggga   1380

cacttcagca agttcatccc cgagggctct cagcgcgttg gactggtggc ttcccagaag   1440

aacgatctgg acgccgtggc tctgatgcac cctgatggat ctgctgtggt ggtggtcctg   1500

aaccgcagca gcaaagatgt gcccctgacc atcaaggatc ccgccgtggg attcctggaa   1560

acaatcagcc ctggctactc catccacacc tacctgtggc gtagacag                1608


<210> SEQ ID NO 3
<211> LENGTH: 593
<212> TYPE: PRT
<213> ORGANISM: Homo sapiens

<400> SEQUENCE: 3
```

-continued

```
Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
```

```
            420                 425                 430

Arg Ala Ser Leu Ser His Pro Arg Asp Ile Gly Cys Asp Gln His Thr
        435                 440                 445

Ser Cys Pro Val Gly Gln Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
    530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu
```

<210> SEQ ID NO 4
<211> LENGTH: 1779
<212> TYPE: DNA
<213> ORGANISM: Artificial Sequence
<220> FEATURE:
<223> OTHER INFORMATION: Codon-optimized Progranulin

<400> SEQUENCE: 4

```
atgtggaccc tggtgagctg ggtggccctg accgccggcc tggtggccgg cacccgctgc     60

cccgacggcc agttctgccc cgtggcctgc tgcctggacc ccggcggcgc cagctacagc    120

tgctgccgcc ccctgctgga caagtggccc accaccctga gccgccacct gggcggcccc    180

tgccaggtgg acgcccactg cagcgccggc cacagctgca tcttcaccgt gagcggcacc    240

agcagctgct gccccttccc cgaggccgtg gcctgcggcg acggccacca ctgctgcccc    300

cgcggcttcc actgcagcgc cgacggccgc agctgcttcc agcgcagcgg caacaacagc    360

gtgggcgcca tccagtgccc cgacagccag ttcgagtgcc ccgacttcag cacctgctgc    420

gtgatggtgg acggcagctg ggctgctgc cccatgcccc aggccagctg ctgcgaggac     480

cgcgtgcact gctgccccca cggcgccttc tgcgacctgg tgcacacccg ctgcatcacc    540

cccaccggca cccacccccct ggccaagaag ctgcccgccc agcgcaccaa ccgcgccgtg    600

gccctgagca gcagcgtgat gtgccccgac gcccgcagcc gctgccccga cggcagcacc    660

tgctgcgagc tgcccagcgg caagtacggc tgctgcccca tgcccaacgc cacctgctgc    720

agcgaccacc tgcactgctg cccccaggac accgtgtgcg acctgatcca gagcaagtgc    780

ctgagcaagg agaacgccac caccgacctg ctgaccaagc tgcccgccca caccgtgggc    840

gacgtgaagt gcgacatgga ggtgagctgc cccgacggct acacctgctg ccgcctgcag    900

agcggcgcct ggggctgctg ccccttcacc caggccgtgt gctgcgagga ccacatccac    960

tgctgccccg ccggcttcac ctgcgacacc cagaagggca cctgcgagca gggcccccac   1020

caggtgccct ggatggagaa ggcccccgcc cacctgagcc tgcccgaccc ccaggccctg   1080
```

```
aagcgcgacg tgccctgcga caacgtgagc agctgcccca gcagcgacac ctgctgccag   1140

ctgaccagcg gcgagtgggg ctgctgcccc atccccgagg ccgtgtgctg cagcgaccac   1200

cagcactgct gcccccaggg ctacacctgc gtggccgagg gccagtgcca gcgcggcagc   1260

gagatcgtgg ccggcctgga gaagatgccc gcccgccgcg ccagcctgag ccaccccgc    1320

gacatcggct gcgaccagca caccagctgc cccgtgggcc agacctgctg ccccagcctg   1380

ggcggcagct gggcctgctg ccagctgccc cacgccgtgt gctgcgagga ccgccagcac   1440

tgctgccccg ccggctacac ctgcaacgtg aaggcccgca gctgcgagaa ggaggtggtg   1500

agcgcccagc ccgccacctt cctggcccgc agcccccacg tgggcgtgaa ggacgtggag   1560

tgcggcgagg gccacttctg ccacgacaac cagacctgct gccgcgacaa ccgccagggc   1620

tgggcctgct gcccctaccg ccagggcgtg tgctgcgccg accgccgcca ctgctgcccc   1680

gccggcttcc gctgcgccgc ccgcggcacc aagtgcctgc gccgcgaggc cccccgctgg   1740

gacgcccccc tgcgcgaccc cgccctgcgc cagctgctg                           1779
```

<210> SEQ ID NO 5
<211> LENGTH: 145
<212> TYPE: DNA
<213> ORGANISM: Dependoparvovirus Adeno-associated virus 2

<400> SEQUENCE: 5

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag agagggagtg gccaa                                          145
```

<210> SEQ ID NO 6
<211> LENGTH: 20
<212> TYPE: DNA
<213> ORGANISM: Artificial Sequence
<220> FEATURE:
<223> OTHER INFORMATION: AAV9-GBA1 specific primer

<400> SEQUENCE: 6

```
gactgtggga tccgttcgaa                                                 20
```

<210> SEQ ID NO 7
<211> LENGTH: 19
<212> TYPE: DNA
<213> ORGANISM: Artificial Sequence
<220> FEATURE:
<223> OTHER INFORMATION: AAV9-GBA1 specific primer

<400> SEQUENCE: 7

```
gattgacacc cggctcaga                                                  19
```

<210> SEQ ID NO 8
<211> LENGTH: 23
<212> TYPE: DNA
<213> ORGANISM: Artificial Sequence
<220> FEATURE:
<223> OTHER INFORMATION: AAV9-GBA1 specific probe
<220> FEATURE:
<221> NAME/KEY: misc_feature
<222> LOCATION: (1)..(1)
<223> OTHER INFORMATION: 6-FAM fluorescent dye attached
<220> FEATURE:
<221> NAME/KEY: misc_feature
<222> LOCATION: (23)..(23)
<223> OTHER INFORMATION: TAMRA fluorescent dye attached

```
<400> SEQUENCE: 8

ccatggaatt cagcagcccc agc                                          23


<210> SEQ ID NO 9
<211> LENGTH: 20
<212> TYPE: DNA
<213> ORGANISM: Artificial Sequence
<220> FEATURE:
<223> OTHER INFORMATION: AAV9-GRN specific primer

<400> SEQUENCE: 9

gtcttccacg actgtgggat                                              20


<210> SEQ ID NO 10
<211> LENGTH: 18
<212> TYPE: DNA
<213> ORGANISM: Artificial Sequence
<220> FEATURE:
<223> OTHER INFORMATION: AAV9-GRN specific primer

<400> SEQUENCE: 10

gtcagggcca cccagctc                                                18


<210> SEQ ID NO 11
<211> LENGTH: 24
<212> TYPE: DNA
<213> ORGANISM: Artificial Sequence
<220> FEATURE:
<223> OTHER INFORMATION: AAV9-GRN specific probe
<220> FEATURE:
<221> NAME/KEY: misc_feature
<222> LOCATION: (1)..(1)
<223> OTHER INFORMATION: 6-FAM fluorescent dye attached
<220> FEATURE:
<221> NAME/KEY: misc_feature
<222> LOCATION: (24)..(24)
<223> OTHER INFORMATION: TAMRA fluorescent dye attached

<400> SEQUENCE: 11

ccggttgagc caccatgtgg accc                                         24


<210> SEQ ID NO 12
<211> LENGTH: 23
<212> TYPE: DNA
<213> ORGANISM: Artificial Sequence
<220> FEATURE:
<223> OTHER INFORMATION: inhibitory nucleic acid targeting alpha-
      synuclein

<400> SEQUENCE: 12

tggaagactt cgagatacac tgt                                          23
```

RECOMBINANT ADENO-ASSOCIATED VIRUS COMPOSITIONS AND METHODS FOR PRODUCING SAME

CROSS-REFERENCE TO RELATED APPLICATIONS

This application claims the benefit of U.S. Provisional Patent Application No. 63/092,179, filed on Oct. 15, 2020, the disclosure of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVL_013_01US_SeqList_ST25.txt, date recorded: Oct. 15, 2021, file size 16,966 bytes).

TECHNICAL FIELD

The disclosure relates generally to the field of gene therapy. More specifically, the disclosure provides a recombinant baculovirus system and methods of using the same for producing compositions comprising recombinant adeno-associated viruses.

BACKGROUND

Recombinant adeno-associated virus (rAAV) has become widely used as a vector for gene therapy. There has been a growing need for rAAV for non-human primate studies, human clinical trials and medical treatment. Recombinant baculovirus systems have been used for production of rAAV. There remains a need for baculovirus-based processes that result in high yields of rAAV with improved purity that are suitable for use in gene therapy protocols.

SUMMARY

Provided herein is a method for producing a cellular lysate, the method comprising: (i) obtaining a bioreactor containing insect cells suspended in a mixture comprising two or more serum-free, and/or protein-free insect cell culture medias; (ii) infecting the insect cells with a first population of Baculovirus vectors at a multiplicity of infection (MOI) of between about 1.0 and 2.0, wherein the first population of Baculovirus vectors comprise an expression cassette encoding a gene product of interest; (iii) infecting the insect cells with one or more additional populations of Baculovirus vectors at a MOI of between about 1.0 and 2.0, wherein the additional populations each comprise an expression cassette encoding AAV Rep protein and/or AAV Cap protein; (iv) culturing the infected insect cells under conditions under which the infected insect cells produce rAAV particles encoding the gene of interest; and (v) lysing the infected insect cells to produce a cellular lysate comprising the rAAV particles. In some embodiments, each of the two or more serum-free and/or protein-free insect culture medias are selected from 4Cell Insect CD Medium, ESF-921, ESF-AF, ExpiSf CD Medium, Express Five SFM, baculoGROW, IS SF, and SF900 II SFM. In some embodiments, the mixture comprises from about 10% v/v to about 50% v/v SF900 II SFM media.

In some embodiments, the insect cells of step (i) are obtained after 4-6 passages of a master seed train. In some embodiments, the infection of step (ii) and the infection of step (iii) occur simultaneously.

In some embodiments, the insect cells are present in the bioreactor at a cell density of between 8E+06 viable cells per mL (vc/mL) to about 20E+06 vc/mL.

In some embodiments, the culturing of step (iv) occurs for between 1 day and 5 days. In some embodiments, the lysing of step (v) comprises contacting the infected insect cells with a detergent.

In some embodiments, a method for producing a cellular lysate further comprises the step of clarifying the cellular lysate by depth filtration. In some embodiments, a method for producing a cellular lysate further comprises the step of concentrating the rAAV particles in the lysate by tangential flow filtration and/or diafiltration.

In some embodiments, the gene product of interest comprises a peptide, polypeptide, inhibitory nucleic acid, or a combination thereof. In some embodiments, the gene product of interest comprises glucocerebrosidase (GCase), progranulin (PGRN), prosaposin (PSAP), C9orf72, triggering receptor expressed on myeloid cells 2 (TREM2), apolipoprotein E2 (ApoE2) or parkin.

In some embodiments, the cellular lysate comprises rAAV particles that comprise an AAV capsid protein that is AAV1, AAV2, AAV3, AAV4, AAV5, AAV6, AAV7, AAV8, AAV9 or a variant of any of the foregoing.

In some embodiments, the cellular lysate comprises (a) from about 1E+11 viral genomes per milliliter (vg/mL) to about 1.0E+13 vg/mL; (b) from about 2E+11 vg/mL to about 1.0E+13 vg/mL; or (c) from about 5E+11 vg/mL to about 1.0E+13 vg/mL.

Provided herein is a pharmaceutical composition comprising the cellular lysate produced by any of the methods disclosed herein. In some embodiments, the composition further comprises a cryoprotectant.

Provided herein is a method for producing a therapeutic composition, the method comprising: (i) obtaining a cellular lysate comprising rAAV particles; (ii) contacting an affinity chromatography column with the cellular lysate, wherein the affinity column comprises a binding agent specific for a capsid protein of the rAAV particles under conditions under which the rAAV particles bind to the affinity chromatography column; (iii) eluting the bound rAAV particles from the column thereby producing a first eluate; (iv) performing anion-exchange chromatography on the first eluate to produce a second eluate, wherein the second eluate comprises fewer empty rAAV particles than the first eluate; (v) concentrating the second eluate by performing tangential flow filtration using a flow buffer comprising Tris, $MgCl_2$, NaCl, and Poloxamer 188, thereby producing a therapeutic composition comprising rAAV particles. In some embodiments, the cellular lysate of step (i) is obtained by any of the methods for producing a cellular lysate disclosed herein. In some embodiments, the binding agent comprises an affinity resin specific for AAV9 capsid protein.

In some embodiments, the anion-exchange chromatography comprises mixing the first eluate with an equilibration buffer to produce a mixture having a conductivity of between about 0.5 mS/cm to 5 mS/cm, optionally wherein the mixture has a conductivity of 2 mS/cm, binding the mixture to a quaternary amine-containing resin to bind the rAAV particles in the mixture to the resin, and eluting the rAAV particles from the resin to produce the second eluate.

In some embodiments, the second eluate is concentrated to from about 1.0E+12 vg/mL to about 1E+14 vg/mL. In some embodiments, the therapeutic composition comprises from about 1E+13 vg/mL to about 1E+14 vg/mL. In some embodiments, the therapeutic composition comprises less than about 15% empty rAAV particles.

Provided herein is a therapeutic composition comprising rAAV particles, wherein the rAAV particle comprises an AAV capsid protein and an expression cassette encoding a gene product of interest, wherein the therapeutic composition comprises more than about 1E+13 vg/mL rAAV particles, and wherein the therapeutic composition comprises less than about 15% empty rAAV particles. In some embodiments, the gene product of interest comprises a peptide, polypeptide, inhibitory nucleic acid, or a combination thereof. In some embodiments, the gene product of interest comprises GCase, GRN, PSAP, TREM2, ApoE2 or parkin. In some embodiments, the rAAV particles comprise an AAV capsid protein that is AAV1, AAV2, AAV3, AAV4, AAV5, AAV6, AAV7, AAV8, AAV9 or a variant of any of the foregoing.

In some embodiments, the therapeutic composition comprises from about 1E+13 vg/mL to about 1E+14 vg/mL.

In some embodiments, the therapeutic composition is in a container. In some embodiments, the therapeutic composition is sterile. In some embodiments, the therapeutic composition does not promote microbial growth. In some embodiments, the therapeutic composition comprises an endotoxin level less than about 0.5 EU/mL.

In some embodiments, the rAAV particle comprises AAV9 capsid protein.

In some embodiments, more than about 1.0E+13 vg/mL of the rAAV comprises the gene product. In some embodiments, the TCID50 titer of the rAAV is from about 1,000 vg/IU to about 6,000 vg/IU.

In some embodiments, the gene product is GCase. In some embodiments, the GCase activity is at least 110% relative to a reference standard, wherein the reference standard is a purified rAAV encoding GCAse.

In some embodiments, the infectious titer is from about 8.0E+9 IU/mL to about 1.2E+10 IU/mL.

In some embodiments, the osmolality is between about 300 mOsm/kg and about 500 mOsm/kg. In some embodiments, the pH is between about 7 and about 9.

In some embodiments, the therapeutic composition is free from visible particles. In some embodiments, the therapeutic composition comprises less than about 6000 particles that are larger than about 10 μm per container, and less than about 600 particles that are larger than about 25 μm per container. In some embodiments, the therapeutic composition comprises less than or equal to about 3% aggregates.

In some embodiments, therapeutic composition comprises a total protein level from about 300 μg/mL to about 1000 μg/mL.

In some embodiments, the purity of the rAAV is more than about 90% v/v.

In some embodiments, the therapeutic composition does not comprise any single impurity greater than about 5% v/v. In some embodiments, the therapeutic composition comprises from about 0.0007% to about 0.0012% of Pluronic. In some embodiments, the therapeutic composition comprises less than about $5.5\times10^4$ copies RNA/mL of Rhabdovirus.

In some embodiments, the extractable volume of the therapeutic composition in the container is equal to or greater than about 1.0 mL.

BRIEF DESCRIPTION OF THE DRAWINGS

FIG. 1 is a diagram of a PCR plate map for a rAAV potency assay. "RS" refers to "reference standard". "TS" refers to "test sample".

DETAILED DESCRIPTION

Figure 2:
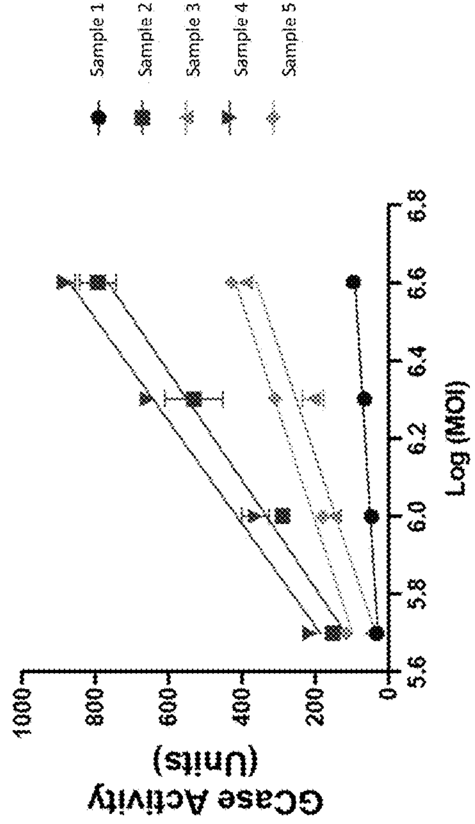
FIG. 2 depicts a line graph and calculations of relative potency of several rAAV samples expressing GCase.

The disclosure relates to pharmaceutical compositions comprising rAAV with high yield and sufficient purity that are suitable for administration in gene therapy protocols. The disclosure also relates to methods of using recombinant baculovirus systems for producing compositions comprising rAAV with high yield and high purity.

The term "recombinant virus" refers to a virus that has been genetically altered, e.g., by the addition or insertion of a heterologous nucleic acid construct into the viral particle.

The term "heterologous" is used herein interchangeably with the term "exogenous", and refers to a substance coming from some source other than its native source. For example, the term "exogenous protein" or "exogenous gene" refers to a protein or gene from a non-AAV source that has been artificially introduced into an AAV genome or AAV particle.

The term "recombinant adeno-associated virus" or "rAAV" refers to a AAV particle or AAV virion comprising a rAAV vector encapsidated by one or more AAV capsid proteins.

The term "rAAV vector" refers to nucleic acids, either single-stranded or double-stranded, having an AAV 5' inverted terminal repeat (ITR) sequence and an AAV 3' ITR flanking a protein-coding sequence operably linked to transcription regulatory elements that are heterologous to the AAV viral genome, for example, one or more promoters and/or enhancers and, optionally, a polyadenylation sequence and/or one or more introns inserted between exons of the protein-coding sequence.

The term "full rAAV particle" or "full rAAV capsid" refers to an AAV virion that comprises an AAV structural protein shell encapsidating a nucleic acid molecule comprising an exogenous gene of interest flanked on both sides by AAV ITRs.

The term "empty rAAV particle" or "empty rAAV capsid" refers to an AAV virion that comprises an AAV structural protein shell but that lacks in whole or part the polynucleotide construct comprising an exogenous gene of interest flanked on both sides by AAV ITRs. The empty rAAV particle does not function to transfer the gene of interest into a host cell.

In some embodiments, the term "eluent" refers to the buffer used to elute a substance. In some embodiments, the term "eluent" may be understood, in context, to refer to the eluted substance, e.g., the desired product or substance from a prior purification step, e.g., for assaying or further purification.

The term "reference standard" refers to a composition comprising an AAV vector encoding an exogenous protein of interest, whose concentration and/or potency is known.

The term "IU" refers to infectious units.

The term "TCID50" refers to the 50% cell culture infectious dose.

The term "USP" refers to the United States Pharmacopeia.

Therapeutic Compositions Comprising Recombinant Adeno-Associated Virus

Provided herein are therapeutic compositions comprising rAAV. In some aspects, the therapeutic compositions provided herein are suitable for gene therapy.

In some aspects, provided herein is a therapeutic composition comprising rAAV particles, wherein the rAAV particle comprises an AAV capsid protein and an expression cassette encoding a gene product of interest, wherein the therapeutic composition comprises more than 1E+13 vg/mL rAAV particles, and wherein the therapeutic composition comprises less than 15% empty rAAV particles.

In some embodiments, the gene product of interest comprises a peptide, polypeptide, inhibitory nucleic acid, or a combination thereof.

In some embodiments, the gene product of interest is human GCase or human progranulin (PGRN or GRN). In some embodiments, the gene product of interest is human PSAP, human C9orf72, human TREM2, human ApoE2 or human parkin.

In some embodiments, the inhibitory nucleic acid is an inhibitory RNA. In some embodiments, the inhibitory nucleic acid is a double stranded RNA (dsRNA), siRNA, micro RNA (miRNA), artificial miRNA (amiRNA), short hairpin RNA (shRNA) or an RNA aptamer. An artificial microRNA (amiRNA) may be derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest. An artificial precursor microRNA (pre-amiRNA) is normally processed such that one single stable small RNA is preferentially generated. In some embodiments, scAAV vectors and scAAVs described herein comprise a nucleic acid encoding an amiRNA. In some embodiments, the pri-miRNA scaffold of the amiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451. In some embodiments, an amiRNA comprises an eSIBR amiRNA scaffold, for example as described in Fowler et al. (2016) *Nucleic Acids Res.* 44(5):e48. In some embodiments, an amiRNA comprises a miR-7-2 scaffold.

In some embodiments, the inhibitory RNA targets human α-synuclein, human ataxin 2 (ATXN2), human microtubule-associated protein tau (MAPT), or human apolipoprotein E (ApoE). In some embodiments, a rAAV vector comprises a polynucleotide encoding human GCase (e.g., SEQ ID NO: 2) and a polynucleotide encoding an inhibitory RNA targeting human α-synuclein. In some embodiments, a polynucleotide encoding an inhibitory RNA targeting human α-synuclein comprises SEQ ID NO: 12. In some embodiments, a rAAV vector comprises a polynucleotide encoding human C9orf72 (i.e., functional C9orf72) and a polynucleotide encoding an inhibitory RNA targeting human C9orf72. In some embodiments, a rAAV vector comprises a polynucleotide encoding human ApoE2 (i.e., functional ApoE2) and a polynucleotide encoding an inhibitory RNA targeting human ApoE. In some embodiments, a single nucleic acid molecule comprises the polynucleotide encoding an exogenous protein and the polynucleotide encoding an inhibitory RNA. In some embodiments, a rAAV vector comprises a polynucleotide encoding human TREM2 (i.e., functional TREM2) and a polynucleotide encoding an inhibitory RNA targeting human TREM2.

Examples of suitable rAAV vectors that can be used in the compositions and methods disclosed herein are disclosed in WO2019/070891, WO2019/070893, WO2019/070894, and WO2019/084068, the disclosure of each of which is incorporated by reference herein in its entirety.

In some embodiments of the therapeutic compositions disclosed herein, a rAAV vector further comprises one or more of the following: a chicken beta actin (CBA) promoter; a cytomegalovirus (CMV) enhancer; a Woodchuck Hepatitis Virus Posttranscriptional Regulatory Element (WPRE); a Bovine Growth Hormone polyA signal tail; an artificial intron; an artificial exon; and one or more of the following transcriptional regulatory activation sites in a promoter region: TATA, RBS, and YY1 (Francois et al. (2005) *J. Virol.* 79(17):11082-11094). The TATA, RBS and YY1 transcriptional regulatory activation sites may be located at the 5' end of the promoter region.

In some embodiments of the therapeutic compositions disclosed herein, a rAAV vector comprises a first AAV inverted terminal repeat (ITR) and a second ITR flanking the polynucleotide encoding a gene product of interest and the related regulatory sequences. In some embodiments, each ITR is a wild-type AAV2 ITR (SEQ ID NO: 5). In some embodiments, each ITR is derived from a wild-type AAV2 ITR.

In some embodiments of the therapeutic compositions disclosed herein, a rAAV vector comprises, in sequential order, a first AAV ITR, a CMV enhancer, a CBA promoter, the polynucleotide encoding a human GCase protein, a WPRE, a Bovine Growth Hormone polyA signal tail and a second AAV ITR. In some embodiments, the polynucleotide encoding a human GCase protein is codon optimized (e.g., codon optimized for expression in human cells). In some embodiments, the polynucleotide encoding a human GCase protein comprises SEQ ID NO: 2.

In some embodiments of the therapeutic compositions disclosed herein, a rAAV vector comprises, in sequential order, a first AAV ITR, a CMV enhancer, a CBA promoter, the polynucleotide encoding a human PGRN protein, a WPRE, a Bovine Growth Hormone polyA signal tail and a second AAV ITR. In some embodiments, the polynucleotide encoding a human PGRN protein is codon optimized (e.g., codon optimized for expression in human cells). In some embodiments, the polynucleotide encoding a human PGRN protein comprises SEQ ID NO: 4.

In some embodiments of the therapeutic compositions disclosed herein, a rAAV vector is a self-complementary recombinant adeno-associated virus (scAAV) vector. scAAV vectors are described in, for example, McCarty et al. (2001) *Gene Ther.* 8(16): 1248-54.

In some embodiments of the therapeutic compositions disclosed herein, a rAAV comprises an AAV9 capsid protein. In some embodiments of the compositions disclosed herein, a rAAV comprises an AAV1, AAV2, AAV3, AAV4, AAV5, AAV6, AAV7, AAV8, AAV9, AAV10 or AAV11 capsid protein, or a variant of any of these capsid proteins.

The genome titer (also referred to as physical titer) of rAAV vectors, e.g., those in the compositions and formulations disclosed herein, can be determined in a number of ways. PCR with primers specific to the viral vector can provide relative measurements. Quantitative PCR (qPCR) may be used for smaller samples and absolute measurements. Droplet Digital PCR (ddPCR) is a method for performing digital PCR that is based on water-oil emulsion droplet technology. A sample is fractionated into tens of thousands of droplets, and PCR amplification of the template molecules occurs in each individual droplet. One does not need to make a standard curve or have primers with high amplification efficiency, hence ddPCR does not typically use as much sample as traditional PCR-based techniques. In some embodiments, the genome titer of the viral vector is determined using PCR. In some embodiments, the genome titer of the viral vector is determined using qPCR. In some embodiments, the genome titer of the viral vector is determined using ddPCR. A method of determining viral genome titer using ddPCR is described, for instance, in Lock et al. (2014) *Hum Gene Ther Methods* 25(2):115-25. In some embodiments, the genome titer of the viral vector is determined using the method provided in Example 11 or Example 13. In some embodiments, the physical titer of the therapeutic composition is greater than or equal to about $2.0\times10^{13}$ vg/mL, about $3.0\times10^{13}$ vg/mL, about $4.0\times10^{13}$ vg/mL, or about $5.0\times10^{13}$ vg/mL. In some embodiments, the physical titer of the therapeutic composition is from about $2.0\times10^{13}$ vg/mL to about $5.0\times10^{13}$ vg/mL. In some embodiments, a therapeutic composition comprises more than 1E+13 vg/mL rAAV particles. In some embodiments, a therapeutic composition comprises about 1E+13 vg/mL to about 1E+14 vg/mL rAAV particles.

The infectious titer (also referred to as functional titer) of rAAV vectors, e.g., those in the compositions and formulations disclosed herein, is the concentration of viral particles that can infect cells. In some embodiments, infectious titer is determined by a cell transduction assay. In some embodiments, the infectious titer of the viral vector is determined using the method provided in Example 12 or Example 14. In some embodiments, the infectious titer of a composition disclosed herein is from about 8.0E+9 IU/mL to about 1.2E+10 IU/mL. In some embodiments, the infectious titer of a composition disclosed herein is about 8.0E+9 IU/mL, about 8.15E+9 IU/mL, about 8.5E+9 IU/mL, about 9.0E+9 IU/mL, about 9.5E+9 IU/mL, about 9.99E+9 IU/mL, about 1E+10 IU/mL, about 1.12E+10 IU/mL or about 1.2E+10 IU/mL. In some embodiments, the TCID50 of a composition disclosed herein is from about 4,500 vg/IU to about 10,000 vg/IU. In some embodiments, the TCID50 of a composition disclosed herein is from about 1,000 vg/IU to about 6,000 vg/IU. In some embodiments, the TCID50 of a composition disclosed herein is about 4,500 vg/IU, about 5,000 vg/IU, about 5,500 vg/IU, about 6,000 vg/IU, about 6,290 vg/IU, about 6,500 vg/IU, about 7,000 vg/IU, about 7,500 vg/IU, about 8,000 vg/IU, about 8,500 vg/IU, about 9,000 vg/IU, about 9,500 vg/IU, about 9,980 vg/IU or about 10,000 vg/IU.

In some embodiments, the PCR-based methods detect and quantify encapsidated rAAV genomes using specifically designed primers and probes targeting the exogenous gene. In some embodiments, the PCR-based methods detect and quantify encapsidated rAAV genomes using specifically designed primers and probes targeting the CBA promoter. In some embodiments, the PCR-based methods detect and quantify encapsidated rAAV genomes using specifically designed primers and probes targeting the CMV enhancer. In some embodiments, the PCR-based methods detect and quantify encapsidated rAAV genomes using specifically designed primers and probes targeting the ITR sequences. In some embodiments, the PCR-based methods detect and quantify encapsidated rAAV genomes using specifically designed primers and probes targeting the Bovine Growth Hormone polyadenylation (polyA) signal tail.

In some cases, during the production process of the rAAV-containing compositions, compositions comprising impurities may be generated. Pharmaceutical compositions comprising low amounts of impurities may be advantageous, because they avoid exposing subjects (e.g., infants) with immature or compromised immune systems to antigenic material (e.g., empty capsids, host cell protein, host cell DNA) unnecessarily without therapeutic benefit. In some embodiments, such pharmaceutical compositions may reduce potential infusion reactions or broader immune responses and may improve therapeutic efficacy.

In some embodiments, empty rAAV particles (also referred to as "empty capsids") that do not contain nucleic acid material may be generated during the AAV production process. Compared to full viral particles with rAAV vector material, empty particles have different densities, allowing the two species to be separated by methods known in the art. In some embodiments, the empty capsids are separated by chromatography (e.g., monolith chromatography, or more specifically, convective interaction media monolith chromatography).

In some embodiments, the ratio of empty rAAV particles to full rAAV particles can be measured by standard laboratory techniques. In some embodiments, the ratio is measured by transmission electron microscopy (TEM). In some embodiments, the ratio is measured by optical absorbance measurements. In some embodiments, the ratio is measured by UV absorbance measurements.

In some embodiments, a therapeutic composition disclosed herein comprises less than about 15% empty rAAV particles. In some embodiments, a therapeutic composition comprises less than about 10%, less than about 8% empty rAAV particles, less than 7%, less than about 5%, less than about 3%, or less than about 1% empty rAAV particles. In some embodiments, a therapeutic composition comprises from about 1% to about 10% empty rAAV particles. In some embodiments, a therapeutic composition comprises from about 2% to about 8% empty rAAV particles. In some embodiments, a therapeutic composition comprises less than or equal to about 6% empty rAAV particles, about 5% empty rAAV particles, about 4% empty rAAV particles, about 3% empty rAAV particles, about 2% empty rAAV particles, or about 1% empty rAAV particles. In some embodiments, the number of empty rAAV particles is below the limit of detection. In some embodiments, the percentage of empty rAAV particles is determined as a percentage of total rAAV particles, e.g., using analytical ultracentrifugation (AUC). In some embodiments, these low percentages of empty rAAV particles improve efficacy of treatment and/or reduce adverse events (e.g., inflammatory responses, liver injury) after administration to a subject, e.g., as compared to administering compositions having higher percentage empty rAAV particles. In some embodiments, the methods of preparing rAAV compositions disclosed herein provide these low percentages of empty rAAV particles, as compared to the levels of empty rAAV particles produced in other methods, e.g., those not using the production and/or the purification methods described herein.

In some embodiments, a therapeutic composition disclosed herein comprises at least 80% full rAAV particles. In some embodiments, a therapeutic composition comprises at least 85% full rAAV particles, at least 90% full rAAV particles, or at least 95% full rAAV particles.

In some embodiments, during the production process of the rAAV compositions, residual protein from the insect cells (e.g., Sf9 cells) used to generate the rAAV particles may not be completely separated out. Residual host cell proteins pose a potential to elicit an immune response in a gene therapy subject. The amount of residual host cell protein can be measured by any standard laboratory techniques that can distinguish between the viral capsid proteins and the residual host cell proteins. In some embodiments, the amount of residual host cell proteins can be measured by size exclusion or ion exchange chromatography. In some embodiments, the measurement can be done the amount of residual host cell proteins can be measured by a western blot with parental cell-specific antibodies. In some embodiments, the amount of residual host cell protein can be measured by enzyme-linked immunosorbent assay (ELISA). In some embodiments, the amount of residual host cell protein can be measured by a commercial ELISA kit.

In some embodiments, the residual host cell protein in a therapeutic composition disclosed herein is less than or equal to about 45 ng/1E+13 vg, 42 ng/1E+13 vg, 40 ng/1E+13 vg, 35 ng/1E+13 vg, 30 ng/1E+13 vg, about 29 ng/1E+13 vg, about 28 ng/1E+13 vg, about 27 ng/1E+13 vg, about 26 ng/1E+13 vg, or about 25 ng/1E+13 vg.

In some cases, during the production process of the rAAV compositions, residual host cell DNA from the insect cells (e.g., Sf9 cells) or residual baculovirus DNA or bacmid DNA used to generate the rAAV vectors may not be completely removed. The purification processes (e.g., clarification, tangential flow filtration, etc.) may remove the bulk of residual host cell DNA or baculovirus DNA. In some embodiments, measurement of the amount of residual host cell or baculovirus DNA is performed by PCR (polymerase chain reaction). In some embodiments, measurement of the amount of residual host cell or baculovirus DNA is performed by qPCR with primers specific for host cell or baculovirus sequences. In some embodiments, measurement of the amount of residual host cell or baculovirus DNA is performed by ddPCR. In some embodiments, the amount of baculovirus or bacmid DNA is determined using a qPCR assay with primers specific to an antibiotic resistance gene region of a bacmid. In some embodiments, the amount of residual host cell DNA is determined by commercial qPCR assay kits. Reducing the amount of residual host cell or baculovirus or bacmid DNA may improve therapeutic outcomes, and such compositions may be purified and/or selected for use in treatments disclosed herein.

In some embodiments, the amount of residual host cell DNA in a pharmaceutical composition disclosed herein is less than or equal to about 1E+03 μg/ml per 1E+14 vg/ml. In some embodiments, a pharmaceutical composition comprises less than or equal to about 1.3 ng residual host cell DNA per 1E+14 vg/mL. In some embodiments, the amount of residual host cell DNA in a pharmaceutical composition disclosed herein is below the limit of quantitation.

In some embodiments, the therapeutic compositions disclosed herein comprising any of the viral particles disclosed herein retain a potency of between ±20%, between ±15%, between ±10%, or between ±5%, of a reference standard. In some embodiments, a therapeutic composition described herein comprises a viral vector, wherein the relative potency of the viral vector is at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.9%, at least 100%, at least 110%, at least 120%, at least 130% or at least 140% relative to a reference standard. In some embodiments, potency is measured using a suitable in vitro cellular assay or in vivo animal model. In some embodiments, the potency or functional rAAV encoding human GCase may be determined by a cell-based assay using the fluorogenic substrate resorufin-β-D-glucopyranoside, as described below. In some embodiments, the potency or % functional rAAV encoding human progranulin may be determined by a cell-based assay using an ELISA, as described below.

In some embodiments, the therapeutic compositions disclosed herein may contain pharmaceutically acceptable auxiliary substances to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, etc. In some embodiments, the pharmaceutical composition comprises a preservative. In some embodiments, the pharmaceutical composition does not comprise a preservative.

The rAAV compositions disclosed herein can be formulated to prepare pharmaceutically useful compositions. The compositions of the disclosure can be formulated for administration to a mammalian subject, e.g., a human, using techniques known in the art. In some embodiments, rAAV compositions may be formulated for injection into the cisterna magna. In some embodiments, rAAV compositions may be formulated for intravenous administration. In some embodiments, rAAV compositions may be formulated for intramuscular, intradermal, mucosal, subcutaneous, intrathecal, or topical administration.

Further provided herein is a pharmaceutical formulation comprising: (a) a rAAV particle comprising a rAAV vector comprising a polynucleotide encoding a human GCase protein; (b) a Tris buffer; (c) magnesium chloride; (d) sodium chloride; and (e) a poloxamer. In some embodiments, the rAAV vector comprises, in sequential order, a first AAV ITR, a CMV enhancer, a CBA promoter, the polynucleotide encoding a human GCase protein, a WPRE, a Bovine Growth Hormone polyA signal tail and a second AAV ITR. In some embodiments, the polynucleotide encoding a human GCase protein comprises SEQ ID NO: 2. In some embodiments, a rAAV particle comprising a rAAV vector comprising a polynucleotide encoding a human GCase protein is referred to as PR001.

Further provided herein is a pharmaceutical formulation comprising a rAAV particle, about 20 mM Tris pH 8.0, about 1 mM magnesium chloride, about 200 mM sodium chloride and about 0.001% Poloxamer 188, wherein the rAAV comprises a rAAV vector comprising a nucleic acid sequence encoding a human glucocerebrosidase protein, wherein the human glucocerebrosidase protein is encoded by the nucleotide sequence of SEQ ID NO: 2; and wherein the nucleic acid sequence encoding a human glucocerebrosidase protein is flanked by two AAV ITR sequences. In some embodiments, the rAAV particle is an AAV9 particle.

Further provided herein is a pharmaceutical formulation comprising: (a) a rAAV particle comprising a rAAV vector comprising a polynucleotide encoding a human progranulin (PGRN) protein; (b) a Tris buffer; (c) magnesium chloride; (d) sodium chloride; and (e) a poloxamer. In some embodiments, the rAAV vector comprises, in sequential order, a first AAV ITR, a CMV enhancer, a CBA promoter, the polynucleotide encoding a human PGRN protein, a WPRE, a Bovine Growth Hormone polyA signal tail and a second AAV ITR. In some embodiments, the polynucleotide encoding a human PGRN protein comprises SEQ ID NO: 4. In some embodiments, a rAAV particle comprising a rAAV vector comprising a polynucleotide encoding a human PGRN protein is referred to as PR006.

Further provided herein is a pharmaceutical formulation comprising a rAAV particle, about 20 mM Tris pH 8.0, about 1 mM magnesium chloride, about 200 mM sodium chloride and about 0.001% Poloxamer 188, wherein the rAAV comprises a rAAV vector comprising a nucleic acid sequence encoding a human glucocerebrosidase protein, wherein the human progranulin protein is encoded by the nucleotide sequence of SEQ ID NO: 4; and wherein the nucleic acid sequence encoding a human progranulin protein is flanked by two AAV ITR sequences. In some embodiments, the rAAV particle is an AAV9 particle.

In some embodiments, a formulation disclosed herein comprises from about 10 mM to about 30 mM Tris pH 8.0. In some embodiments, a formulation disclosed herein comprises from about 0.5 mM to about 1.5 mM magnesium chloride. In some embodiments, a formulation disclosed herein comprises from about 100 mM to about 300 mM sodium chloride. In some embodiments, a formulation disclosed herein comprises from about 0.001% to about 0.005% Poloxamer 188. In some embodiments, a formulation disclosed herein comprises from about 1E+13 vg/mL to about 5E+13 vg/mL.

In some embodiments, a therapeutic composition disclosed herein has a total aerobic microbial count (TAMC)≤1 CFU/10 mL and a total combined yeast and mold count (TYMC)≤1 CFU/10 mL. TAMC and TYMC amounts may be measured by the Membrane filtration USP <61> method.

In some embodiments, a composition disclosed herein comprises an endotoxin level less than about 0.5 EU/mL, less than about 0.4 EU/mL, less than about 0.3 EU/mL, less than about 0.2 EU/mL, or less than about 0.1 EU/mL. Endotoxin levels may be measured by a kinetic chromogenic method.

In some embodiments, a composition disclosed herein is negative for presence of *Mycoplasma* and *Spiroplasma*. The presence of *Mycoplasma* and *Spiroplasma* may be determined by a *Mycoplasma* with Mycoplasmastasis test (USP <63>).

In some embodiments, adventitious agents are not detected in a composition disclosed herein. The presence of viral contaminants may be determined in vitro by direct inoculation into three cell lines: MRC-5, Vero and Hela cells. The presence of viral contaminants may be determined in vivo by Inoculation in adult mice, guinea pigs, suckling mice and embryonated hen eggs.

In some embodiments, replicative competent AAV is not detected in a composition disclosed herein. The presence of replicative competent AAV may be determined by serial infection and qPCR.

In some embodiments, a composition disclosed herein has purity >about 90% with no single impurity >about 2%. In some embodiments, a composition disclosed herein has purity greater than about 90%, about 95%, or about 99%. In some embodiments, a composition disclosed herein does not comprise any single impurity greater than about 5% v/v, about 4% v/v, about 3% v/v, or about 2% v/v. Purity may be determined by SDS-PAGE SYPRO® Ruby.

In some embodiments, the presence of residual Triton X-100 in a composition disclosed herein is determined by HPLC-RI or by UV light absorbance.

In some embodiments, a composition disclosed herein comprises less than 1.7 ng/$1\times10^{13}$ vg, less than 1.67 ng/$1\times10^{13}$ vg, less than 1.6 ng/$1\times10^{13}$ vg, or less than 1.5 ng/$1\times10^{13}$ vg of residual benzonase. The level of residual benzonase may be measured by ELISA.

In some embodiments, the presence of residual baculovirus in a composition disclosed herein is determined by a BacPAK™ assay.

In some embodiments, the presence of residual SF9 host cell DNA in a composition disclosed herein is determined by qPCR.

In some embodiments, the presence of residual SF9 host cell protein in a composition disclosed herein is determined by ELISA.

In some embodiments, a composition disclosed herein is negative for nodavirus. The presence of nodavirus can be determined by qPCR.

In some embodiments, there is no mycobacterial DNA detected in a composition disclosed herein. The presence of mycobacterial DNA can be determined by qPCR.

In some embodiments, a composition disclosed herein is tested for sterility by membrane filtration USP<71>. In some embodiments, a composition disclosed herein exhibits no growth in this test.

In some embodiments, a composition disclosed herein is tested for Bacteriostasis/Fungistasis by USP<71>. In some embodiments, a composition disclosed herein exhibits no inhibition of growth in this test.

In some embodiments, a composition disclosed herein is tested for the presence of AAV9 capsid by AAV9-specific ELISA.

In some embodiments, a composition disclosed herein is tested for the presence of AAV capsid protein by western blot for viral particle protein.

In some embodiments, a composition disclosed herein is tested for DNA identity by next generation sequencing.

In some embodiments, a composition disclosed herein has an osmolality from about 300 mOsm/kg to about 500 mOsm/kg. In some embodiments, a composition disclosed herein has an osmolality from about 388 mOsm/kg to about 426 mOsm/kg. Osmolality may be measured by a freezing point depression method.

In some embodiments, a composition disclosed herein has a pH from about 7 to about 9. In some embodiments, a composition disclosed herein has a pH of 8.0+/−0.5. pH may be measured by a pH meter.

In some embodiments, a composition disclosed herein is clear to slightly opaque, is a colorless to faint white solution and free from visible particles as determined by visual inspection.

In some embodiments, a composition disclosed herein comprises about 6000 particles/container≥10 μm and ≤about 600 particles/container≥25 μm. Sub visible particulate matter may be measured by the USP<787> method.

In some embodiments, a composition disclosed herein is tested for aggregates by dynamic light scattering (DLS).

In some embodiments, a composition disclosed herein comprises a total protein level from about 300 μg/mL to about 1000 μg/mL. Level of total protein may be measured by the Micro BCA™ protein assay kit.

In some embodiments, a therapeutic composition disclosed herein is in a container. In some embodiments, container closure is tested by a dye ingress test. In some embodiments, the extractable volume of the composition in the container is at least about 1.0 mL.

In some embodiments a composition disclosed herein comprises from about 0.0007% to about 0.0012% of Pluronic.

In some embodiments a composition disclosed herein comprises less than about $5.5\times10^4$ copies RNA/mL of Rhabdovirus.

In some embodiments, a therapeutic composition disclosed herein has one or more of the following: a TAMC≤1 CFU/10 mL; a TYMC≤1 CFU/10 mL; comprises an endotoxin level≤5 EU/mL; is negative for presence of *Mycoplasma* and *Spiroplasma*; shows no evidence of contamination with adventitious viral agents; has a physical titer of ≥$3.0\times10^{13}$ vg/mL; does not exhibit detectable replicative competent AAV; has a purity >90% with no single impurity >2%; has residual benzonase<1.67 ng/$1\times10^{13}$ vg; has ≤15% empty capsids; has <42 ng/$1\times10^{13}$ vg residual Sf9 host cell protein; is negative for nodavirus; and has no mycobacterial DNA detected.

In some embodiments, a therapeutic composition disclosed herein has one or more of the following: exhibits no growth in a sterility test; comprises an endotoxin level≤5 EU/mL; is positive for AAV9 capsid protein; comprises the expected DNA sequence; comprises ≥$3.0\times10^{13}$ vg/mL; has a purity >90% with no single impurity >2%; has an osmolality from about 388 mOsm/kg to about 426 mOsm/kg; has pH 8.0+/−0.5; is clear to slightly opaque; is a colorless to faint white solution; is free from visible particles as determined by visual inspection; comprises 6000 particles/container≥10 μm and ≤600 particles/container≥25 μm; and comprises an extractable volume in a container≥1.0 mL.

In some embodiments, the rAAV-containing compositions and formulations disclosed herein may be used to treat diseases associated with aberrant lysosomal function. In some embodiments, the rAAV-containing compositions and formulations disclosed herein may be used to treat neurodegenerative disorders or diseases. In some embodiments, a composition or formulation disclosed herein comprising rAAV comprising a rAAV vector encoding a human GCase protein can be administered to a subject to treat Gaucher disease or Parkinson's disease (e.g., Parkinson's disease with a GBA1 mutation). In some embodiments, a composition or formulation disclosed herein comprising rAAV comprising a rAAV vector encoding a human progranulin protein can be administered to a subject to treat frontotemporal dementia with a GRN mutation (FTD-GRN). In some embodiments, a composition or formulation disclosed herein comprising rAAV comprising a rAAV vector encoding a human glucocerebrosidase protein and a polynucleotide encoding an inhibitory RNA targeting human α-synuclein can be administered to a subject to treat a synucleinopathy or parkinsonism. In some embodiments, a composition or formulation disclosed herein comprising rAAV comprising a rAAV vector comprising a polynucleotide encoding an inhibitory RNA targeting human α-synuclein can be administered to a subject to treat a synucleinopathy or parkinsonism.

Recombinant Baculoviruses

The methods of the disclosure comprise co-infecting insect cells with populations of recombinant baculoviruses (rBVs) to produce rAAV encoding a gene of interest (also referred to as an exogenous gene). At least two populations of rBVs may be used in the methods of the disclosure. Methods for generating recombinant baculovirus are known in the art (see, e.g., the Bac-to-Bac® Baculovirus Expression System (Invitrogen, Carlsbad, CA)).

In some aspects, a rBV genome is derived from *Autographa californica* multicapsid nucleopolyhedrovirus (AcMNPV), *Bombyx mori* nuclear polyhedrosis virus (BmNPV), *Helicoverpa armigera* (HearNPV) or *Spodoptera exigua* MNPV. In some embodiments, a rBV genome is derived from AcMNPV clone C6.

A first population of rBV vectors may comprise a rBV genome comprising an expression cassette comprising an exogenous gene of interest (GOT) and relevant regulatory sequences. This rBV may be referred to as "rBV GOT". In some embodiments, the rBV genome comprises an expression cassette comprising: (1) a polynucleotide encoding an exogenous protein, (2) a polynucleotide encoding an inhibitory RNA, or (3) a polynucleotide encoding an exogenous protein and a polynucleotide encoding an inhibitory RNA. The expression cassette is flanked by two AAV ITRs. In some embodiments, at least one ITR is an AAV2 ITR (e.g., a wild-type AAV2 ITR (SEQ ID NO: 5)). In some embodiments, at least one ITR is derived from a wild-type AAV2 ITR. In some embodiments, the GOI is a gene encoding human GCase, human PGRN, human PSAP, human C9orf72, human TREM2, human ApoE2 or human parkin. In some embodiments, the inhibitory RNA targets human α-synuclein, human ATXN2, human MAPT, or human ApoE. In some embodiments, the rBV genome comprises a polynucleotide encoding human GCase (e.g., SEQ ID NO: 2) and a polynucleotide encoding an inhibitory RNA targeting human α-synuclein (e.g., SEQ ID NO: 12). In some embodiments, the rBV genome comprises a polynucleotide encoding human C9orf72 (i.e., functional C9orf72) and a polynucleotide encoding an inhibitory RNA targeting human C9orf72. In some embodiments, the rBV genome comprises a polynucleotide encoding human ApoE2 (i.e., functional ApoE2) and a polynucleotide encoding an inhibitory RNA targeting human ApoE. Examples of suitable polynucleotide sequences for including in the rBV genome are disclosed in WO2019/070891, WO2019/070893, WO2019/070894, and WO2019/084068, the disclosure of each of which is incorporated by reference herein in its entirety.

In some aspects, a rBV genome used in the methods disclosed herein comprises a human GBA1 gene, which encodes GCase. In some embodiments, the GCase-encoding nucleotide sequence has been codon optimized (e.g., codon optimized for expression in mammalian cells, for example human cells). In some embodiments, the GCase-encoding nucleotide sequence encodes a protein comprising the amino acid sequence of SEQ ID NO: 1 (e.g., NCBI Reference Sequence NP 000148.2). In some embodiments, the GCase-encoding nucleotide sequence comprises the sequence of SEQ ID NO: 2. In some aspects, an rBV genome used in the methods disclosed herein comprises a human GBA1 gene and further comprises a Bovine Growth Hormone polyA signal tail (bGH), a WPRE, a chicken beta actin promoter (CBAp), a cytomegalovirus enhancer (CMVe), an artificial intron or an artificial exon, or any combination of such sequences.

In some aspects, a rBV genome used in the methods disclosed herein comprises a human PGRN gene (also known as the GRN gene), which encodes PGRN. In some embodiments, the PGRN-encoding nucleotide sequence has been codon optimized (e.g., codon optimized for expression in mammalian cells, for example human cells). In some embodiments, the PGRN-encoding nucleotide sequence encodes a protein comprising the amino acid sequence of SEQ ID NO: 3 (e.g., NCBI Reference Sequence NP_002078.1). In some embodiments, the PGRN-encoding nucleotide sequence comprises the sequence of SEQ ID NO: 4.

Further provided herein is a recombinant baculovirus comprising a genome comprising an exogenous gene of interest, wherein the exogenous gene of interest encodes a human glucocerebrosidase protein; and wherein the human glucocerebrosidase protein is encoded by the nucleotide sequence of SEQ ID NO: 2. Also provided herein is a recombinant baculovirus comprising a genome comprising an exogenous gene of interest, wherein the exogenous gene of interest encodes a human progranulin protein; and wherein the human progranulin protein is encoded by the nucleotide sequence of SEQ ID NO: 4. Further provided herein is an insect cell infected by the recombinant baculovirus disclosed herein.

One or more additional populations of rBV vectors may each comprise an expression cassette encoding AAV Rep protein and/or AAV Cap protein. An AAV Rep expression cassette expresses AAV replicase. An AAV Cap expression cassette expresses the AAV viral structural proteins (VP1, VP2, VP3), also referred to as capsid proteins. In some embodiments, the AAV Cap expression cassette expresses AAV9 structural proteins. In some embodiments, the AAV Cap expression cassette expresses AAV1, AAV2, AAV3, AAV4, AAV5, AAV6, AAV7, AAV8, AAV10 or AAV11 structural proteins, or variants of any of these structural proteins.

Methods for Producing Compositions Comprising Recombinant Adeno-Associated Virus In some aspects, a method disclosed herein for producing a composition comprising rAAV comprises upstream processes and downstream processes. In some embodiments, upstream processes comprise insect cell expansion, rBV seed stock generation, co-infection of insect cells with two rBVs, infected cell lysis, clarification of lysate and tangential flow filtration (TFF1) concentration and diafiltration. In some embodiments, downstream processes comprise AAV affinity purification, chromatography, tangential flow filtration (TFF2) and sterile filtration.

Provided herein is a method for producing a cellular lysate, the method comprising: (i) obtaining a bioreactor containing insect cells suspended in a mixture comprising two or more serum free, and/or protein free insect cell culture medias; (ii) infecting the insect cells with a first population of Baculovirus vectors at a multiplicity of infection (MOI) of between about 1.0 and 2.0, wherein the first population of Baculovirus vectors comprise an expression cassette encoding a gene product of interest; (iii) infecting the insect cells with one or more additional populations of Baculovirus vectors at a MOI of between about 1.0 and 2.0, wherein the additional populations each comprise an expression cassette encoding AAV Rep protein and/or AAV Cap protein; (iv) culturing the infected insect cells under conditions under which the infected insect cells produce rAAV particles encoding the gene of interest; and (v) lysing the infected insect cells to produce a cellular lysate comprising the rAAV particles.

In some embodiments, the two or more serum free and/or protein free insect culture medias are selected from 4Cell Insect CD Medium, ESF-921, ESF-AF, ExpiSf CD Medium, Express Five SFM, baculoGROW, IS SF, and SF900 II SFM. In some embodiments, the mixture comprises between about 10% v/v and 50% v/v SF900 II SFM media.

In some embodiments, the insect cells are obtained after 4-6 passages of a master seed train. In some embodiments, the infection of step (ii) and the infection of step (iii) occur simultaneously.

In some embodiments, the insect cells are present in the bioreactor at a cell density of between 8E+06 viable cells per mL (vc/mL) to about 20E+06 vc/mL.

In some embodiments, the culturing of step (iv) occurs for between 1 day and 5 days.

In some embodiments, the lysing of step (v) comprises contacting the infected insect cells with a detergent.

In some embodiments, a method for producing a cellular lysate further comprises a step of clarifying the cellular lysate by depth filtration.

In some embodiments, a method for producing a cellular lysate further comprises a step of concentrating the rAAV particles in the lysate by tangential flow filtration and/or diafiltration.

In some embodiments, the cellular lysate comprises (a) from about 1E+11 viral genomes per milliliter (vg/mL) to about 1.0E+13 vg/mL; (b) from about 2E+11 vg/mL to about 1.0E+13 vg/mL; or (c) from about 5E+11 vg/mL to about 1.0E+13 vg/mL.

Further provided herein is a method for producing a therapeutic composition, the method comprising: (i) obtaining a cellular lysate comprising rAAV particles; (ii) contacting an affinity chromatography column with the cellular lysate, wherein the affinity column comprises a binding agent specific for a capsid protein of the rAAV particles under conditions under which the rAAV particles bind to the affinity chromatography column; (iii) eluting the bound rAAV particles from the column thereby producing a first eluate, (iv) performing anion-exchange chromatography on the first eluate to produce a second eluate, wherein the second eluate comprises fewer empty rAAV particles than the first eluate; (v) concentrating the second eluate by performing tangential flow filtration using a flow buffer comprising Tris, $MgCl_2$, NaCl, and Poloxamer 188, thereby producing a therapeutic composition comprising rAAV particles.

In some embodiments, the binding agent comprises an affinity resin specific for AAV9 capsid protein.

In some embodiments, the anion-exchange chromatography comprises mixing the first eluate with an equilibration buffer to produce a mixture having a conductivity of between about 0.5 mS/cm to 5 mS/cm, optionally wherein the mixture has a conductivity of 2 mS/cm, binding the mixture to a quaternary amine-containing resin to bind the rAAV particles in the mixture to the resin, and eluting the rAAV particles from the resin to produce the second eluate.

In some embodiments, the second eluate is concentrated to from about 1.0E+12 vg/mL to about 1E+14 vg/mL. In some embodiments, the second eluate is concentrated to from about 1.0E+13 vg/mL to about 5E+13 vg/mL.

In some embodiments, compositions comprising recombinant adeno-associated virus is produced by the method described in Example 2 (see below).

In some embodiments, a composition (e.g., a bulk drug substance) produced by a method disclosed herein comprises at least about 80%, at least about 85%, at least about 90%, or at least about 95% full rAAV particles. In some aspects, a composition produced by a method disclosed herein comprises less that about 15%, less than about 10%, or less than about 5% empty rAAV particles. Methods for assaying for empty AAV particles and full AAV particles are known in the art. See, e.g., Grimm et al. (1999) *Gene Therapy* 6:1322-1330; Sommer et al. (2003) *Mol. Ther.* 7:122-128.

In some embodiments of the methods disclosed herein, the AAV Cap expression cassette expresses AAV1, AAV2, AAV3, AAV4, AAV5, AAV6, AAV7, AAV8, AAV9, AAV10 or AAV11 structural proteins, or variants of such structural proteins. AAV9 is described in U.S. Pat. No. 7,198,951 and in Gao el al. (2004) *J. Virol.* 78:6381-6388, each of which is hereby incorporated by reference in its entirety.

In some embodiments of the methods disclosed herein, the exogenous gene of interest is human GBA1 or human PGRN. In some embodiments of the methods disclosed herein, the exogenous gene of interest encodes a human glucocerebrosidase protein or a human progranulin protein. In some embodiments of the methods disclosed herein, the human glucocerebrosidase protein is encoded by the nucleotide sequence of SEQ ID NO: 2. In some embodiments of the methods disclosed herein, the human progranulin protein is encoded by the nucleotide sequence of SEQ ID NO: 4. In some embodiments of the methods disclosed herein, the exogenous gene of interest encodes an amino acid sequence of SEQ ID NO: 1 or SEQ ID NO: 3.

In some embodiments of the methods disclosed herein, the exogenous gene of interest is human PSAP, human C9orf72, human TREM2, human ApoE2 or human parkin. In some embodiments of the methods disclosed herein, the exogenous gene of interest is a polynucleotide encoding an inhibitory RNA. In some embodiments, the inhibitory RNA targets human α-synuclein, human ATXN2, human MAPT, or human ApoE. Examples of suitable polynucleotide sequences for use in the methods disclosed herein are disclosed in WO2019/070891, WO2019/070893, WO2019/070894, and WO2019/084068, the disclosure of each of which is incorporated by reference herein in its entirety.

Further provided herein is a composition produced by any of the methods disclosed herein.

Process and Release Tests for Compositions Comprising Recombinant Adeno-Associated Virus The rAAV compositions produced by the methods described herein, as well as material produced during intermediate steps of the methods, may be tested for one or more of: safety, identity, titer, purity, impurities, physicochemical properties, biologic properties and extractable volume (volume in container).

Tests that assess safety may include: sterility (United States Pharmacopeia (USP) <71>), bacteriostasis/fungistasis (USP <71>), endotoxin, mycoplasma (USP <63>), in vitro adventious virus, in vivo assay for viral contaminant, rcAAV and container closure.

Tests that assess identity may include: ELISA for specific AAV serotype capsid proteins, western blot assay for rAAV analysis and DNA isolation for exogenous gene of interest (transgene) sequence.

Tests that assess titer may include: physical titer (qPCR), infectious titer, TCID50 and physical titer:infectous titer ratio.

Tests that assess purity and impurities may include: SDS PAGE/silver stain assay for rAAV analysis, Triton X-100, benzonase by ELISA, baculovirus contamination by qPCR, TEM (full/empty ratio), Sf9 host cell DNA, Sf9 Host Cell Protein (ELISA) and detection of Rhabdovirus.

Tests that assess physicochemical properties and biologic properties may include: bioactivity transgene expression (potency), osmolality for cGMP samples, pH for quality control samples, appearance, Sub Visible Particulate Matter (USP<787>), Dynamic Light Scattering and total protein (micro BCA).

Provided herein is an assay that measures the titer of rAAV (e.g. AAV9) encoding GCase by using qPCR (see, Example 11). Contaminating material (e.g., non-encapsulated DNA) is removed during the assay. In an initial step, DNase is used to remove non-encapsulated DNA. Then, proteinase is added to release the AAV capsid prior to performing the qPCR. The assay uses AAV9-GBA1 specific primers and probes (Forward primer, GAC TGT GGG ATC CGT TCG AA (SEQ ID NO: 6); Reverse primer, GAT TGA CAC CCG GCT CAG A (SEQ ID NO: 7); TaqMan probe, 6FAM-CCA TGG AAT TCA GCA GCC CCA GC (SEQ ID NO: 8)-TAMRA) to amplify the region of interest in the vector, which is then quantified using qPCR.

Also provided herein is an assay that measures in vitro potency for rAAV (e.g. AAV9) encoding GCase (see, Example 12). The assay is performed in a 96-well format. HEK293 cells are plated at 20,000 cells/well and transduced the following day with AAV9-GBA1 at different concentrations for both the test article and the reference standard. In some embodiments, the reference standard is a purified rAAV encoding GCase, whose potency was previously determined. Cells are lysed at 72 hours post transduction. GCase activity is assessed in these lysates using the fluorogenic substrate resorufin-β-D-glucopyranoside. In the presence of GCase, this substrate is catalyzed to form the fluorescent product resorufin. Resorufin production is monitored directly as the reaction proceeds to calculate the rate of product formation. In the presence of excess of resorufin-β-D-glucopyranoside substrate (5.3 mM) and under the assayed conditions, the rate of product formation is linearly proportional to the amount of GCase protein. For each GCase activity assay, a standard curve of purified recombinant GCase (rGBA, 0 to 333 ng/ml, R&D cat #7410-GHB-020, >95% purity) is run in parallel to the test samples. An assay acceptance criteria $R^2 \geq 0.96$ for the linear regression of this curve is set to ensure that the enzymatic rate measured correlates to the level of GCase protein. The reported value of the relative potency to the reference standard is calculated using parallel line analysis.

Also provided herein is an that assay measures the titer of rAAV (e.g., AAV9) encoding PGRN by using qPCR or ddPCR (see, Example 13). Contaminating material (e.g., non-encapsulated DNA) is removed during the assay. In an initial step, DNase is used to remove non-encapsulated DNA. Then, proteinase is added to release the AAV capsid prior to performing the qPCR or dd PCR. The assay uses AAV9-GRN specific primers and probes (Forward primer, 5'-GTCTTCCACGACTGTGGGAT-3' (SEQ ID NO: 9); Reverse primer, 5'-GTCAGGGCCACCCAGCTC-3' (SEQ ID NO: 10); TaqMan probe, 5'-FAM-CCGGTTGAGCCACCATGTGGACCC (SEQ ID NO: 11)-TAMRA-3') to amplify the region of interest in the vector, which is then quantified using qPCR or ddPCR.

Further provided herein is an assay that measures in vitro potency for rAAV (e.g. AAV9) encoding PGRN. The assay is performed in a 96-well format. HEK293 cells are plated at 20,000 cells/well and transduced the following day with AAV9-GRN at different drug concentrations for both the test article and the reference standard. At 72-h post transduction, PGRN levels are measured by ELISA (AdipoGen Life Sciences CAT # AG-45A-0018YEK-KI01). The reported value of the relative potency to the reference standard is calculated using parallel line analysis.

All publications, patents and patent applications are herein incorporated by reference in their entirety to the same extent as if each individual publication, patent or patent application was specifically and individually indicated to be incorporated by reference in its entirety The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention.

EXAMPLES

Example 1

Insect cells are thawed and seeded in a first serum- and/or protein-free insect cell culture medium (e.g., 4Cell Insect CD Medium, ESF-921, ESF AF, ExpiSf CD Medium, Express Five SFM, baculoGROW, IS SF, and SF900 II SFM), at more than 3.0E+05 viable cell/ml (passage 1, P1) to establish the seed culture. Cells in the seed culture are cultured for 4-6 passages, and then seeded into the main bioreaction of rAAV production.

During the main bioreaction, the seed culture above is moved into the N-2 culture vessel by mixing 2 L of the seed culture with the first insect cell media at density of about 4.0E+05 to 6.0E+05 cells/ml to a total volume of 10 L. The cells are cultured in the N-2 culture vessel for 96 hours to reach a culture density of more than 5.5E+06 vc/mL with more than 90% viable cells. Subsequently, 10 L of the cells in the N-2 culture are moved to N-1 culture vessel, and mixed with the first insect cell media at a starting cell density of about 5.0E+05 to 1.5E+06 vc/mL. The N-1 culture also contains 0.1%-0.3% (v/v) of Poloxamer-188 solution. The total volume in the N-1 culture vessel is brought to 50 L by adding more of the first insect culture medium. Antifoam agent can be added to the culture as needed. The cells are cultured for 72 hours to reach an end density of more than 5.5E+06 vc/ml with more than 90% viable cells.

In preparation for rBV infection, N-1 culture is mixed with a second serum- and/or protein-free insect cell culture medium (e.g., 4Cell Insect CD Medium, ESF-921, ESF AF, ExpiSf CD Medium, Express Five SFM, baculoGROW, IS SF, and SF900 II SFM), and supplemented with antifoam agent and 0.1%-0.3% (v/v) Poloxamer-188 solution. The first insect cell media is added to the mixture to reach a total desired volume. The ratio of the first insect cell media in the mixture at this stage is between about 30% and 70%. The starting cell density is between about 1.00E+06 and 2.00E+06 vc/mL. The cells are cultured for 96 hours to reach a cell density at between 1.00E+07 to 2.00E+07 vc/mL. The cells are then infected with rBV encoding Rep/AAV9 Cap and rBV encoding the target gene (e.g., GBA, PGRN, PSAP, TREM2, or APOE) at a multiplicity of infection of between about 1 infectious units (IFU)/cell to 2 IFU/cell for each rBV. The volume of each of the rBV added to the culture is between about 5 and 26 L depending on the viral titer. Once the rBVs are added to the culture, the total volume of the culture is adjusted using the second insect cell media such that the percentage of the first insect cell media in the mixture is between 10% and 50% (v/v). Between 15 and 25 hours post infection, the culture is supplemented with Production Boost Additive (PBA) at between about 3% and 8% (v/v). The cells are harvested about 72 to 120 hours after infection.

For the harvest, the insect cells are lysed in Tris buffer with between about 0.2% and 0.8% (w/v) of Triton. Cells are incubated in lysis buffer for about 30 minutes to about 90 minutes. The cell lysate is treated with benzonase at a concentration about 42 IU/mL to 60 IU/mL in the presence of about 1.5 to 2.5 mM $MgCl_2$ for about 45 min to 75 min. The reaction is quenched by about 100 mM to 300 mM of NaCl. The cell lysate contains rAAV packaged by the infected insect cells.

The resulting cell lysate is then subjected to clarification steps. The primary clarification is performed by depth filtration using Millistak+® HC Pod Depth Filter, D0HC media series, 1.1 $m^2$ surface area (POD DOHC) at flushing flowrate of about 12-20 L/min, and a maximum pressure 8-14 psi. The cell lysate is further clarified by depth filtration using Millistak+® HC Pod Depth Filter, A1HC media series, 0.11 $m^2$ surface area (POD A1HC) at flushing flowrate of about 8-15 L/min, and a pressure 8-14 psi. Subsequently, the lysate is conditioned and chased using the first insect culture medium, which yields between about 75% and 95% of the cell lysate before the clarification step. The cell lysate is concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.1% Pluronic, and has a pH of between about 7.5 and 8.5. DF buffer flush step is performed at concentration factor of 3-8. The yield after concentration is between about 60% and about 80% of the lysate before TFF.

The concentrated cell lysate is sterile filtered by diafiltration using Opticap XL10 filters. The cell lysate yield after filtration is between 80% and 98% of the cell lysate before sterile filtration. The cell lysate can be frozen and stored at −80° C. In some embodiments, the cell lysate is thawed and tested for bioburden.

Before chromatography purification for rAAVs, the cell lysate is thawed and filtered using Sartopore 2 membrane. The filter is pre-flushed and equilibrated with an affinity purification equilibration buffer. The filtration is performed at max pressure of 14.00 psi with a flow rate of 750 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of between about 2.00E+13 and 9.00E+13 vg/mL. The total binding capacity of the capsid specific affinity purification resin is between about 1.00E+13 and about 1.00E+14 vg/mL. The column is injected with water for injection (WFI), and acid-stripped with 0.06-0.12 M phosphoric acid. The column is then regenerated using 80-120 mM Tris and 1.8-2.2 M NaCl. After regeneration, the column is equilibrated using the affinity purification equilibration buffer that contains about 0.8-1.5 mM Citric Acid, 12-22 mM Phosphate, 300-400 mM NaCl, 0.2%-0.8% Sucrose, 0.06% to 0.2% F-68. The cell lysate is loaded to the column after equilibration, and the column is equilibrated with again after loading. High salt wash is performed by using a wash buffer, which contains about 0.8-1.5 mM Citric Acid, 12-22 mM Phosphate, 800-1500 mM NaCl, 0.2%-0.8% Sucrose, 0.06% to 0.2% F-68. After the high salt wash, the column is equilibrated with the affinity purification equilibration buffer before elution. The affinity purification chromatography elution buffer contains 10-18 mM Citric Acid, 300-400 mM NaCl, 0.2%-0.8% Sucrose, 0.06% to 0.2% F-68 at pH of 2.2 to 2.8. Collection of eluted rAAV starts at elution peak of about more than 30 mAU at A280. After elution, the column is acid stripped, and regenerated. 4-9 M of Guanidine hydrochloride is used to clean the column at a linear flow rate of between about 45 and 70 cm/h. The column is then washed with water for injection and storage buffer, which contains 1 mM Citric Acid, 18 mM phosphate, 20% Ethanol at a linear flow rate of 45-70 cm/h. The buffers and sample described above are loaded to the column with a linear flow rate of between about 120 and 180 cm/h unless otherwise specified. The eluted fraction is then neutralized using a phosphate buffer which contains 0.25-0.6 M phosphate at a pH of 8.2 to 9.5. The target pH of the eluted fraction after neutralization is 6.8-8.

In preparation for anion exchange chromatography, the sample from the neutralized eluted fraction after affinity chromatography is filtered using Kleenpak filter, and diluted and equilibrated using an anion exchange chromatography equilibration buffer, which contains 12-22 mM Bis-Tris Propane, 0.001% to 0.01% F-68 at pH 9.0-9.5, and a conductivity of between 0.5 and 3 mS/cm. The loading density of the column was between about 1.0+E13 and 4.0+E13 vg/ml. Prior to dilution of the eluted fraction, the anion exchange chromatography column is prepared by the following steps: (i) wash with water for injection, (ii) sanitize with a buffer having 0.8-1.5 M NaOH and 1.5-2.2 M NaCl, (iii) wash with water for injection again, (iv) flush with anion exchange chromatography elution buffer, which contains 16-24 mM Bis-Tris Propane, 0.8-1.5 M NaCl, 0.001% to 0.01% F-68, and (v) equilibrate with the anion exchange chromatography equilibration buffer, which contains 12-22 mM Bis-Tris Propane, 0.001% to 0.01% F-68. Once the anion exchange chromatography column is equilibrated, the sample is loaded onto the column with a loading pH of between about 9.0 and 9.5, and a loading conductivity of between 0.5 and 3 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 3 mAU at A280, and ends at elution peak of about less than 20 mAU. The eluted fraction from anion exchange chromatography is then neutralized using a CIM QA neutralization buffer, which contains 0.2-1 M Tris/HCL at pH of about 5.8 to 6.8. The buffers and samples during anion exchange chromatography are loaded to the column at a volumetric flow rate of between 1.2 L/min and 2.5 L/min unless otherwise specified.

After neutralization, the sample is concentrated by tangential flow filtration, and ultrafiltration/diafiltration with a load density of about 1.0E+17 to 2.0E+17 vg/$m^2$ viral particles. The buffer used in the filtrations contains Tris, $MgCl_2$, NaCl, and Poloxamer 188.

The filtered sample contains purified rAAV particles and is stored in BDS storage at −80° C. The BDS stock contains rAAV particles at about 2.5E+13 to 4.5E+13 vg/mL, and can be diluted to DP concentration of more than 1E+13 vg/mL. The samples are sterile filtered before packaging.

Example 2

Insect cells were thawed and seeded in SF900 II SFM, at more than 3.0E+05 viable cell/ml (passage 1, P1) to establish the seed culture. Cells in the seed culture were cultured for 5 passages, and then seeded into the main bioreaction of rAAV production.

During the main bioreaction, the seed culture above was moved into the N-2 culture vessel by mixing 2 L of the seed culture with SF900 II SFM at density of about 5.0E+05 cells/mL to a total volume of 10 L. The cells were cultured in the N-2 culture vessel for 96 hours to reach a culture density of more than 5.5E+06 vc/mL with more than 90% viable cells. Subsequently, 10 L of the cells in the N-2 culture were moved to N-1 culture vessel, and mixed with SF-900 II SFM at a starting cell density of about 1.0E+06 vc/mL. The N-1 culture also contained 0.1% (v/v) of Poloxamer-188 solution. The total volume in the N-1 culture vessel was brought up to 50 L by adding more of the SF900 II SFM. Antifoam agent can be added to the culture as needed. The cells were cultured for 72 hours to reach an end density of more than 5.5E+06 vc/mL with more than 90% viable cells.

In preparation for rBV infection, N-1 culture was mixed with ESF AF medium, and supplemented with antifoam agent and 0.1% (v/v) Poloxamer-188 solution. SF900 II SFM medium was added to the mixture to reach a total desired volume. The ratio of SF900 II SFM in the mixture at this stage was about 60% (v/v). The starting cell density was about 1.50E+06. The cells were cultured for 96 hours to reach a cell density at 1.50E+07. The cells were then infected with rBV encoding Rep/AAV9 Cap and rBV encoding the target gene (e.g., GBA, PGRN, PSAP, TREM2, or APOE) at a multiplicity of infection of about 1.5 infectious units (IFU)/cell for each rBV. The volume of each of the rBV added to the culture was between about 5 and 26 L depending on the viral titer. Once the rBVs were added to the culture, the total volume of the culture was adjusted using ESF AF medium such that the percentage of SF900 II SFM in the mixture was 40% (v/v). About 20 hours post infection, the culture was supplemented with Production Boost Additive (PBA) at about 5% (v/v). The cells were harvested about 72 hours after infection.

At harvest, the insect cells were lysed in Tris buffer with 0.5% (w/v) of Triton. Cells were incubated in lysis buffer for about 60 minutes. The cell lysate was treated with benzonase at a concentration about 50 IU/mL in the presence of about 2 mM $MgCl_2$ for about 60 min. The reaction was quenched by about 240 mM of NaCl. The cell lysate contained rAAV packaged by the infected insect cells.

The resulting cell lysate was then subjected to clarification steps. The primary clarification was performed by depth filtration using Millistak+® HC Pod Depth Filter, D0HC media series, 6×1.1 $m^2$ surface area (POD DOHC) at flushing flowrate of about 18 L/min, and a maximum pressure less than 14 psi. The cell lysate was further clarified by depth filtration using Millistak+® HC Pod Depth Filter, A1HC media series, 3×1.1 $m^2$ surface area (POD A1HC) at flushing flowrate of about 11 L/min, and a pressure of less than 14 psi. Subsequently, the lysate was conditioned and chased using SF900 II SFM, which yields about 80% of the cell lysate before the clarification step. The cell lysate was concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.0. DF buffer flush step was performed at concentration factor of 6. The yield after concentration was about 90% of the lysate before TFF.

The concentrated cell lysate was sterile filtered by diafiltration using Opticap XL10 filters. The cell lysate yield after filtration was about 95% of the cell lysate before sterile filtration. The cell lysate can be frozen and stored at −80° C.

Before chromatography purification for rAAVs, the cell lysate was thawed and filtered using Sartopore 2 membrane. The filter was pre-flushed and equilibrated with an affinity purification equilibration buffer. The filtration was performed at max pressure of 14.00 psi with a flow rate of 750 mL/min. After filtration, the filter was again flushed with the affinity purification equilibration buffer. In order to purify the rAAV, affinity purification was followed by anion exchange purification.

A capsid specific affinity purification column was used for affinity purification of the rAAVs. The capsid specific affinity purification resin had a load capacity of about 3.0 to 9.0E+13 vg/mL. The total binding capacity of the capsid specific affinity purification resin was about 4.2E+17 vg. The column was injected with water for injection (WFI), and acid-stripped with 0.1 M phosphoric acid. The column was then regenerated using 100 mM Tris and 2 M NaCl. After regeneration, the column was equilibrated using the affinity purification equilibration buffer that contains about 1 mM Citric Acid, 18 mM Phosphate, 350 mM NaCl, 0.5% Sucrose, 0.1% F-68. The cell lysate was loaded to the column after equilibration, and the column was equilibrated with the affinity purification equilibration buffer again after loading. High salt wash was performed by using a wash buffer, which contains about 1 mM Citric Acid, 18 mM Phosphate, 1000 mM NaCl, 0.5% Sucrose, 0.1% F-68. After the high salt wash, the column was equilibrated with the affinity purification equilibration buffer before elution. The affinity purification chromatography elution buffer contains 14 mM Citric Acid, 350 mM NaCl, 0.5% Sucrose, 0.1% F-68 at pH of 2.5. Collection of eluted rAAV started at elution peak of about more than 50 mAU at A280. After elution, the column was acid stripped, and regenerated. 6 M of Guanidine hydrochloride was used to clean the column at a linear flow rate of about 60 cm/h. The column was then washed with water for injection and storage buffer, which contains 1 mM Citric Acid, 18 mM phosphate, 20% Ethanol at a linear flow rate of 60 cm/h. The buffers and sample described above were loaded to the column with a linear flow rate of about 150 cm/h unless otherwise specified. The eluted fraction was then neutralized using a phosphate buffer that contains 0.4 M phosphate at a pH of 9. The target pH of the eluted fraction after neutralization was 6.8-8.

In preparation for anion exchange chromatography, the sample from the neutralized eluted fraction after affinity chromatography was filtered using Kleenpak filter, and diluted and equilibrated using an anion exchange chromatography equilibration buffer, which contains 20 mM Bis-Tris Propane, 0.001% F-68 at pH 9.2, and a conductivity of less than 2.1 mS/cm. The loading density of the column was between about 1.0+E13 and 4.0+E13 vg/mL. Prior to dilution of the eluted fraction, the anion exchange chromatography column was prepared by the following steps: (i) wash with water for injection, (ii) sanitize with a buffer having 1 M NaOH and 2 M NaCl, (iii) wash with water for injection again, (iv) flush with anion exchange chromatography elution buffer, which contains 20 mM Bis-Tris Propane, 1 M NaCl, 0.001% F-68, and (v) equilibrate with the anion exchange chromatography equilibration buffer, which contains 20 mM Bis-Tris Propane, 0.001% F-68. Once the anion exchange chromatography column was equilibrated, the sample was loaded onto the column with CIMQ buffer having pH of about 9.3, and a loading conductivity of less than 2 mS/cm. After loading, the column was washed again with the anion exchange chromatography equilibration buffer. The sample was eluted first with an anion exchange chromatography equilibration buffer and then the anion exchange chromatography elution buffer. The collection of the fraction containing the rAAV started at elution peak of about 15 mAU. The eluted fraction from anion exchange chromatography was then neutralized using a CIM QA neutralization buffer, which contains 0.5 M Tris/HCL at pH of about 6.5. The buffers and samples during anion exchange chromatography were loaded to the column at a volumetric flow rate of 2 L/min unless otherwise specified.

After neutralization, the sample was concentrated by TFF, and ultrafiltration/diafiltration with a load density of about 1.3E+17 vg/m$^2$ viral particles. The buffer used in the filtrations contains Tris, $MgCl_2$, NaCl, and Poloxamer 188.

The filtered sample contained purified rAAV particles and was stored in BDS storage at −80° C. The BDS stock contained rAAV particles at about 4.0E+13 vg/mL, and can be diluted to DP concentration of more than 3.0E+13 vg/mL. The samples were sterile filtered before packaging.

Example 3

Insect cells are thawed and seeded in 4Cell Insect CD Medium, at more than 3.0E+05 viable cell/mL (passage 1, P1) to establish the seed culture. Cells in the seed culture are cultured for 3 passages, and then seeded into the main bioreaction of rAAV production.

During the main bioreaction, the seed culture above is moved into the N-2 culture vessel by mixing 2 L of the seed culture with 4Cell Insect CD Medium at density of about 3.0E+05 cells/mL to a total volume of 10 L. The cells are cultured in the N-2 culture vessel for 96 hours to reach a culture density of more than 5.5E+06 vc/mL with more than 85% viable cells. Subsequently, 10 L of the cells in the N-2 culture are moved to N-1 culture vessel, and mixed with 4Cell Insect CD Medium at a starting cell density of about 1.0E+06 vc/mL. The N-1 culture also contained 9% (v/v) of Poloxamer-188 solution. The total volume in the N-1 culture vessel is brought up to 50 L by adding more of the 4Cell Insect CD Medium. Antifoam agent can be added to the culture as needed. The cells are cultured for 72 hours to reach an end density of more than 5.5E+06 vc/mL with more than 85% viable cells.

In preparation for rBV infection, N-1 culture is mixed with ExpiSf CD Medium, and supplemented with antifoam agent and 9% (v/v) Poloxamer-188 solution. 4Cell Insect CD Medium is added to the mixture to reach a total desired volume. The ratio of 4Cell Insect CD Medium in the mixture at this stage is about 45% (v/v). The starting cell density is about 1.20E+06. The cells are cultured for 96 hours to reach a cell density at 1.20E+07. The cells are then infected with rBV encoding Rep/AAV9 Cap and rBV encoding the target gene (e.g., GBA, PGRN, PSAP, TREM2, or APOE) at a multiplicity of infection of about 1 infectious units (IFU)/cell for each rBV. The volume of each of the rBV added to the culture is between about 5 and 26 L depending on the viral titer. Once the rBVs are added to the culture, the total volume of the culture is adjusted using ExpiSf CD Medium such that the percentage of 4Cell Insect CD Medium in the mixture is 40% (v/v). About 25 hours post infection, the culture is supplemented with Production Boost Additive (PBA) at about 5% (v/v). The cells are harvested about 96 hours after infection.

At harvest, the insect cells are lysed in Tris buffer with 0.5% (w/v) of Triton. Cells are incubated in lysis buffer for about 60 minutes. The cell lysate is treated with benzonase at a concentration about 30 IU/mL in the presence of about 2.5 mM $MgCl_2$ for about 60 min. The reaction is quenched by about 300 mM of NaCl. The cell lysate contains rAAV packaged by the infected insect cells.

The resulting cell lysate is then subjected to clarification steps. The primary clarification is performed by depth filtration using Millistak+® HC Pod Depth Filter, D0HC media series, 1.1 m2 surface area (POD DOHC) at flushing flowrate of about 12 L/min, and a maximum pressure of less than 12 psi. The cell lysate is further clarified by depth filtration using Millistak+® HC Pod Depth Filter, A1HC media series, 0.11 m$^2$ surface area (POD A1HC) at flushing flowrate of about 9 L/min, and a pressure of less than 12 psi. Subsequently, the lysate is conditioned and chased using 4Cell Insect CD Medium, which yields about 85% of the cell lysate before the clarification step. The cell lysate is concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.5. DF buffer flush step is performed at concentration factor of 5. The yield after concentration is about 80% of the lysate before TFF.

The concentrated cell lysate is sterile filtered by diafiltration using Opticap XL10 filters. The cell lysate yield after filtration is about 90% of the cell lysate before sterile filtration. The cell lysate can be frozen and stored at −80° C.

Before chromatography purification for rAAVs, the cell lysate is thawed and filtered using Sartopore 2 membrane. The filter is pre-flushed and equilibrated with an affinity purification equilibration buffer. The filtration is performed at max pressure of 12.00 psi with a flow rate of 780 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of about 3.0E+13 vg/mL. The total binding capacity of the capsid specific affinity purification resin is about 1.20E+17. The column is injected with water for injection (WFI), and acid-stripped with 0.1 M phosphoric acid. The column is then regenerated using 85 mM Tris and 2 M NaCl. After regeneration, the column is equilibrated using the affinity purification equilibration buffer which contains about 1.2 mM Citric Acid, 15 mM Phosphate, 300 mM NaCl, 0.2% Sucrose, 0.08% F-68. The cell lysate is loaded to the column after equilibration, and the column is equilibrated with the affinity purification equilibration buffer again after loading. High salt wash is performed by using a wash buffer, which contains about 1.2 mM Citric Acid, 15 mM Phosphate, 800 mM NaCl, 0.2% Sucrose, 0.08% F-68. After the high salt wash, the column is equilibrated with the affinity purification equilibration buffer before elution. The affinity purification chromatography elution buffer contains 10 mM Citric Acid, 300 mM NaCl, 0.2% Sucrose, 0.08% F-68 at pH of 2.2. Collection of eluted rAAV starts at elution peak of about more than 30 mAU at A280. After elution, the column is acid stripped, and regenerated. 4 M of Guanidine hydrochloride is used to clean the column at a linear flow rate of about 60 cm/h. The column is then washed with water for injection and storage buffer, which contains 1.2 mM Citric Acid, 15 mM phosphate, 20% Ethanol at a linear flow rate of 60 cm/h. The buffers and sample described above are loaded to the column with a linear flow rate of about 120 cm/h unless otherwise specified. The eluted fraction is then neutralized using a phosphate buffer which contains 0.25 M phosphate at a pH of 8.8. The target pH of the eluted fraction after neutralization is 7.5.

In preparation for anion exchange chromatography, the sample from the neutralized eluted fraction after affinity chromatography is filtered using Kleenpak filter, and diluted and equilibrated using an anion exchange chromatography equilibration buffer, which contains 12 mM Bis-Tris Propane, 0.001% F-68 at pH 9.0, and a conductivity of less than 2.5 mS/cm. The loading density of the column was between about 1.0+E13 and 4.0+E13 vg/mL. Prior to dilution of the eluted fraction, the anion exchange chromatography column is prepared by the following steps: (i) wash with water for injection, (ii) sanitize with a buffer having 0.8 M NaOH and 2 M NaCl, (iii) wash with water for injection again, (iv) flush with anion exchange chromatography elution buffer, which contains 16 mM Bis-Tris Propane, 0.8 M NaCl, 0.0008% F-68, and (v) equilibrate with the anion exchange chromatography equilibration buffer, which contains 20 mM Bis-Tris Propane, 0.001% F-68. Once the anion exchange chromatography column is equilibrated, the sample is loaded onto the column with a loading pH of about 9.0, and a loading conductivity of 2.3 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 6 mAU at A280, and ends at elution peak of about less than 20 mAU. The eluted fraction from anion exchange chromatography is then neutralized using a CIM QA neutralization buffer, which contains 0.4 M Tris/HCL at pH of about 6.0. The buffers and samples during anion exchange chromatography are loaded to the column at a volumetric flow rate of 1.5 L/min unless otherwise specified.

After neutralization, the sample is concentrated by tangential flow filtration, and ultrafiltration/diafiltration with a load density of about 1.42E+17 vg/$m^2$ viral particles. The buffer used in the filtrations contains Tris, $MgCl_2$, NaCl, and Poloxamer 188.

The filtered sample contains purified rAAV particles and is stored in BDS storage at −80° C. The BDS stock contains rAAV particles at about 3.0E+13 vg/mL, and can be diluted to DP concentration of more than 1.0E+13 vg/mL. The samples are sterile filtered before packaging.

Example 4

Insect cells are thawed and seeded in ESF AF medium, at more than 3.0E+05 viable cell/mL (passage 1, P1) to establish the seed culture. Cells in the seed culture are cultured for 4 passages, and then seeded into the main bioreaction of rAAV production.

During the main bioreaction, the seed culture above is moved into the N-2 culture vessel by mixing 2 L of the seed culture with ESF AF medium at density of about 4.0E+05 cells/mL to a total volume of 10 L. The cells are cultured in the N-2 culture vessel for 96 hours to reach a culture density of more than 6.2E+06 vc/mL with more than 93% viable cells. Subsequently, 10 L of the cells in the N-2 culture are moved to N-1 culture vessel, and mixed with ESF AF medium at a starting cell density of about 1.0E+06 vc/mL. The N-1 culture also contains 10% (v/v) of Poloxamer-188 solution. The total volume in the N-1 culture vessel is brought up to 50 L by adding more of the ESF AF medium. Antifoam agent can be added to the culture as needed. The cells are cultured for 72 hours to reach an end density of more than 6E+06 vc/mL with more than 90% viable cells.

In preparation for rBV infection, N-1 culture is mixed with ExpiSf CD Medium, and supplemented with antifoam agent and 10% (v/v) Poloxamer-188 solution. ESF AF medium is added to the mixture to reach a total desired volume. The ratio of ESF AF medium in the mixture at this stage is about 50% (v/v). The starting cell density is about 1.80E+06. The cells are cultured for 96 hours to reach a cell density at 1.80E+07. The cells are then infected with rBV encoding Rep/AAV9 Cap and rBV encoding the target gene (e.g., GBA, PGRN, PSAP, TREM2, or APOE) at a multiplicity of infection of about 1.8 infectious units (IFU)/cell for each rBV. The volume of each of the rBV added to the culture is between about 5 and 26 L depending on the viral titer. Once the rBVs are added to the culture, the total volume of the culture is adjusted using ExpiSf CD Medium such that the percentage of ESF AF medium in the mixture is 40% (v/v). About 25 hours post infection, the culture is supplemented with Production Boost Additive (PBA) at about 7% (v/v). The cells are harvested about 84 hours after infection.

At harvest, the insect cells are lysed in Tris buffer with 0.5% (w/v) of Triton. Cells are incubated in lysis buffer for about 45 minutes. The cell lysate is treated with benzonase at a concentration about 30 IU/m L in the presence of about 2.2 mM $MgCl_2$ for about 60 min. The reaction is quenched by about 300 mM of NaCl. The cell lysate contains rAAV packaged by the infected insect cells.

The resulting cell lysate is then subjected to clarification steps. The primary clarification is performed by depth filtration using Millistak+® HC Pod Depth Filter, D0HC media series, 1.1 $m^2$ surface area (POD DOHC) at flushing flowrate of about 14 L/min, and a maximum pressure of about 10 psi. The cell lysate is further clarified by depth filtration using Millistak+® HC Pod Depth Filter, A1HC media series, 0.11 $m^2$ surface area (POD A1HC) at flushing flowrate of about 10 L/min, and a pressure of about 10 psi. Subsequently, the lysate is conditioned and chased using ESF AF medium, which yields about 85% of the cell lysate before the clarification step. The cell lysate is concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.0. DF buffer flush step is performed at concentration factor of 5. The yield after concentration is about 80% of the lysate before TFF.

The concentrated cell lysate is sterile filtered by diafiltration using Opticap XL10 filters. The cell lysate yield after filtration is about 95% of the cell lysate before sterile filtration. The cell lysate can be frozen and stored at −80° C.

Before chromatography purification for rAAVs, the cell lysate is thawed and filtered using Sartopore 2 membrane. The filter is pre-flushed and equilibrated with an affinity purification equilibration buffer. The filtration is performed at about 10.00 psi with a flow rate of 780 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of about 3.2E+13 vg/mL. The total binding capacity of the capsid specific affinity purification resin is about 1.50E+17. The column is injected with water for injection (WFI), and acid-stripped with 0.08 M phosphoric acid. The column is then regenerated using 85 mM Tris and 1.8 M NaCl. After regeneration, the column is equilibrated using the affinity purification equilibration buffer which contains about 1.2 mM Citric Acid, 18 mM Phosphate, 380 mM NaCl, 0.5% Sucrose, 0.08% F-68. The cell lysate is loaded to the column after equilibration, and the column is equilibrated with the affinity purification equilibration buffer again after loading. High salt wash is performed by using a wash buffer, which contains about 1.2 mM Citric Acid, 18 mM Phosphate, 800 mM NaCl, 0.5% Sucrose, 0.08% F-68. After the high salt wash, the column is equilibrated with the affinity purification equilibration buffer before elution. The affinity purification chromatography elution buffer contains 15 mM Citric Acid, 380 mM NaCl, 0.5% Sucrose, 0.08% F-68 at pH of 2.5. Collection of eluted rAAV starts at elution peak of about more than 60 mAU at A280. After elution, the column is acid stripped, and regenerated. 6 M of Guanidine hydrochloride is used to clean the column at a linear flow rate of about 45 cm/h. The column is then washed with water for injection and storage buffer, which contains 1.2 mM Citric Acid, 18 mM phosphate, 20% Ethanol at a linear flow rate of 60 cm/h. The buffers and sample described above are loaded to the column with a linear flow rate of about 150 cm/h unless otherwise specified. The eluted fraction is then neutralized using a phosphate buffer which contains 0.4 M phosphate at a pH of 8.8. The target pH of the eluted fraction after neutralization is 7.2.

In preparation for anion exchange chromatography, the sample from the neutralized eluted fraction after affinity chromatography is filtered using Kleenpak filter, and diluted and equilibrated using an anion exchange chromatography equilibration buffer, which contains 18 mM Bis-Tris Propane, 0.001% F-68 at pH 9.0, and a conductivity of less than 1.8 mS/cm. The loading density of the column was between about 1.0+E13 and 4.0+E13 vg/mL. Prior to dilution of the eluted fraction, the anion exchange chromatography column is prepared by the following steps: (i) wash with water for injection, (ii) sanitize with a buffer having 0.8 M NaOH and 2 M NaCl, (iii) wash with water for injection again, (iv) flush with anion exchange chromatography elution buffer, which contains 18 mM Bis-Tris Propane, 1 M NaCl, 0.001% F-68, and (v) equilibrate with the anion exchange chromatography equilibration buffer, which contains 18 mM Bis-Tris Propane, 0.001% F-68. Once the anion exchange chromatography column is equilibrated, the sample is loaded onto the column with a loading pH of about 9.0, and a loading conductivity of 2.1 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 4 mAU at A280, and ends at elution peak of about less than 15 mAU. The eluted fraction from anion exchange chromatography is then neutralized using a CIM QA neutralization buffer, which contains 0.6 M Tris/HCL at pH of about 6.0. The buffers and samples during anion exchange chromatography are loaded to the column at a volumetric flow rate of 2 L/min unless otherwise specified.

After neutralization, the sample is concentrated by tangential flow filtration, and ultrafiltration/diafiltration with a load density of about 1.42E+17 vg/$m^2$ viral particles. The buffer used in the filtrations contains Tris, $MgCl_2$, NaCl, and Poloxamer 188.

The filtered sample contains purified rAAV particles and was stored in BDS storage at −80° C. The BDS stock contains rAAV particles at about 3.0E+13 vg/mL, and can be diluted to DP concentration of more than 1.0E+13 vg/mL. The samples are sterile filtered before packaging.

Example 5

Insect cells are thawed and seeded in Express Five SFM, at more than 3.0E+05 viable cell/mL (passage 1, P1) to establish the seed culture. Cells in the seed culture are cultured for 5 passages, and then seeded into the main bioreaction of rAAV production.

During the main bioreaction, the seed culture above is moved into the N-2 culture vessel by mixing 2 L of the seed culture with Express Five SFM at density of about 5.0E+05 cells/m L to a total volume of 10 L. The cells are cultured in the N-2 culture vessel for 96 hours to reach a culture density of more than 6E+06 vc/mL with more than 90% viable cells. Subsequently, 10 L of the cells in the N-2 culture are moved to N-1 culture vessel, and mixed with Express Five SFM at a starting cell density of about 1.2E+06 vc/mL. The N-1 culture also contains 12% (v/v) of Poloxamer-188 solution. The total volume in the N-1 culture vessel is brought up to 50 L by adding more of the Express Five SFM. Antifoam agent can be added to the culture as needed. The cells are cultured for 72 hours to reach an end density of more than 6E+06 vc/mL with more than 90% viable cells.

In preparation for rBV infection, N-1 culture is mixed with IS SF Medium, and supplemented with antifoam agent and 12% (v/v) Poloxamer-188 solution. Express Five SFM is added to the mixture to reach a total desired volume. The ratio of Express Five SFM in the mixture at this stage is about 50% (v/v). The starting cell density is about 1.50E+06. The cells are cultured for 96 hours to reach a cell density at 1.80E+07. The cells are then infected with rBV encoding Rep/AAV9 Cap and rBV encoding the target gene (e.g., GBA, PGRN, PSAP, TREM2, or APOE) at a multiplicity of infection of about 1.5 infectious units (IFU)/cell for each rBV. The volume of each of the rBV added to the culture is between about 5 and 26 L depending on the viral titer. Once the rBVs are added to the culture, the total volume of the culture is adjusted using IS SF Medium such that the percentage of Express Five SFM in the mixture is 40% (v/v). About 48 hours post infection, the culture is supplemented with Production Boost Additive (PBA) at about 5% (v/v). The cells are harvested about 72 hours after infection.

At harvest, the insect cells are lysed in Tris buffer with 0.8% (w/v) of Triton. Cells are incubated in lysis buffer for about 60 minutes. The cell lysate is treated with benzonase at a concentration about 45 IU/mL in the presence of about 2.2 mM $MgCl_2$ for about 60 min. The reaction is quenched by about 300 mM of NaCl. The cell lysate contains rAAV packaged by the infected insect cells.

The resulting cell lysate is then subjected to clarification steps. The primary clarification is performed by depth filtration using Millistak+® HC Pod Depth Filter, D0HC media series, 1.1 $m^2$ surface area (POD DOHC) at flushing flowrate of about 13 L/min, and a maximum pressure of about 14 psi. The cell lysate is further clarified by depth filtration using Millistak+® HC Pod Depth Filter, A1HC media series, 0.11 $m^2$ surface area (POD A1HC) at flushing flowrate of about 11 L/min, and a pressure of about 14 psi. Subsequently, the lysate is conditioned and chased using Express Five SFM, which yields about 85% of the cell lysate before the clarification step. The cell lysate is concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.5. DF buffer flush step is performed at concentration factor of 4. The yield after concentration is about 90% of the lysate before TFF.

The concentrated cell lysate is sterile filtered by diafiltration using Opticap XL10 filters. The cell lysate yield after filtration is about 95% of the cell lysate before sterile filtration. The cell lysate can be frozen and stored at −80° C.

Before chromatography purification for rAAVs, the cell lysate is thawed and filtered using Sartopore 2 membrane. The filter is pre-flushed and equilibrated with an affinity purification equilibration buffer. The filtration is performed at about 14.00 psi with a flow rate of 700 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of about 3.4E+13 vg/mL. The total binding capacity of the capsid specific affinity purification resin is about 1.50E+17. The column is injected with water for injection (WFI), and acid-stripped with 0.08 M phosphoric acid. The column is then regenerated using 120 mM Tris and 2.2 M NaCl. After regeneration, the column is equilibrated using the affinity purification equilibration buffer which contains about 1.2 mM Citric Acid, 15 mM Phosphate, 300 mM NaCl, 0.5% Sucrose, 0.1% F-68. The cell lysate is loaded to the column after equilibration, and the column is equilibrated with the affinity purification equilibration buffer again after loading. High salt wash is performed by using a wash buffer, which contains about 1.2 mM Citric Acid, 15 mM Phosphate, 800 mM NaCl, 0.5% Sucrose, 0.1% F-68. After the high salt wash, the column is equilibrated with the affinity purification equilibration buffer before elution. The affinity purification chromatography elution buffer contains 18 mM Citric Acid, 300 mM NaCl, 0.5% Sucrose, 0.1% F-68 at pH of 2.6. Collection of eluted rAAV starts at elution peak of about more than 60 mAU at A280. After elution, the column is acid stripped, and regenerated. 5 M of Guanidine hydrochloride is used to clean the column at a linear flow rate of about 55 cm/h. The column is then washed with water for injection and storage buffer, which contains 1.2 mM Citric Acid, 15 mM phosphate, 20% Ethanol at a linear flow rate of 55 cm/h. The buffers and sample described above are loaded to the column with a linear flow rate of about 175 cm/h unless otherwise specified. The eluted fraction is then neutralized using a phosphate buffer which contains 0.6 M phosphate at a pH of 8.5. The target pH of the eluted fraction after neutralization is 7.

In preparation for anion exchange chromatography, the sample from the neutralized eluted fraction after affinity chromatography is filtered using Kleenpak filter, and diluted and equilibrated using an anion exchange chromatography equilibration buffer, which contains 20 mM Bis-Tris Propane, 0.0012% F-68 at pH 9.3, and a conductivity of less than 2.5 mS/cm. The loading density of the column was between about 1.0+E13 and 4.0+E13 vg/mL. Prior to dilution of the eluted fraction, the anion exchange chromatography column is prepared by the following steps: (i) wash with water for injection, (ii) sanitize with a buffer having 1 M NaOH and 1.5 M NaCl, (iii) wash with water for injection again, (iv) flush with anion exchange chromatography elution buffer, which contains 20 mM Bis-Tris Propane, 0.8 M NaCl, 0.001% F-68, and (v) equilibrate with the anion exchange chromatography equilibration buffer, which contains 20 mM Bis-Tris Propane, 0.001% F-68. Once the anion exchange chromatography column is equilibrated, the sample is loaded onto the column with a loading pH of about 9.3, and a loading conductivity of 1.8 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 5 mAU at A280, and ends at elution peak of about less than 20 mAU. The eluted fraction from anion exchange chromatography is then neutralized using a CIM QA neutralization buffer, which contains 1 M Tris/HCL at pH of about 6.5. The buffers and samples during anion exchange chromatography are loaded to the column at a volumetric flow rate of 1.5 L/min unless otherwise specified.

After neutralization, the sample is concentrated by TFF, and ultrafiltration/diafiltration with a load density of about 1.37E+17 vg/$m^2$ viral particles. The buffer used in the filtrations contains Tris, $MgCl_2$, NaCl, and Poloxamer 188.

The filtered sample contains purified rAAV particles and is stored in BDS storage at −80° C. The BDS stock contains rAAV particles at about 1E+13 vg/mL, and can be diluted to DP concentration of more than 1.0E+13 vg/mL. The samples are sterile filtered before packaging.

Example 6

Insect cells are thawed and seeded in Express Five SFM, at more than 3.0E+05 viable cell/mL (passage 1, P1) to establish the seed culture. Cells in the seed culture are cultured for 6 passages, and then seeded into the main bioreaction of rAAV production.

During the main bioreaction, the seed culture above is moved into the N-2 culture vessel by mixing 2 L of the seed culture with Express Five SFM at density of about 4.0E+05 cells/mL to a total volume of 10 L. The cells are cultured in the N-2 culture vessel for 96 hours to reach a culture density of more than 5.5E+06 vc/mL with more than 90% viable cells. Subsequently, 10 L of the cells in the N-2 culture are moved to N-1 culture vessel, and mixed with Express Five SFM at a starting cell density of about 1.5E+06 vc/mL. The N-1 culture also contains 10% (v/v) of Poloxamer-188 solution. The total volume in the N-1 culture vessel is brought up to 50 L by adding more of the Express Five SFM. Antifoam agent can be added to the culture as needed. The cells are cultured for 72 hours to reach an end density of more than 6E+06 vc/mL with more than 90% viable cells.

In preparation for rBV infection, N-1 culture is mixed with SF900 II SFM, and supplemented with antifoam agent and 10% (v/v) Poloxamer-188 solution. Express Five SFM is added to the mixture to reach a total desired volume. The ratio of Express Five SFM in the mixture at this stage was about 50% (v/v). The starting cell density is about 2E+06. The cells are cultured for 96 hours to reach a cell density at 2E+07. The cells are then infected with rBV encoding Rep/AAV9 Cap and rBV encoding the target gene (e.g., GBA, PGRN, PSAP, TREM2, or APOE) at a multiplicity of infection of about 1 infectious units (IFU)/cell for each rBV. The volume of each of the rBV added to the culture is between about 5 and 26 L depending on the viral titer. Once the rBVs are added to the culture, the total volume of the culture is adjusted using SF900 II SFM such that the percentage of Express Five SFM in the mixture is 40% (v/v). About 36 hours post infection, the culture is supplemented with Production Boost Additive (PBA) at about 8% (v/v). The cells are harvested about 72 hours after infection.

At harvest, the insect cells are lysed in Tris buffer with 0.5% (w/v) of Triton. Cells are incubated in lysis buffer for about 75 minutes. The cell lysate is treated with benzonase at a concentration about 60 IU/mL in the presence of about 2 mM $MgCl_2$ for about 60 min. The reaction is quenched by about 200 mM of NaCl. The cell lysate contains rAAV packaged by the infected insect cells.

The resulting cell lysate is then subjected to clarification steps. The primary clarification is performed by depth filtration using Millistak+® HC Pod Depth Filter, D0HC media series, 1.1 $m^2$ surface area (POD DOHC) at flushing flowrate of about 12 L/min, and a maximum pressure of about 11 psi. The cell lysate is further clarified by depth filtration using Millistak+® HC Pod Depth Filter, A1HC media series, 0.11 $m^2$ surface area (POD A1HC) at flushing flowrate of about 11 L/min, and a pressure of about 11 psi. Subsequently, the lysate is conditioned and chased using Express Five SFM, which yields about 80% of the cell lysate before the clarification step. The cell lysate is concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.0. DF buffer flush step was performed at concentration factor of 6. The yield after concentration is about 90% of the lysate before TFF.

The concentrated cell lysate is sterile filtered by diafiltration using Opticap XL10 filters. The cell lysate yield after filtration is about 95% of the cell lysate before sterile filtration. The cell lysate can be frozen and stored at −80° C.

Before chromatography purification for rAAVs, the cell lysate is thawed and filtered using Sartopore 2 membrane. The filter is pre-flushed and equilibrated with an affinity purification equilibration buffer. The filtration is performed at about 11.00 psi with a flow rate of 720 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of about 4E+13 vg/mL. The total binding capacity of the capsid specific affinity purification resin is about 1.50E+17. The column is injected with water for injection (WFI), and acid-stripped with 0.12 M phosphoric acid. The column is then regenerated using 100 mM Tris and 1.8 M NaCl. After regeneration, the column is equilibrated using the affinity purification equilibration buffer which contains about 1 mM Citric Acid, 20 mM Phosphate, 400 mM NaCl, 0.5% Sucrose, 0.1% F-68. The cell lysate is loaded to the column after equilibration, and the column is equilibrated with the affinity purification equilibration buffer again after loading. High salt wash is performed by using a wash buffer, which contains about 1 mM Citric Acid, 20 mM Phosphate, 800 mM NaCl, 0.5% Sucrose, 0.1% F-68. After the high salt wash, the column is equilibrated with the affinity purification equilibration buffer before elution. The affinity purification chromatography elution buffer contains 14 mM Citric Acid, 400 mM NaCl, 0.5% Sucrose, 0.1% F-68 at pH of 2.5. Collection of eluted rAAV starts at elution peak of about more than 40 mAU at A280. After elution, the column is acid stripped, and regenerated. 5 M of Guanidine hydrochloride is used to clean the column at a linear flow rate of about 70 cm/h. The column is then washed with water for injection and storage buffer, which contains 1 mM Citric Acid, 20 mM phosphate, 20% Ethanol at a linear flow rate of 70 cm/h. The buffers and sample described above are loaded to the column with a linear flow rate of about 150 cm/h unless otherwise specified. The eluted fraction is then neutralized using a phosphate buffer which contains 0.3 M phosphate at a pH of 9.0. The target pH of the eluted fraction after neutralization is 7.5.

In preparation for anion exchange chromatography, the sample from the neutralized eluted fraction after affinity chromatography is filtered using Kleenpak filter, and diluted and equilibrated using an anion exchange chromatography equilibration buffer, which contains 12 mM Bis-Tris Propane, 0.0012% F-68 at pH 8.8, and a conductivity of less than 2 mS/cm. The loading density of the column was between about 1.0+E13 and 4.0+E13 vg/mL. Prior to dilution of the eluted fraction, the anion exchange chromatography column is prepared by the following steps: (i) wash with water for injection, (ii) sanitize with a buffer having 1.2 M NaOH and 1.8 M NaCl, (iii) wash with water for injection again, (iv) flush with anion exchange chromatography elution buffer, which contains 12 mM Bis-Tris Propane, 1.5 M NaCl, 0.001% F-68, and (v) equilibrate with the anion exchange chromatography equilibration buffer, which contains 12 mM Bis-Tris Propane, 0.0012% F-68. Once the anion exchange chromatography column is equilibrated, the sample is loaded onto the column with a loading pH of about 8.8, and a loading conductivity of 2.5 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 5 mAU at A280, and ends at elution peak of about less than 18 mAU. The eluted fraction from anion exchange chromatography is then neutralized using a CIM QA neutralization buffer, which contains 0.8 M Tris/HCL at pH of about 5.8. The buffers and samples during anion exchange chromatography are loaded to the column at a volumetric flow rate of 1.5 L/min unless otherwise specified.

After neutralization, the sample is concentrated by tangential flow filtration, and ultrafiltration/diafiltration with a load density of about 1.4E+17 vg/$m^2$ viral particles. The buffer used in the filtrations contains Tris, $MgCl_2$, NaCl, and Poloxamer 188.

The filtered sample contains purified rAAV particles and is stored in BDS storage at −80° C. The BDS stock contains rAAV particles at about 1E+13 vg/mL, and can be diluted to DP concentration of more than 1.0E+13 vg/mL. The samples are sterile filtered before packaging.

Example 7

Insect cells are thawed and seeded in ESF-921, at more than 3.0E+05 viable cell/mL (passage 1, P1) to establish the seed culture. Cells in the seed culture are cultured for 4 passages, and then seeded into the main bioreaction of rAAV production.

During the main bioreaction, the seed culture above is moved into the N-2 culture vessel by mixing 2 L of the seed culture with ESF-921 at density of about 3.0E+05 cells/mL to a total volume of 10 L. The cells are cultured in the N-2 culture vessel for 96 hours to reach a culture density of more than 5.5E+06 vc/mL with more than 80% viable cells. Subsequently, 10 L of the cells in the N-2 culture are moved to N-1 culture vessel, and mixed with ESF-921 at a starting cell density of about 1.5E+06 vc/mL. The N-1 culture also contains 10% (v/v) of Poloxamer-188 solution. The total volume in the N-1 culture vessel is brought up to 50 L by adding more of the ESF-921. Antifoam agent can be added to the culture as needed. The cells are cultured for 72 hours to reach an end density of more than 6.5E+06 vc/mL with more than 80% viable cells.

In preparation for rBV infection, N-1 culture is mixed with baculoGROW, and supplemented with antifoam agent and 10% (v/v) Poloxamer-188 solution. ESF-921 is added to the mixture to reach a total desired volume. The ratio of ESF-921 in the mixture at this stage is about 40% (v/v). The starting cell density is about 2E+06. The cells are cultured for 96 hours to reach a cell density at 1.5E+07. The cells are then infected with rBV encoding Rep/AAV9 Cap and rBV encoding the target gene (e.g., GBA, PGRN, PSAP, TREM2, or APOE) at a multiplicity of infection of about 2 infectious units (IFU)/cell for each rBV. The volume of each of the rBV added to the culture is between about 5 and 26 L depending on the viral titer. Once the rBVs are added to the culture, the total volume of the culture is adjusted using baculoGROW such that the percentage of ESF-921 in the mixture is 40% (v/v). About 24 hours post infection, the culture is supplemented with Production Boost Additive (PBA) at about 5% (v/v). The cells are harvested about 96 hours after infection.

At harvest, the insect cells are lysed in Tris buffer with 0.5% (w/v) of Triton. Cells are incubated in lysis buffer for about 75 minutes. The cell lysate is treated with benzonase at a concentration about 60 IU/mL in the presence of about 2 mM $MgCl_2$ for about 60 min. The reaction is quenched by about 200 mM of NaCl. The cell lysate contains rAAV packaged by the infected insect cells.

The resulting cell lysate is then subjected to clarification steps. The primary clarification is performed by depth filtration using Millistak+® HC Pod Depth Filter, D0HC media series, 1.1 $m^2$ surface area (POD DOHC) at flushing flowrate of about 12 L/min, and a maximum pressure of about 14 psi. The cell lysate is further clarified by depth filtration using Millistak+® HC Pod Depth Filter, A1HC media series, 0.11 $m^2$ surface area (POD A1HC) at flushing flowrate of about 12 L/min, and a pressure of about 14 psi. Subsequently, the lysate is conditioned and chased using ESF-921, which yields about 80% of the cell lysate before the clarification step. The cell lysate is concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.0. DF buffer flush step is performed at concentration factor of 8. The yield after concentration is about 80% of the lysate before TFF.

The concentrated cell lysate is sterile filtered by diafiltration using Opticap XL10 filters. The cell lysate yield after filtration is about 90% of the cell lysate before sterile filtration. The cell lysate can be frozen and stored at −80° C.

Before chromatography purification for rAAVs, the cell lysate is thawed and filtered using Sartopore 2 membrane. The filter was pre-flushed and equilibrated with an affinity purification equilibration buffer. The filtration is performed at about 14.00 psi with a flow rate of 750 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of about 3E+13 vg/mL. The total binding capacity of the capsid specific affinity purification resin is about 1.60E+17. The column is injected with water for injection (WFI), and acid-stripped with 0.12 M phosphoric acid. The column is then regenerated using 120 mM Tris and 1.8 M NaCl. After regeneration, the column is equilibrated using the affinity purification equilibration buffer which contains about 1.2 mM Citric Acid, 16 mM Phosphate, 350 mM NaCl, 0.4% Sucrose, 0.1% F-68. The cell lysate is loaded to the column after equilibration, and the column is equilibrated with the affinity purification equilibration buffer again after loading. High salt wash is performed by using a wash buffer, which contains about 1.2 mM Citric Acid, 16 mM Phosphate, 1000 mM NaCl, 0.5% Sucrose, 0.1% F-68. After the high salt wash, the column is equilibrated with the affinity purification equilibration buffer before elution. The affinity purification chromatography elution buffer contains 18 mM Citric Acid, 350 mM NaCl, 0.4% Sucrose, 0.1% F-68 at pH of 2.2. Collection of eluted rAAV starts at elution peak of about more than 50 mAU at A280. After elution, the column is acid stripped, and regenerated. 6 M of Guanidine hydrochloride is used to clean the column at a linear flow rate of about 50 cm/h. The column is then washed with water for injection and storage buffer, which contains 1.2 mM Citric Acid, 16 mM phosphate, 20% Ethanol at a linear flow rate of 50 cm/h. The buffers and sample described above are loaded to the column with a linear flow rate of about 130 cm/h unless otherwise specified. The eluted fraction is then neutralized using a phosphate buffer which contains 0.3 M phosphate at a pH of 9.5. The target pH of the eluted fraction after neutralization is 7.5.

In preparation for anion exchange chromatography, the sample from the neutralized eluted fraction after affinity chromatography is filtered using Kleenpak filter, and diluted and equilibrated using an anion exchange chromatography equilibration buffer, which contains 18 mM Bis-Tris Propane, 0.0012% F-68 at pH 9.2, and a conductivity of less than 3 mS/cm. The loading density of the column was between about 1.0+E13 and 4.0+E13 vg/mL. Prior to dilution of the eluted fraction, the anion exchange chromatography column is prepared by the following steps: (i) wash with water for injection, (ii) sanitize with a buffer having 1 M NaOH and 1.8 M NaCl, (iii) wash with water for injection again, (iv) flush with anion exchange chromatography elution buffer, which contains 18 mM Bis-Tris Propane, 1 M NaCl, 0.001% F-68, and (v) equilibrate with the anion exchange chromatography equilibration buffer, which contains 18 mM Bis-Tris Propane, 0.001% F-68. Once the anion exchange chromatography column is equilibrated, the sample is loaded onto the column with a loading pH of about 9.2, and a loading conductivity of 3 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 5 mAU at A280, and ends at elution peak of about less than 18 mAU. The eluted fraction from anion exchange chromatography is then neutralized using a CIM QA neutralization buffer, which contains 0.8 M Tris/HCL at pH of about 5.8. The buffers and samples during anion exchange chromatography are loaded to the column at a volumetric flow rate of 1.5 L/min unless otherwise specified.

After neutralization, the sample is concentrated by tangential flow filtration, and ultrafiltration/diafiltration with a load density of about 1.4E+17 vg/$m^2$ viral particles. The buffer used in the filtrations contains Tris, $MgCl_2$, NaCl, and Poloxamer 188.

The filtered sample contains purified rAAV particles and is stored in BDS storage at −80° C. The BDS stock contains rAAV particles at about 1E+13 vg/mL, and can be diluted to DP concentration of more than 1.0E+13 vg/mL. The samples are sterile filtered before packaging.

Example 8

Insect cells are thawed and seeded in baculoGROW, at more than 3.0E+05 viable cell/mL (passage 1, P1) to establish the seed culture. Cells in the seed culture are cultured for 6 passages, and then seeded into the main bioreaction of rAAV production.

During the main bioreaction, the seed culture above is moved into the N-2 culture vessel by mixing 2 L of the seed culture with baculoGROW at density of about 3.0E+05 cells/mL to a total volume of 10 L. The cells are cultured in the N-2 culture vessel for 96 hours to reach a culture density of more than 5.5E+06 vc/mL with more than 90% viable cells. Subsequently, 10 L of the cells in the N-2 culture are moved to N-1 culture vessel, and mixed with baculoGROW at a starting cell density of about 1.5E+06 vc/m L. The N-1 culture also contains 5% (v/v) of Poloxamer-188 solution. The total volume in the N-1 culture vessel is brought up to 50 L by adding more of the baculoGROW. Antifoam agent can be added to the culture as needed. The cells are cultured for 72 hours to reach an end density of more than 6.5E+06 vc/mL with more than 90% viable cells.

In preparation for rBV infection, N-1 culture is mixed with ESF AF, and supplemented with antifoam agent and 5% (v/v) Poloxamer-188 solution. baculoGROW is added to the mixture to reach a total desired volume. The ratio of baculoGROW in the mixture at this stage is about 30% (v/v). The starting cell density is about 2E+06. The cells are cultured for 96 hours to reach a cell density at 1.5E+07. The cells are then infected with rBV encoding Rep/AAV9 Cap and rBV encoding the target gene (e.g., GBA, PGRN, PSAP, TREM2, or APOE) at a multiplicity of infection of about 1.8 infectious units (IFU)/cell for each rBV. The volume of each of the rBV added to the culture is between about 5 and 26 L depending on the viral titer. Once the rBVs are added to the culture, the total volume of the culture is adjusted using ESF AF such that the percentage of baculoGROW in the mixture is 40% (v/v). About 36 hours post infection, the culture is supplemented with Production Boost Additive (PBA) at about 8% (v/v). The cells are harvested about 120 hours after infection.

At harvest, the insect cells are lysed in Tris buffer with 0.8% (w/v) of Triton. Cells are incubated in lysis buffer for about 60 minutes. The cell lysate is treated with benzonase at a concentration about 60 IU/ml in the presence of about 2.5 mM $MgCl_2$ for about 60 min. The reaction is quenched by about 280 mM of NaCl. The cell lysate contains rAAV packaged by the infected insect cells.

The resulting cell lysate is then subjected to clarification steps. The primary clarification is performed by depth filtration using Millistak+® HC Pod Depth Filter, DOHC media series, 1.1 $m^2$ surface area (POD DOHC) at flushing flowrate of about 15 L/min, and a maximum pressure of about less than 12 psi. The cell lysate is further clarified by depth filtration using Millistak+® HC Pod Depth Filter, A1HC media series, 0.11 $m^2$ surface area (POD A1HC) at flushing flowrate of about 15 L/min, and a pressure of about less than 12 psi. Subsequently, the lysate is conditioned and chased using baculoGROW, which yields about 85% of the cell lysate before the clarification step. The cell lysate is concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.0. DF buffer flush step is performed at concentration factor of 3. The yield after concentration is about 75% of the lysate before TFF.

The concentrated cell lysate is sterile filtered by diafiltration using Opticap XL10 filters. The cell lysate yield after filtration is about 80% of the cell lysate before sterile filtration. The cell lysate can be frozen and stored at −80° C.

Before chromatography purification for rAAVs, the cell lysate is thawed and filtered using Sartopore 2 membrane. The filter is pre-flushed and equilibrated with an affinity purification equilibration buffer. The filtration is performed at about less than 12.00 psi with a flow rate of 780 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of about 2.5E+13 vg/mL. The total binding capacity of the capsid specific affinity purification resin is about 1E+17. The column is injected with water for injection (WFI), and acid-stripped with 0.12 M phosphoric acid. The column is then regenerated using 100 mM Tris and 1.8 M NaCl. After regeneration, the column is equilibrated using the affinity purification equilibration buffer that contains about 1 mM Citric Acid, 22 mM Phosphate, 320 mM NaCl, 0.5% Sucrose, 0.1% F-68. The cell lysate is loaded to the column after equilibration, and the column is equilibrated with the affinity purification equilibration buffer again after loading. High salt wash is performed by using a wash buffer, which contains about 1 mM Citric Acid, 22 mM Phosphate, 1000 mM NaCl, 0.5% Sucrose, 0.1% F-68. After the high salt wash, the column is equilibrated with the affinity purification equilibration buffer before elution. The affinity purification chromatography elution buffer contains 15 mM Citric Acid, 320 mM NaCl, 0.5% Sucrose, 0.1% F-68 at pH of 2.5. Collection of eluted rAAV starts at elution peak of about more than 50 mAU at A280. After elution, the column is acid stripped, and regenerated. 6 M of Guanidine hydrochloride is used to clean the column at a linear flow rate of about 60 cm/h. The column is then washed with water for injection and storage buffer, which contains 1 mM Citric Acid, 22 mM phosphate, 20% Ethanol at a linear flow rate of 70 cm/h. The buffers and sample described above are loaded to the column with a linear flow rate of about 150 cm/h unless otherwise specified. The eluted fraction is then neutralized using a phosphate buffer which contains 0.5 M phosphate at a pH of 8.5. The target pH of the eluted fraction after neutralization is 7.5.

In preparation for anion exchange chromatography, the sample from the neutralized eluted fraction after affinity chromatography is filtered using Kleenpak filter, and diluted and equilibrated using an anion exchange chromatography equilibration buffer, which contains 22 mM Bis-Tris Propane, 0.001% F-68 at pH 9.2, and a conductivity of less than 3 mS/cm. The loading density of the column was between about 1.0+E13 and 4.0+E13 vg/mL. Prior to dilution of the eluted fraction, the anion exchange chromatography column is prepared by the following steps: (i) wash with water for injection, (ii) sanitize with a buffer having 1 M NaOH and 1.8 M NaCl, (iii) wash with water for injection again, (iv) flush with anion exchange chromatography elution buffer, which contains 22 mM Bis-Tris Propane, 1.8 M NaCl, 0.001% F-68, and (v) equilibrate with the anion exchange chromatography equilibration buffer, which contains 22 mM Bis-Tris Propane, 0.0012% F-68. Once the anion exchange chromatography column is equilibrated, the sample is loaded onto the column with a loading pH of about 9.2, and a loading conductivity of 2 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 5 mAU at A280, and ends at elution peak of about less than 15 mAU. The eluted fraction from anion exchange chromatography is then neutralized using a CIM QA neutralization buffer, which contains 0.5 M Tris/HCL at pH of about 6. The buffers and samples during anion exchange chromatography are loaded to the column at a volumetric flow rate of 1.5 L/min unless otherwise specified.

After neutralization, the sample is concentrated by tangential flow filtration, and ultrafiltration/diafiltration with a load density of about 1.4E+17 vg/$m^2$ viral particles. The buffer used in the filtrations contains Tris, $MgCl_2$, NaCl, and Poloxamer 188.

The filtered sample contains purified rAAV particles and is stored in BDS storage at −80° C. The BDS stock contains rAAV particles at about 1E+13 vg/mL, and can be diluted to DP concentration of more than 1.0E+13 vg/mL. The samples are sterile filtered before packaging.

Example 9

Insect cells are thawed and seeded in ExpiSf CD Medium, at more than 3.0E+05 viable cell/mL (passage 1, P1) to establish the seed culture. Cells in the seed culture are cultured for 5 passages, and then seeded into the main bioreaction of rAAV production.

During the main bioreaction, the seed culture above is moved into the N-2 culture vessel by mixing 2 L of the seed culture with ExpiSf CD Medium at density of about 6.0E+05 cells/mL to a total volume of 10 L. The cells are cultured in the N-2 culture vessel for 96 hours to reach a culture density of more than 6E+06 vc/mL with more than 90% viable cells. Subsequently, 10 L of the cells in the N-2 culture are moved to N-1 culture vessel, and mixed with ExpiSf CD Medium at a starting cell density of about 1.5E+06 vc/mL. The N-1 culture also contains 10% (v/v) of Poloxamer-188 solution. The total volume in the N-1 culture vessel is brought up to 50 L by adding more of the ExpiSf CD Medium. Antifoam agent can be added to the culture as needed. The cells are cultured for 72 hours to reach an end density of more than 6E+06 vc/mL with more than 85% viable cells.

In preparation for recombinant Baculovirus (rBV) infection, N-1 culture is mixed with SF900 II SFM, and supplemented with antifoam agent and 10% (v/v) Poloxamer-188 solution. ExpiSf CD Medium is added to the mixture to reach a total desired volume. The ratio of ExpiSf CD Medium in the mixture at this stage is about 40% (v/v). The starting cell density is about 2E+06. The cells are cultured for 96 hours to reach a cell density at 1.5E+07. The cells are then infected with rBV encoding Rep/AAV9 Cap and rBV encoding the target gene (e.g., GBA, PGRN, PSAP, TREM2, or APOE) at a multiplicity of infection of about 1.6 infectious units (IFU)/cell for each rBV. The volume of each of the rBV added to the culture is between about 5 and 26 L depending on the viral titer. Once the rBVs are added to the culture, the total volume of the culture was adjusted using SF900 II SFM such that the percentage of ExpiSf CD Medium in the mixture is 40% (v/v). About 20 hours post infection, the culture is supplemented with Production Boost Additive (PBA) at about 8% (v/v). The cells are harvested about 60 hours after infection.

At harvest, the insect cells are lysed in Tris buffer with 0.4% (w/v) of Triton. Cells are incubated in lysis buffer for about 75 minutes. The cell lysate is treated with benzonase at a concentration about 50 IU/mL in the presence of about 2.5 mM $MgCl_2$ for about 60 min. The reaction is quenched by about 150 mM of NaCl. The cell lysate contains rAAV packaged by the infected insect cells.

The resulting cell lysate is then subjected to clarification steps. The primary clarification is performed by depth filtration using Millistak+® HC Pod Depth Filter, DOHC media series, 1.1 $m^2$ surface area (POD DOHC) at flushing flowrate of about 15 L/min, and a maximum pressure of about 13 psi. The cell lysate is further clarified by depth filtration using Millistak+® HC Pod Depth Filter, A1HC media series, 0.11 $m^2$ surface area (POD A1HC) at flushing flowrate of about 12 L/min, and a pressure of about 13 psi. Subsequently, the lysate is conditioned and chased using ExpiSf CD Medium, which yields about 95% of the cell lysate before the clarification step. The cell lysate is concentrated by tangential flow filtration (TFF). During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.0. DF buffer flush step is performed at concentration factor of 6. The yield after concentration is about 75% of the lysate before TFF.

The concentrated cell lysate is sterile filtered by diafiltration using Opticap XL10 filters. The cell lysate yield after filtration is about 95% of the cell lysate before sterile filtration. The cell lysate can be frozen and stored at −80° C.

Before chromatography purification for rAAVs, the cell lysate is thawed and filtered using Sartopore 2 membrane. The filter is pre-flushed and equilibrated with an affinity purification equilibration buffer. The filtration is performed at about 13.00 psi with a flow rate of 720 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of about 3.4E+13 vg/mL. The total binding capacity of the capsid specific affinity purification resin is about 1E+17. The column is injected with water for injection (WFI), and acid-stripped with 0.12 M phosphoric acid. The column is then regenerated using 90 mM Tris and 1.8 M NaCl. After regeneration, the column is equilibrated using the affinity purification equilibration buffer which contains about 1.5 mM Citric Acid, 22 mM Phosphate, 360 mM NaCl, 0.5% Sucrose, 0.2% F-68. The cell lysate is loaded to the column after equilibration, and the column is equilibrated with the affinity purification equilibration buffer again after loading. High salt wash is performed by using a wash buffer, which contains about 1.5 mM Citric Acid, 22 mM Phosphate, 1500 mM NaCl, 0.5% Sucrose, 0.1% F-68. After the high salt wash, the column is equilibrated with the affinity purification equilibration buffer before elution. The affinity purification chromatography elution buffer contains 18 mM Citric Acid, 360 mM NaCl, 0.5% Sucrose, 0.2% F-68 at pH of 2.5. Collection of eluted rAAV starts at elution peak of about more than 30 mAU at A280. After elution, the column is acid stripped, and regenerated. 6 M of Guanidine hydrochloride is used to clean the column at a linear flow rate of about 80 cm/h. The column is then washed with water for injection and storage buffer, which contains 1.5 mM Citric Acid, 22 mM phosphate, 20% Ethanol at a linear flow rate of 80 cm/h. The buffers and sample described above are loaded to the column with a linear flow rate of about 120 cm/h unless otherwise specified. The eluted fraction is then neutralized using a phosphate buffer which contains 0.5 M phosphate at a pH of 8.5. The target pH of the eluted fraction after neutralization is 6.8.

In preparation for anion exchange chromatography, the sample from the neutralized eluted fraction after affinity chromatography is filtered using Kleenpak filter, and diluted and equilibrated using an anion exchange chromatography equilibration buffer, which contains 20 mM Bis-Tris Propane, 0.001% F-68 at pH 8.8, and a conductivity of less than 2.5 mS/cm. The loading density of the column was between about 1.0+E13 and 4.0+E13 vg/mL. Prior to dilution of the eluted fraction, the anion exchange chromatography column is prepared by the following steps: (i) wash with water for injection, (ii) sanitize with a buffer having 1 M NaOH and 1.8 M NaCl, (iii) wash with water for injection again, (iv) flush with anion exchange chromatography elution buffer, which contains 20 mM Bis-Tris Propane, 1.8 M NaCl, 0.001% F-68, and (v) equilibrate with the anion exchange chromatography equilibration buffer, which contains 20 mM Bis-Tris Propane, 0.0012% F-68. Once the anion exchange chromatography column is equilibrated, the sample is loaded onto the column with a loading pH of about 8.8, and a loading conductivity of 2.5 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 5 mAU at A280, and ends at elution peak of about less than 15 mAU. The eluted fraction from anion exchange chromatography is then neutralized using a CIM QA neutralization buffer, which contains 1 M Tris/HCL at pH of about 6. The buffers and samples during anion exchange chromatography are loaded to the column at a volumetric flow rate of 1.5 L/min unless otherwise specified.

After neutralization, the sample is concentrated by tangential flow filtration, and ultrafiltration/diafiltration with a load density of about 1.39E+17 vg/m$^2$ viral particles. The buffer used in the filtrations contains Tris, $MgCl_2$, NaCl, and Poloxamer 188.

The filtered sample contains purified rAAV particles and is stored in BDS storage at −80° C. The BDS stock contains rAAV particles at about 3.0E+13 vg/mL, and can be diluted to DP concentration of more than 1.0E+13 vg/mL. The samples are sterile filtered before packaging.

Example 10

Insect cells are thawed and seeded in SF900 II SFM, at more than 3.0E+05 viable cell/mL (passage 1, P1) to establish the seed culture. Cells in the seed culture are cultured for 5 passages, and then seeded into the main bioreaction of rAAV production.

During the main bioreaction, the seed culture above is moved into the N-2 culture vessel by mixing 2 L of the seed culture with SF900 II SFM at density of about 4.8E+05 cells/mL to a total volume of 10 L. The cells are cultured in the N-2 culture vessel for 96 hours to reach a culture density of more than 4.8E+06 vc/mL with more than 90% viable cells. Subsequently, 10 L of the cells in the N-2 culture are moved to N-1 culture vessel, and mixed with SF-900 II SFM at a starting cell density of about 2E+06 vc/mL. The N-1 culture also contained 8% (v/v) of Poloxamer-188 solution. The total volume in the N-1 culture vessel is brought up to 50 L by adding more of the SF900 II SFM. Antifoam agent can be added to the culture as needed. The cells are cultured for 72 hours to reach an end density of more than 6E+06 vc/mL with more than 90% viable cells.

In preparation for rBV infection, N-1 culture is mixed with IS SF, and supplemented with antifoam agent and 8% (v/v) Poloxamer-188 solution. SF900 II SFM is added to the mixture to reach a total desired volume. The ratio of SF900 II SFM in the mixture at this stage was about 45% (v/v). The starting cell density is about 2E+06. The cells are cultured for 96 hours to reach a cell density at 1.5E+07. The cells are then infected with rBV encoding Rep/AAV9 Cap and rBV encoding the target gene (e.g., GBA, PGRN, PSAP, TREM2, or APOE) at a multiplicity of infection of about 1.5 infectious units (IFU)/cell for each rBV. The volume of each of the rBV added to the culture is between about 5 and 26 L depending on the viral titer. Once the rBVs are added to the culture, the total volume of the culture is adjusted using IS SF such that the percentage of SF900 II SFM in the mixture is 40% (v/v). About 18 hours post infection, the culture is supplemented with Production Boost Additive (PBA) at about 8% (v/v). The cells are harvested about 72 hours after infection.

At harvest, the insect cells are lysed in Tris buffer with 0.5% (w/v) of Triton. Cells are incubated in lysis buffer for about 75 minutes. The cell lysate is treated with benzonase at a concentration about 50 IU/mL in the presence of about 2.5 mM $MgCl_2$ for about 60 min. The reaction is quenched by about 280 mM of NaCl. The cell lysate contains rAAV packaged by the infected insect cells.

The resulting cell lysate is then subjected to clarification steps. The primary clarification is performed by depth filtration using Millistak+® HC Pod Depth Filter, DOHC media series, 1.1 $m^2$ surface area (POD DOHC) at flushing flowrate of about 20 L/min, and a maximum pressure of about 11 psi. The cell lysate is further clarified by depth filtration using Millistak+® HC Pod Depth Filter, A1HC media series, 0.11 $m^2$ surface area (POD A1HC) at flushing flowrate of about 20 L/min, and a pressure of about 11 psi. Subsequently, the lysate is conditioned and chased using SF900 II SFM, which yields about 95% of the cell lysate before the clarification step. The cell lysate is concentrated by TFF. During TFF, the cell lysate undergoes water flush, diafiltration buffer (DF buffer) conditioning, DF buffer flush and DF buffer chase. DF buffer contains 20 mM Tris, 500 mM NaCl, and 0.001% Pluronic, and has a pH of 8.0. DF buffer flush step is performed at concentration factor of 6. The yield after concentration is about 90% of the lysate before TFF.

The concentrated cell lysate is sterile filtered by diafiltration using Opticap XL10 filters. The cell lysate yield after filtration is about 95% of the cell lysate before sterile filtration. The cell lysate can be frozen and stored at −80° C.

Before chromatography purification for rAAVs, the cell lysate is thawed and filtered using Sartopore 2 membrane. The filter is pre-flushed and equilibrated with an affinity purification equilibration buffer. The filtration is performed at about 13.00 psi with a flow rate of 750 mL/min. After filtration, the filter is again flushed with the affinity purification equilibration buffer. In order to purify the rAAV, affinity purification is followed by anion exchange purification.

A capsid specific affinity purification column is used for affinity purification of the rAAVs. The capsid specific affinity purification resin has a load capacity of about 4E+13 vg/mL. The total binding capacity of the capsid specific affinity purification resin is about 2E+17. The column is injected with water for injection (WFI), and acid-stripped with 0.06 M phosphoric acid. The column is then regenerated using 100 mM Tris and 1.8 M NaCl. After regeneration, the column is equilibrated using the affinity purification equilibration buffer which contains about 1.2 mM Citric Acid, 20 mM Phosphate, 360 mM NaCl, 0.5% Sucrose, 0.2% F-68. The cell lysate is loaded to the column after equilibration, and the column is equilibrated with the affinity purification equilibration buffer again after loading. High salt wash is performed by using a wash buffer, which contains about 1.2 mM Citric Acid, 20 mM Phosphate, 1200 mM NaCl, 0.5% Sucrose, 0.2% F-68. After the high salt wash, the column is equilibrated with the affinity purification equilibration buffer before elution. The affinity purification chromatography elution buffer contains 20 mM Citric Acid, 360 mM NaCl, 0.5% Sucrose, 0.2% F-68 at pH of 2.2. Collection of eluted rAAV starts at elution peak of about more than 50 mAU at A280. After elution, the column is acid stripped, and regenerated. 4 M of Guanidine hydrochloride is used to clean the column at a linear flow rate of about 75 cm/h. The column is then washed with water for injection and storage buffer, which contains 1.2 mM Citric Acid, 20 mM phosphate, 20% Ethanol at a linear flow rate of 75 cm/h. The buffers and sample described above are loaded to the column with a linear flow rate of about 120 cm/h unless otherwise specified. The eluted fraction is then neutralized using a phosphate buffer which contains 0.4 M phosphate at a pH of 9.0. The target pH of the eluted fraction after neutralization is 7.5.

In preparation for anion exchange chromatography, the sample from the neutralized eluted fraction after affinity chromatography is filtered using Kleenpak filter, and diluted and equilibrated using an anion exchange chromatography equilibration buffer, which contains 18 mM Bis-Tris Propane, 0.0015% F-68 at pH 9, and a conductivity of less than 2 mS/cm. The loading density of the column was between about 1.0+E13 and 4.0+E13 vg/mL. Prior to dilution of the eluted fraction, the anion exchange chromatography column is prepared by the following steps: (i) wash with water for injection, (ii) sanitize with a buffer having 1 M NaOH and 1.2 M NaCl, (iii) wash with water for injection again, (iv) flush with anion exchange chromatography elution buffer, which contains 18 mM Bis-Tris Propane, 1.2 M NaCl, 0.0015% F-68, and (v) equilibrate with the anion exchange chromatography equilibration buffer, which contains 18 mM Bis-Tris Propane, 0.0015% F-68. Once the anion exchange chromatography column is equilibrated, the sample was loaded onto the column with a loading pH of about 9, and a loading conductivity of 2.3 mS/cm. After loading, the column is washed again with the anion exchange chromatography equilibration buffer. The sample is eluted first with an anion exchange chromatography equilibration buffer and then the anion exchange chromatography elution buffer. The collection of the fraction containing the rAAV starts at elution peak of about more than 5 mAU at A280, and ends at elution peak of about less than 15 mAU. The eluted fraction from anion exchange chromatography is then neutralized using a CIM QA neutralization buffer, which contains 0.6 M Tris/HCL at pH of about 6.2. The buffers and samples during anion exchange chromatography are loaded to the column at a volumetric flow rate of 1.5 L/min unless otherwise specified.

After neutralization, the sample is concentrated by TFF, and ultrafiltration/diafiltration with a load density of about 1.8E+17 vg/$m^2$ viral particles. The buffer used in the filtrations contains Tris, $MgCl_2$, NaCl, and Poloxamer 188.

The filtered sample contains purified rAAV particles and is stored in BDS storage at −80° C. The BDS stock contains rAAV particles at about 1.5E+13 vg/mL, and can be diluted to DP concentration of more than 1.0E+13 vg/mL. The samples are sterile filtered before packaging.

Example 11: Quantitative PCR Assay to Measure Physical Titer of rAAV Encoding Glucocerebrosidase The purpose of this assay is to quantify the physical titer of an AAV (e.g., AAV9) encapsulated vector encoding GCase using quantitative PCR (qPCR) by comparison with a known standard. This test method may be used to quantitate physical vector genome titer in purified AAV viral samples or in process production fractions.

Laboratory Test Method

TABLE 1

| Materials | | |
|---|---|---|
| Material Description | Manufacturer | Item Number |
| PerfeCTa qPCR supermix with ROX | QuantaBio | 95051-500 |
| UltraPure distilled water (DIW) | Invitrogen | 10977-023 or equivalent |
| MicroAmp optical 96-well reaction | Applied Biosystems | 43-067-37 |
| OctaPool ™Solution Reservoirs, 25 ml disposable, sterile | Thomas Scientific | 1159X93 or equivalent |
| DNA Away | Fisher Scientific | M0303L or equivalent |
| PCR 8-Well Tube Strips and Caps | VWR | 2017-004 |
| Eppendorf DNA LoBind Microcentrifuge Tubes 1.5 ml | Eppendorf | 022431021 |
| Tween-80 (polysorbate-80) | VWR | JT4117-02 |
| Proteinase K, 20 mg/mL | Promega | MC5005 |
| 20% SDS Solution | Fisher Scientific | BP1311-1 or equivalent |
| 0.5M EDTA pH 8.0 | Fisher Scientific | BP2482 or equivalent |
| TE buffer, pH 8.0 | Fisher Scientific | AM9849 or equivalent |
| Falcon conical tube 15 ml | Fisher Scientific | 14 959 53A or equivalent |
| Falcon conical tube 50 ml | Fisher Scientific | 14 432 22 or equivalent |
| DNase I (RNAse free) | New England BioLabs | M0303S |
| Lambda Hind III digested DNA | New England BioLabs | B7025 |

TABLE 2

| Equipment | | |
|---|---|---|
| Equipment Description | Manufacturer | Item Number |
| QuantStudio ™ 7 Flex | Applied Biosystems | 4485695 |
| Pipette Set LTS Pipet-Lite XLS+ manual (P2, P20, P200, P1000) | Rainin | 30386597 |
| Combination PCR Workstations | AirClean ™ Systems | AC632LFUVC |
| Sorvall ST8R centrifuge | Fisher Scientific | 75 230 395 |
| Myspin 6 mini centrifuge | Fisher Scientific | 75 004 061 or equivalent |
| Mini Vortex Mixer | Fisher Scientific | 400815B or equivalent |
| Simpliamp PCR Thermal Cycler | Thermo Fisher | A24811 or equivalent |

The linearized plasmid encoding GCase was linearized with DraIII. The virus reference standard was a different rAAV vector encoding GCase.

TABLE 3

| Primers | | |
|---|---|---|
| Primer or Probe | Name | Sequence |
| Forward primer | Cov PR001-1_F | GAC TGT GGG ATC CGT TCG AA (SEQ ID NO: 6) |
| Reverse primer | Cov PR001-1_R | GAT TGA CAC CCG GCT CAG A (SEQ ID NO: 7) |
| TaqMan probe | Cov PR001-2 Probe | 6FAM-CCA TGG AAT TCA GCA GCC CCA GC (SEQ ID NO: 8)-TAMRA |

Note:

all primers are assumed to be provided at 100 μM from the vendor and are of HPLC level purity or higher.

Background/Theory of Method: To determine the amount of copies of AAV encapsulating the target sequence, the desired sequence was amplified using PCR using real-time qPCR. In this method, a fluorescent reporter molecule (such as a dye-labeled probe) was used to monitor the progress of the amplification reaction. With each amplification cycle, the increase in fluorescence intensity is proportional to the increase in amplicon concentration, with the qPCR instrument system collecting data for each sample during each PCR cycle. The resulting plots of fluorescence vs. cycle number for all the samples were then set with their background fluorescence at a common starting point. The cycle number at which an amplification plot crosses a predetermined background threshold fluorescence level is called the "Ct" or threshold cycle. By comparing the Ct values from unknowns with a known standard diluted at various concentrations, the starting concentrations of the unknown samples were determined, thereby yielding the desired amount of copies (if present) in a given sample.

Procedure

10% Polysorbate-80, PCR Dilution Buffer, 10× Proteinase K Buffer, and Standard Diluent were prepared. The linearized plasmid was diluted to 2e9 copies/μL if needed. 10-fold serial dilutions were performed in standard diluent using the first standard to prepare a standard curve ranging from $2\times10^7$ copies/μL to 20 copies/μL. A set of standards ($2\times10^7$ to 20 copies/μL) was aliquoted into 7 wells of an 8-well 0.2 mL PCR tube strip such that each strip serves as a single-use standard curve. Primer stock was prepared from lyophilized primer.

Blanks and DNAse control were prepared. Reference standards and samples were prepared. All samples and reference standards were run in triplicate. Sample dilutions for all sample types were selected based on initial concentration based on Table 4. In-process samples may be run at the highest dilution suggested for the theoretical sample concentration below.

TABLE 4

| Sample and reference standard dilution procedure | | |
|---|---|---|
| Theoretical sample concentration (copies/mL) | Method | Dilutions to prepare |
| $<1\times10^{12}$ | qPCR | 1:10 and 1:100 |
| $\geq1\times10^{12}$ | qPCR | 1:100 and 1:1000 |
| Unknown | qPCR | 1:10, 1:100 and 1:1000 |

A DNAse master mix and a Proteinase K master mix were prepared. Samples were treated with DNase and mixed with Proteinase K solution.

qPCR master reaction mix was prepared as detailed in Table 5:

TABLE 5

| qPCR master Reaction Mix Preparation | | | |
|---|---|---|---|
| Component | Stock concentration (μM) | Final concentration (μM) | Volume of stock per reaction (μL) |
| qPCR master Mix | NA | NA | 10 |
| Forward Primer | 10 | 0.5 | 1 |
| Reverse Primer | 10 | 0.5 | 1 |
| Probe | 5 | 0.25 | 1 |
| Template or sample | Variable | | 5 |
| DIW | NA | NA | 2.0 |
| | | | 20 μL (total) |

qPCR was run using the following settings with the maximum ramp rate:

TABLE 6

| qPCR Conditions | | | |
|---|---|---|---|
| Stage | Temperature | Time (mm:ss) | Cycles |
| 1 | 95° C. | 5:00 | 1 |
| | 95° C. | 0:15 | |
| 2 | 60° C. | 1:00 | 45 |
| 3 | 4° C. | Hold | 1 |

The final copy number was determined as follows:

a. The amplification of the target amplicon based on fluorescence from all samples in the assay plate was recorded, and the Ct value is determined automatically by the QuantStudio™ software.
b. A standard curve was prepared by plotting Ct of each standard vs. the number of copies per reaction on a logarithmic scale (the final graph is semi-log with the y-axis being linear and x-axis being on a log 10 scale). This was fit to a straight line.
c. Vector copy numbers in each reaction well were determined by interpolating Ct values with the standard curve determined in (b) and were to be included in the data exported from the instrument.
d. Finally, the number determined in (c) above was multiplied by the dilution factors employed to prepare the samples to yield the final copy number. If 2 or more dilutions were used on a sample, all valid values in the standard curve were averaged after calculations.

If the Ct value lies above the linear range of the standard curve for qPCR, samples can be re-prepared using a dilution that would theoretically allow the response to fall within the linear range.

The assay system suitability will be considered acceptable if:

| qPCR Parameter | Acceptance Criteria |
|---|---|
| Linearity, slope and intercept | The target $R^2$ (linearity) of the calibration curve should be ≥0.96.<br>The target slope of the calibration curve should be between −3.1 to −3.6 indicating a qPCR efficiency of 90% to 110%. |

-continued

| qPCR Parameter | Acceptance Criteria |
|---|---|
| Amplification in controls | Blank samples should have amplification Ct values ≥35 or be "Undetermined"<br>DNase positive control samples should have DNase efficiency of ≥95% of linearized plasmid standard |

Test Method Qualification Protocol

Objective: The purpose of this qualification plan is to define the test method for physical titer of PR001 encapsulated AAV product. This protocol will demonstrate the method produces reliable data and is fit for analysis of purified AAV samples for research and process development purposes (non-GXP). The test method is provided above.

TABLE 7

| Qualification materials | |
|---|---|
| Material Description | Expected Concentration |
| linearized plasmid standard | |
| tox lot | $2.67 \times 10^{11}$ vg/mL |
| reference standard | $6.25 \times 10^{13}$ vg/mL |
| research virus bank | $1.83e^{13}$ |

Accuracy and specificity controls were prepared as described above, with DIW being substituted for DNAse.

TABLE 8

| Method Qualification Acceptance Criteria | | |
|---|---|---|
| | Elements | Acceptance Criteria |
| Linearity | The linearized plasmid standard calibration curve is performed at least 6 different levels according to test method above.<br>At least 6 different standard curves will be performed. | The target $R^2$ (linearity) of the calibration curve should be ≥0.96. The target slope of the calibration curve should be between −3.1 to −3.6 indicating a qPCR efficiency of 90% to 110%. |
| Specificity | Ensure transgene specificity<br>Ensure removal of non-encapsulated DNA | Ct values ≥35 or "Undetermined" of a different transgene in similar or identical vector backbone<br>DNase efficiency of ≥95% of linearized plasmid standard |
| Intra-assay precision | Reference standard virus bank and research virus bank is prepared at at least 2 independent dilutions (see test method above) with each sample being run in triplicate to allow for at least 6 replicates to be analyzed by two independent operators (12 replicates total per execution). | % CV ≤15 of the average concentration within each execution of the qualification runs. |
| Inter-assay precision | Perform the intra-assay procedure across days to include at least 3 independent executions by two analysts of the reference standard virus bank and research virus bank. | % CV ≤15 of the average concentration across the qualification runs. |
| Dilution Linearity and Accuracy | A linearized plasmid standard of 2 known concentrations (see test method above) will be prepared in at least 3 separate executions, with each sample being run in triplicate. | Recovery of ±25% within the nominal known plasmid concentration. |

Plate Layout/Execution Setup

TABLE 9

| qPCR layout (execution 1) | | | |
|---|---|---|---|
| | 1 2 3 | 4 | 5 6 7 |
| A | 2.00E+07 std. | 2e9 plasmid 1:1000 + DNAse | 2e9 plasmid 1:100 |
| B | 2.00E+06 std. | 2e9 plasmid 1:1000 + DNAse | 2e9 plasmid 1:1,000 |
| C | 2.00E+05 std. | 2e9 plasmid 1:1000 + DNAse | J00142 (1:30) 1:100 |
| D | 2.00E+04 std. | water | J00142 (1:30) 1:1,000 |
| E | 2.00E+03 std. | water | J00171 1:100 |
| F | 2.00E+02 std. | PR006 1:1000 spec control | J00171 1:1,000 |
| G | 2.00E+01 std. | PR006 1:1000 spec control | J00059 1:100 |
| H | Water | PR006 1:1000 spec control | J00059 1:1,000 |

TABLE 10

| qPCR layout (executions 2 and 3) | | | |
|---|---|---|---|
| | 1 2 3 | 4 | 5 6 7 |
| A | 2.00E+07 std. | 2e9 plasmid 1:1000 + DNAse | 2e9 plasmid 1:100 |
| B | 2.00E+06 std. | 2e9 plasmid 1:1000 + DNAse | 2e9 plasmid 1:1,000 |
| C | 2.00E+05 std. | 2e9 plasmid 1:1000 + DNAse | J00142 (1:30) 1:100 |
| D | 2.00E+04 std. | water | J00142 (1:30) 1:1,000 |
| E | 2.00E+03 std. | water | J00171 1:100 |
| F | 2.00E+02 std. | water | J00171 1:1,000 |
| G | 2.00E+01 std. | water | J00059 1:100 |
| H | Water | water | J00059 1:1,000 |

Data Handling and Reporting: Raw data will be acquired by the QuantStudio™ 7 to automatically calculate copies/reaction as described in the test method above. This data will be exported into a spreadsheet for calculating additional assay parameters (e.g., accuracy and precision). All resulting data, including details of the experiments such as materials, reagents, equipment used and test conditions, will be reviewed by a second analyst.

Based on the results from all the valid assay runs and all valid concentrations of the reference standard virus and research virus, the overall average titer across all runs from the qualification will be used to establish the nominal titer value for these samples for use in further assay executions.

Example 12: In Vitro Enzymatic Potency Assay for rAAV Encoding GCase

The purpose of this assay is to measure in vitro relative potency of an AAV (e.g., AAV9) encapsulated vector encoding GCase using a cell-based assay.

Laboratory Test Method

The purpose of this method is to measure a dose response of an AAV encapsulated vector encoding GCase in vitro using a cell-based functional assay. This test method may be used for research purpose, such as comparing the responses of different AAV gene therapy product lots.

TABLE 11

| Definitions | |
|---|---|
| AAV9 | Adeno-associated virus serotype-9 |
| CV | Coefficient of variation |
| Excipient | Formulation Buffer |
| FBS | Fetal Bovine Serum |
| FB | Formulation Buffer; same as Excipient |
| GCase | Glucocerebrosidase, also known as β-Glucocerebrosidase |
| Glc | Glucose or glucopyranoside |
| HEK-293T | Human embryonic kidney cells, (contains SV40 T-antigen) |
| PBS | Phosphate-Buffered Saline |
| RT | Room temperature |
| SDS | Safety Data Sheet |
| TS | Test Sample, namely the DS, DP or sample virus |
| VG, vg | Viral Genomes, viral genomes |
| RP | Relative Potency |
| RS | Reference Standard |

TABLE 12

| Materials and Equipment | | |
|---|---|---|
| Material Description | Manufacturer | Item Number |
| HEK293T cells | Source: Prevail | N/A |
| DMEM | Gibco | 11-995-065 |
| FBS (heat inactivated) | Gibco | 1008247 |
| Penicillin (10,000 unit/ml) and Streptomycin (10,000 μg/ml) | Gibco | 15140122 |
| TrypLE Select Enzyme (lX) | Gibco | 12563-011 |
| Assay Buffer: 50 mM citric acid, 176 mM K2HPO4, 10 mM sodium taurocholate, and 0.01% Tween-20 at pH 5.9 | Source: Prevail | N/A |
| Poly-D-Lysine 96-well Black/Clear Flat bottom TC-treated microplate | Corning | 356640 |
| Trypan blue stain | Invitrogen | T10282 |
| Hoechst 33342 Stain (16.234 mM) | Molecular probes | H3570 |
| AAVs to be tested | Source: Prevail | N/A |
| Excipient | To match AAV | N/A |
| Dilution plate: 96-well PCR microplate | Axygen | PCR-96-FS-C |
| Protease inhibitors, EDTA free | Pierce | A32955 or A32965 |
| 96-well black plate with clear flat bottom | Corning | 3904 |

TABLE 12-continued

| Materials and Equipment | | |
|---|---|---|
| Material Description | Manufacturer | Item Number |
| Varioskan Lux Reader | Thermo Fisher Scientific | FA-0049 |
| Biopur Safe Lock 1.5 mL sterile microcentrifuge tubes | Fisher Scientific | 21-402-903 |
| Hemacytometer; INCYTO; disposable; C-chip | Incyte | 22600100 |
| 25 mL sterile disposable reservoirs | Fisher Scientific | 21-381-27C |
| Resorufin-b-D-glucopyranoside | Marker Gene Technologies | M0569 |
| Dimethyl Sulfoxide (DMSO) | Sigma-Aldrich | D2438-50ML |

Background/Theory of Method: PR001 is an exemplary rAAV expressing GBA1. A transduction assay introduces PR001 to the HEK293T cells and results in GCase enzyme expression. Enzyme activity derived from the transduction was assayed in cell lysate using the fluorogenic substrate 4-methylumbelliferyl-β-D-glucopyranoside, which generates the fluorescent product resorufin by GCase catalysis. Relative potency between two or more rAAVs was calculated from the enzymatic activity resulting from the transduction at different amounts of PR001 using parallel line analysis.

TABLE 13

| Reagents/Diluent/Media ITEM |
|---|
| 10% FBS/DMEM/Pen/Strep |
| [Cell Culture Medium] |
| 2% FBS/DMEM |
| 10% FBS/DMEM/1 μM Hoechst 33342 |
| [Recovery Medium] |
| 50 mM Citrate - 176 mM Phosphate Assay Buffer, pH 5.9 |
| 2 μM Hoechst 33342 in 2% FBS/DMEM [Transduction Medium] |
| Assay Lysis Buffer with Protease Inhibitor Cocktail Mini Tablet |
| Resorufin-β-D-glucopyranoside [Stock] |

Procedure: HEK293T cells were plated at 20,000 cells/well in a 96-well plate and allowed to attach overnight at 37° C. and 5% $CO_2$. Serial dilutions of the AAV were prepared in its excipient as shown in Table 14.

TABLE 14

| Dilution | vg/μL | Volume virus (μL) | Source (dilution) | Volume Excipient (μL) | Volume remaining (μL) |
|---|---|---|---|---|---|
| 1 | 5.00E+09 | 60 | N/A | N/A | 20 |
| 2 | 3.33E+09 | 40 | 1 | 20 | 20 |
| 3 | 2.22E+09 | 40 | 2 | 20 | 20 |
| 4 | 1.48E+09 | 40 | 3 | 20 | 20 |
| 5 | 9.88E+08 | 40 | 4 | 20 | 20 |
| 6 | 6.58E+08 | 40 | 5 | 20 | 20 |

10 μL of AAV dilutions or vehicle were transferred to wells following the plate map in FIG. 1. The resulting total vg were achieved (Table 15).

TABLE 15

| vg/μL | μL added | total vg/well |
|---|---|---|
| 5.00E+09 | 10 | 5.00E+10 |
| 3.33E+09 | 10 | 3.33E+10 |
| 2.22E+09 | 10 | 2.22E+10 |
| 1.48E+09 | 10 | 1.48E+10 |
| 9.88E+08 | 10 | 9.88E+09 |
| 6.58E+08 | 10 | 6.58E+09 |

Cells were incubated for 2 to 2.5 hrs. in a 37° C., 5% $CO_2$ incubator. After incubation, 100 μL of Recovery Medium was added to the cells/transduction medium to the wells for a total volume of 150 μL. Cells were incubated for 72+6 hours at 37° C. and 5% $CO_2$ to allow virally-derived GCase expression.

Cell lysates were harvested. GCase activity was measured by adding 10 μL of 1.25 mM Resorufin-β-D glucopyranoside working solution to black plate with clear flat bottom followed by 40 μL of cell lysate. The plate was immediately read on a Varioskan plate reader at 37° C.

Analysis: A parallel analysis of the data to calculate the relative potency was performed as follows:

1. Calculate the % CV for each vg/well point, it should be ≤30%. Up to one replicate per vg/well point can be discarded to achieve this if necessary.
2. Perform a log transformation of the virus amounts and GCase activity (RFU/hr).
3. Plot response as Log (RFU/hr) vs Log (virus).
4. Perform a linear regression for each sample.
5. Perform a new linear regression with a common slope "A" (Y=A X+b).
6. Using the parameters obtained in step 5, calculate the relative potency using the following formula:

$$\text{Relative potency}(\%)=10\hat{}((b-b_{reference})/A)\times 100$$

7. Report results relative to reference standard as percentage, no decimals (e.g., if result is 100.50 will be 101%).

TABLE 16

| Assay System Suitability and Sample Criteria | |
|---|---|
| Parameter | Acceptance Criteria |
| Slope to average slope ratio | The ratio of the slope of Analysis step 3 to common slope (Analysis step 4) should be between 0.60-1.40 |
| $R^2$ | The target $R^2$ of linear regression in Analysis step 3 for RS should be >0.9 |
| Reference Standard and test sample replicates | % CV ≤30. One replicate can be masked to achieve % CV ≤30. |

Test Method Qualification Protocol

Objective: The purpose of this qualification plan is to define the test method to measure relative potency of PR001 in vitro using a cell-based assay. This protocol will demonstrate that the method produces reliable data and is fit for analysis of AAV samples for research and process development purposes (non-GXP).

TABLE 17

| Qualification materials | |
|---|---|
| Material Description | Physical Titer |
| PR001 reference standard | 2.62E+13 vg/mL |
| Specificity control (PR006 product) | 1.64E+13 vg/mL |

Qualification plan: The validation will be performed according to the validation of analytical test methods, a procedure described in the International Conference on Harmonization (ICH) Q2 (R1), USP<1032> and USP<1033>. Validation testing will consist of testing AAV9-GBA DP at 50%, 100%, and 200% relative potency levels as well as specificity. To evaluate method linearity, accuracy and precision (repeatability and intermediate precision), each level will be tested by two analysts. Relative potency from each assay is independent and regarded as a single assay determination. Each plate will contain one reference standard and up to two test samples. If system suitability fails on a plate, then the plate will be repeated. If system suitability fails for a sample, then only the failed sample will be repeated. All samples should meet the assay acceptance criteria defined in the method and the validation criteria defined in this protocol. Determination of specificity will also be performed using an unrelated AAV product that does not carry GBA1. Detection and quantitation limits have not been included because they are not relevant to a method that reports relative potency as explained in USP<1032>. Table 18 summarizes the validation procedures and the acceptance criteria that will be used to assess the performance of the method.

TABLE 18

| Summary of Validation Procedure and Qualification Acceptance Criteria | | | |
|---|---|---|---|
| Parameter | Definition | Procedure and Data Analysis | Acceptance Criteria |
| Linearity | The method's ability (within a given range) to obtain test results which are directly proportional to concentration (amount) of analyte in samples. | AAV9-GBA test samples will be diluted to 50%, 100%, and 200% of the reference standard, and will be tested in up to 4 times per concentration. The mean (measured) relative potency will be plotted versus the expected relative potency and analyzed using linear regression. | The coefficient of determination (R2) for linear regression will be ≥0.9. |
| Accuracy | The closeness of agreement between a value accepted as the sample's true value and the value obtained from the measurement. | The linearity data will be evaluated to assess accuracy. The mean % recovery will be calculated at each level. | The mean % recovery at each level will be between 50% and 150% of the theoretical value. |
| Repeatability | The precision (i.e. the closeness of agreement between a series of measurements obtained from multiple sampling of the same homogeneous sample under the prescribed conditions) measured under the same operating conditions over a short interval of time. | The linearity data will be evaluated to assess repeatability. The percent relative standard deviation (% RSD) will be calculated at each level for each assay (i.e. same analyst and same week). | The % RSD will be ≤30% at each level for each analyst for each week. |

TABLE 18-continued

Summary of Validation Procedure and Qualification Acceptance Criteria

| Parameter | Definition | Procedure and Data Analysis | Acceptance Criteria |
|---|---|---|---|
| Intermediate Precision | The precision (i.e. the closeness of agreement between a series of measurements obtained from multiple sampling of the same homogeneous sample under the prescribed conditions) expressing variation from different weeks and different analysts. | The linearity data will be evaluated to assess intermediate precision. The overall % RSD will be calculated at each level. | The overall % RSD will be ≤30% at each level. |
| Range | The interval between the upper and lower concentration demonstrating a suitable level of linearity, accuracy and precision. | The results from the linearity, accuracy and precision will be used to determine the method range. | The range will be determined in the study. Sample concentrations within the range must meet the acceptance criteria for linearity, accuracy and precision. |
| Specificity | The ability to unequivocally assess the analyte in the presence of components which may be expected to be present. | The alternate molecule will be tested in one assay by one analyst. | The alternate molecule will not meet the sample acceptance criteria. |

Linearity: AAV9-GBA test samples will be diluted to 50%, 100%, and 200% of the reference standard, and will be tested in seven assays by two analysts. The mean (measured) relative potency will be plotted versus the expected relative potency and analyzed using linear regression. The resulting linearity equation and coefficient of determination ($R^2$) will be reported. Assay plates that fail system suitability not be used for analysis.

Accuracy: The linearity data will be evaluated to assess accuracy. The mean % recovery will be calculated at each level using the following formula:

$$\%\text{ Recovery} = \left(\frac{\text{Mean Measured Value}}{\text{Theoretical Value}}\right) \times 100\%$$

The % recovery values at each level will be reported.

Repeatability: The linearity data will be evaluated to assess repeatability. The percent relative standard deviation (% RSD) will be calculated at each level for each assay (i.e., same analyst and same week) and reported.

Intermediate Precision: The linearity data will be evaluated to assess repeatability. The overall % RSD will be calculated at each level and reported.

Range: The lowest and highest potency tested that meet the criteria for linearity, accuracy and precision experiments will be used to determine the method range and will be reported.

Specificity: An alternate molecule (specificity sample) will be tested in one assay by one analyst. The specificity sample will be diluted into the assay as if they were AAV9-GBA test samples. The specificity sample is an alternate molecule (AM): PR006.

Data Handling and Reporting: Raw data will be acquired by the SkanIt RE 5.0 software and parallel line analysis will be performed as indicated in the test method above. This data will be exported into a spreadsheet for calculating additional assay parameters (e.g., accuracy and precision). All resulting data, including details of the experiments such as materials, reagents, equipment used and test conditions, will be recorded and reviewed by a second analyst.

Based on the results from all the valid assay runs and all valid concentrations of the reference standard virus and research virus, the overall average relative potency across all runs from the qualification will be used to establish the nominal RP value for these samples for use in further assay executions.

An example of the potency assay data from several PR001 samples is shown in FIG. 2.

Example 13: Quantitative PCR Assay to Measure Titer of rAAV Encoding Progranulin The purpose of this assay is to quantify the physical titer of an AAV (e.g., AAV9) encapsulated vector encoding PGRN using quantitative PCR (qPCR) by comparison with a known standard or by ddPCR in the absence of standards. This test method may be used to quantitate physical vector genome titer in purified AAV viral samples or in process production fractions.

Laboratory Test Method

TABLE 19

| Materials | | |
|---|---|---|
| Material Description | Manufacturer | Item Number |
| PerfeCTa qPCR supermix with ROX | QuantaBio | 95051-500 |
| ddPCR supermix for probes (no dUTP) | BioRad | 1863027 |
| UltraPure distilled water (DIW) | Invitrogen | 10977-023 or equivalent |
| MicroAmp optical 96-well reaction | Applied Biosystems | 43-067-37 |
| MicroAmp optical adhesive film | Applied Biosystems | 43-119-71 |
| Foil Heat Seal | BioRad | 1814040 |
| Pipet Tips for Automated Droplet Generator | BioRad | 1864120 |
| DG32 Automated Droplet Generator Cartridges | BioRad | 1864108 |
| ddPCR 96-well Plates (semi-skirted) | BioRad | 12001925 |
| Automated Droplet Generation Oil for Probes | BioRad | 1864110 |
| OctaPool ™Solution Reservoirs, 25 ml disposable, sterile | Thomas Scientific | 1159X93 or equivalent |
| DNA Away | Fisher Scientific | M0303L or equivalent |
| PCR 8-Well Tube Strips and Caps | VWR | 2017-004 |
| Eppendorf DNA LoBind Microcentrifuge Tubes 1.5 ml | Eppendorf | 022431021 |
| Tween-80 (polysorbate-80) | VWR | JT4117-02 |
| Proteinase K, 20 mg/mL | Promega | MC5005 |
| 20% SDS Solution | Fisher Scientific | BP1311-1 or equivalent |
| 0.5M EDTA pH 8.0 | Fisher Scientific | BP2482 or equivalent |
| TE buffer, pH 8.0 | Fisher Scientific | AM9849 or equivalent |
| Falcon conical tube 15 ml | Fisher Scientific | 14 959 53A or equivalent |
| Falcon conical tube 50 ml | Fisher Scientific | 14 432 22 or equivalent |
| DNase I (RNAse free) | New England BioLabs | M0303S |
| Lambda Hind III digested DNA | New England BioLabs | B7025 |

TABLE 20

| Equipment | | |
|---|---|---|
| Equipment Description | Manufacturer | Item Number |
| QuantStudio ™ 7 Flex | Applied Biosystems | 4485695 |
| Pipette Set LTS Pipet-Lite XLS+ manual (P2, P20, P200, P1000) | Rainin | 30386597 |
| Combination PCR Workstations | AirClean ™ Systems | AC632LFUVC |
| Sorvall ST8R centrifuge | Fisher Scientific | 75 230 395 |
| Myspin 6 mini centrifuge | Fisher Scientific | 75 004 061 or equivalent |
| Mini Vortex Mixer | Fisher Scientific | 400815B or equivalent |
| Simpliamp PCR Thermal Cycler | Thermo Fisher | A24811 or equivalent |
| PX1 plate sealer | BioRad | 181-4000 |
| Automated Droplet Generator | BioRad | 1864101 |
| QX200 Droplet Reader | BioRad | 1864001 and 1864003 |
| C1000 Touch Thermal Cycler | BioRad | 10000068706 |

The linearized plasmid PR006A was linearized with PmlI. The virus reference standard was a different lot of PR006.

TABLE 21

| Primers | | |
|---|---|---|
| Primer or Probe | Name | Sequence |
| Forward primer | PR006-1_F | GTCTTCCACGACTGTGGGAT (SEQ ID NO: 9) |
| Reverse primer | PR006-1_R | GTCAGGGCCACCCAGCTC (SEQ ID NO: 10) |
| TaqMan probe | PR006-1_Probe | 6FAM-CCGGTTGAGCCACCATGTGGACCC (SEQ ID NO: 11)-TAMRA |

Note:
all primers are assumed to be provided at 100 μM from the vendor and are of HPLC level purity or higher.

Background/Theory of Method: To determine the amount of copies of AAV encapsulating the target sequence, the desired sequence is amplified using PCR using one or two methodologies. The first method uses real-time qPCR, in which a fluorescent reporter molecule (such as a dye-labeled probe) is used to monitor the progress of the amplification reaction. With each amplification cycle, the increase in fluorescence intensity is proportional to the increase in amplicon concentration, with the qPCR instrument system collecting data for each sample during each PCR cycle. The resulting plots of fluorescence vs. cycle number for all the samples are then set with their background fluorescence at a common starting point. The cycle number at which an amplification plot crosses a predetermined background threshold fluorescence level is called the "Ct" or threshold cycle. By comparing the Ct values from unknowns with a known standard diluted at various concentrations, the starting concentration of the unknown samples are determined, thereby yielding the desired amount of copies (if present) in a given sample. The second method uses ddPCR, which discretizes the sample into individual droplets. The droplets are then amplified by PCR, and the droplets are counted as either positive (containing fluorescence) or negative (no fluorescence) in a droplet reader. The absolute copy number is then determined directly from the ratio of positive to total droplets using Poissonian statistics and therefore does not require standards.

Procedure:

10% Polysorbate-80, PCR Dilution Buffer, 10× Proteinase K Buffer, and Standard Diluent were prepared. The linearized plasmid was diluted to 2e9 copies/μL if needed. 10-fold serial dilutions were performed in standard diluent using the first standard to prepare a standard curve ranging from $2\times10^7$ copies/μL to 20 copies/μL. A set of standards ($2\times10^7$ to 20 copies/μL) was aliquoted into 7 wells of an 8-well 0.2 mL PCR tube strip such that each strip serves as a single-use standard curve. Primer stock was prepared from lyophilized primer.

Blanks and DNAse control were prepared. Reference standards and samples were prepared. All samples and reference standards were run in triplicate. Sample dilutions for all sample types were selected based on initial concentration based on Table 22.

TABLE 22

Sample and reference standard dilution procedure

| Theoretical sample concentration (copies/mL) | Method | Dilutions to prepare |
|---|---|---|
| $<1\times10^{12}$ | qPCR | 1:10 and 1:100 |
| $<1\times10^{12}$ | ddPCR | 1:100 and 1:1000 |
| $\geq1\times10^{12}$ | qPCR | 1:100 and 1:1000 |
| $\geq1\times10^{12}$ | ddPCR | 1:1000 and 1:10000 |
| Unknown | qPCR | 1:10, 1:100 and 1:1000 |
| Unknown | ddPCR | 1:100, 1:1000 and 1:10000 |

qPCR master mix was prepared as detailed in Table 23:

TABLE 23 qPCR master Reaction Mix Preparation

| Component | Stock conc (μM) | Final conc (μM) | Volume of stock per reaction (μL) |
|---|---|---|---|
| qPCR master Mix | NA | NA | 10 |
| Forward Primer | 10 | 0.5 | 1 |
| Reverse Primer | 10 | 0.5 | 1 |
| Probe | 5 | 0.25 | 1 |
| Template or sample | Variable | | 5 |
| DIW | NA | NA | 2.0 |
| | | | 20 μL (total) |

For ddPCR, the following reaction mix was used, prepared similarly to Table 23:

TABLE 24 ddPCR master Reaction Mix Preparation

| Component | Stock conc (μM) | Final conc (μM) | Volume of stock per reaction (μL) |
|---|---|---|---|
| ddPCR master Mix | NA | NA | 11 |
| Forward Primer | 10 | 0.5 | 1.1 |
| Reverse Primer | 10 | 0.5 | 1.1 |
| Probe | 5 | 0.25 | 1.1 |
| Template or sample | Variable | | 2.5 |
| DIW | NA | NA | 5.2 |
| | | | 22 μL (total) |

qPCR or ddPCR were run as follows. For qPCR, 15 μL master reaction mix was added to all wells of the assay plate that will contain samples. For ddPCR, 19.5 μL master reaction mix was added to all wells of the assay plate that will contain samples. Previously aliquoted standards were added into the plate at 5 μl per well for qPCR. For ddPCR this step can be skipped as a standard curve is not used. 5 μL diluted samples, controls or reference standards for qPCR, 2.5 μL diluted samples for ddPCR, were added to the respective plates. A no template control should also be included in each assay, in which water is substituted for sample.

The qPCR was run using the following settings with the maximum ramp rate:

TABLE 25 qPCR Conditions

| Stage | Temperature | Time (mm:ss) | Cycles |
|---|---|---|---|
| 1 | 95° C. | 5:00 | 1 |
| | 95° C. | 0:15 | |
| 2 | 60° C. | 1:00 | 45 |
| 3 | 4° C. | Hold | 1 |

The final copy number was determined as follows:

a. The amplification of the target amplicon based on fluorescence from all samples in the assay plate was recorded, and the Ct value is determined automatically by the QuantStudio™ software.

b. A standard curve was prepared by plotting Ct of each standard vs. the number of copies per reaction on a logarithmic scale (the final graph is semi-log with the y-axis being linear and x-axis being on a log 10 scale). This was fit to a straight line.

c. Vector copy numbers in each reaction well were determined by interpolating Ct values with the standard curve determined in (b) and are to be included in the data exported from the instrument.

d. Finally, the number determined in (c) above was multiplied by the dilution factors employed to prepare the samples to yield the final copy number. If 2 or more dilutions are used on a sample, all valid values in the standard curve were averaged after calculations.

ddPCR was run as follows:

TABLE 26

| ddPCR Conditions | | | |
|---|---|---|---|
| Stage | Temperature | Time (mm:ss) | Cycles |
| 1 | 95° C. | 10:00 | 1 |
| 2 | 94° C. | 0:30 | 39 |
| | 60° C. | 1:00 | |
| 3 | 98° C. | 10:00 | 1 |
| 4 | 12° C. | Hold | 1 |

The final copy number was determined automatically by the QuantSoft software based on the number of positive drops relative to the total drop count using Poissonian statistics. If 2 or more dilutions were used on a sample, all valid values in the standard curve will be averaged after calculations. These counts are to be included in the data export. If the Ct value lies above the linear range of the standard curve for qPCR or is determined to be "No call" in the ddPCR, samples will be re-prepared using a dilution that would theoretically allow the response to fall within the linear range.

The assay system suitability will be considered acceptable if:

| qPCR Parameter | Acceptance Criteria |
|---|---|
| Linearity, slope and intercept | The target $R^2$ (linearity) of the calibration curve should be ≥0.96. The target slope of the calibration curve should be between −3.1 to −3.6 indicating a qPCR efficiency of 90% to 110%. The target intercept of the calibration curve should be between a Ct value of 36 and 41. |
| Amplification in negative controls | All blanks and DNAse positive controls should have amplification Ct values ≥35 or be "Undetermined" |
| Accuracy | Reference standard calculated copies for mean concentrations in valid range is ±20% of the expected concentration |

| ddPCR Parameter | Acceptance Criteria |
|---|---|
| Amplification in negative controls | All blanks and DNAse positive controls should have a concentration less than 5 copies/μL |
| Accuracy | Reference standard calculated copies is ±20% of the expected concentration |

Sample suitability will be considered acceptable if:

| ddPCR Parameter | Acceptance Criteria |
|---|---|
| Droplet count | The number of total accepted droplets must be >10000. |

Test Method Qualification Protocol

Objective: The purpose of this qualification plan is to define the test method for physical titer of PR006 encapsulated AAV product. This protocol will demonstrate the method produces reliable data and is fit for analysis of purified AAV samples for research and process development purposes (non-GXP). The test method is provided above.

TABLE 27

| Qualification materials<br>Material Description |
|---|
| PR006 linearized plasmid standard |
| PR006 reference standard virus bank |
| PR006 research virus bank |
| Specificity control (PR001 product) |

Accuracy and specificity controls were prepared as described above, with DIW being substituted for DNAse.

TABLE 28

| Method Qualification Acceptance Criteria | | |
|---|---|---|
| | Elements | Acceptance Criteria |
| Linearity | The linearized plasmid standard calibration curve is performed at least 6 different levels according to the test method above. At least 6 different standard curves will be performed. | The target $R^2$ (linearity) of the calibration curve should be ≥0.96. The target slope of the calibration curve should be between −3.1 to −3.6 indicating a qPCR efficiency of 90% to 110%. |
| Specificity | Ensure transgene specificity Ensure removal of non-encapsulated DNA | Ct values ≥35 or "Undetermined" of a different transgene in similar or identical vector backbone DNase efficiency of ≥95% of linearized plasmid standard |
| Intra-assay precision | Reference standard virus bank and research virus bank is prepared at at least 2 independent dilutions (see the test method above) with each sample being run in triplicate to allow for at least 6 replicates to be analyzed by two independent operators (12 replicates total per execution). | Report results as a % CV of the average concentration within each execution of the qualification runs. |
| Inter-assay precision | Perform the intra-assay procedure across days to include at least 3 independent executions by two analysts of the reference standard virus bank and research virus bank. | Report results as a % CV of the average concentration across the qualification runs. |
| Dilution Linearity and Accuracy | A linearized plasmid standard of 3 known concentrations (see the test method above) will be prepared in at least 3 separate executions, with each sample being run in triplicate to allow for at least 27 replicates to be analyzed by two independent operators, yielding 54 replicates in total. | Report results as a % CV of the nominal known plasmid concentration. |

Plate Layout/Execution Setup

TABLE 29

| qPCR layout (execution 1) | | | | | | | |
|---|---|---|---|---|---|---|---|
| | 1 | 2 | 3 | 4 | 5 | 6 | 7 |
| A | 2.00E+07 std. | | | 2e9 plasmid 1:1000 + DNAse | | 2e9 plasmid 1:10 | |
| B | 2.00E+06 std. | | | 2e9 plasmid 1:1000 + DNAse | | 2e9 plasmid 1:100 | |
| C | 2.00E+05 std. | | | 2e9 plasmid 1:1000 + DNAse | | 2e9 plasmid 1:1000 | |
| D | 2.00E+04 std. | | | water | | Research virus 1:100 | |
| E | 2.00E+03 std. | | | water | | Research virus 1:1000 | |
| F | 2.00E+02 std. | | | PR001 1:1000 spec control | | Research virus 1:10000 | |
| G | 2.00E+01 std. | | | PR001 1:1000 spec control | | Reference standard 1:100 | |
| H | Water | | | PR001 1:1000 spec control | | Reference standard 1:1000 | |

TABLE 30

| qPCR layout (executions 2 and 3) | | | | | | | |
|---|---|---|---|---|---|---|---|
| | 1 | 2 | 3 | 4 | 5 | 6 | 7 |
| A | 2.00E+07 std. | | | 2e9 plasmid 1:1000 + DNAse | | 2e9 plasmid 1:10 | |
| B | 2.00E+06 std. | | | 2e9 plasmid 1:1000 + DNAse | | 2e9 plasmid 1:100 | |
| C | 2.00E+05 std. | | | 2e9 plasmid 1:1000 + DNAse | | 2e9 plasmid 1:1000 | |
| D | 2.00E+04 std. | | | water | | Research lot 1:100 | |
| E | 2.00E+03 std. | | | water | | Research lot 1:1000 | |
| F | 2.00E+02 std. | | | water | | Research lot 1:10000 | |
| G | 2.00E+01 std. | | | water | | Reference standard 1:100 | |
| H | Water | | | water | | Reference standard 1:1000 | |

Data Handling and Reporting

Raw data will be acquired by the QuantStudio™ 7 to automatically calculate copies/reaction as described in the test method above. This data will be exported into an excel sheet for calculating additional assay parameters (e.g., accuracy and precision). All resulting data, including details of the experiments such as materials, reagents, equipment used and test conditions, will be recorded and reviewed by a second analyst.

Based on the results from all the valid assay runs and all valid concentrations of the reference standard virus and research virus, the overall average titer across all runs from the qualification will be used.

Example 14: In Vitro Enzymatic Potency Assay for rAAV Encoding Progranulin

Figure 3:
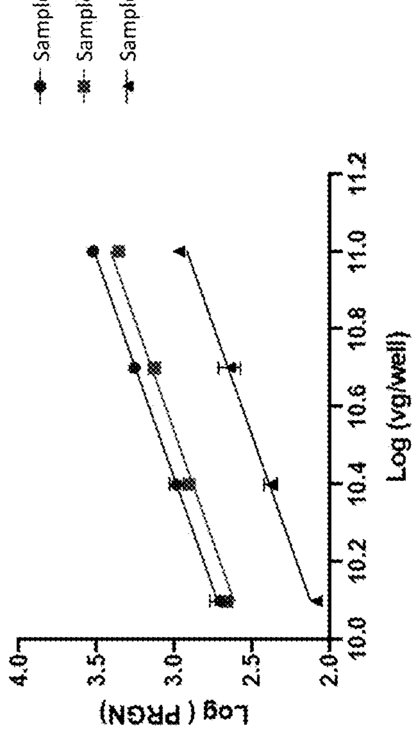
FIG. 3 depicts a line graph and calculations of relative potency of several rAAV samples expressing PGRN.

This assay measures in vitro potency for rAAV (e.g., AAV9) encoding PGRN. The assay was performed in a 96-well format. HEK293 cells were plated at 20,000 cells/well and transduced the following day with AAV9-GRN at different drug concentrations for both the test article and the reference standard. At 72 hrs post transduction, PGRN levels were measured by ELISA (AdipoGen Life Sciences CAT # AG-45A-0018YEK-KI01). The reported value of the relative potency to the reference standard was calculated using parallel line analysis. An example of the potency assay data from several PR006 (rAAV comprising AAV9 capsid and encoding PGRN) samples is shown in FIG. 3. Alternatively, 6 MOI groups may be used to decrease the variability of the slope ratio. The dilution factor can also be changed to cover the range of the progranulin levels of the samples, thereby minimizing the number of repeats.

Example 15: Assays for Measuring Protein Purity and Viral Capsid Protein Ratio of rAAV Compositions Purpose: The purpose of this method is to estimate the protein purity and Viral Protein ratio of rAAV samples by sodium dodecyl sulfate polyacrylamide gel electrophoresis (SDS-PAGE).

Scope and Background: This test method can be used to estimate the purity or band ratio in a semi-quantitative manner of purified rAAV viral samples or in process production fractions.

SDS-PAGE resolves components of a protein mixture under reduced and denatured conditions based on relative molecular weight to assess homogeneity of a sample. SYPRO® Ruby protein gel stain is an ultrasensitive, luminescent stain that detects proteins separated by PAGE. The purpose of this assay is to determine the relative quantity of AAV capsid proteins (VP 1, 2, and 3) and other impurity bands. The method can be used to calculate the ratio of the VP bands and/or the percent purity of these bands in relation to all impurity bands. The molecular weight of all proteins in the sample can be determined in relation to the molecular weight ladder standard.

Procedure: Fix buffer, wash buffer, IVIES running buffer and sample buffer mix are prepared. rAAV sample serial dilutions are prepared. Samples may be run in triplicate. Samples and molecular weight ladder standard are loaded into the gel, and the gel is run. The gel is then stained with SYPRO® Ruby stain. An image of the stained gel is then analyzed (ChemiDoc™ MP Imaging System, BioRad) to calculate the VP band ratio and purity of the sample. Expected molecular weights of VP1, VP2 and VP3 are as follows: VP1=87 kDa, VP2=72 kDa, VP3=62 kDa.

The assay system suitability will be considered acceptable if:

| Gel Parameter | Acceptance Criteria |
|---|---|
| Samples within the Dynamic Range of Detection | If any of the VP bands for a given sample are more than 20% highlighted in red when the “highlight Saturated Pixels” setting is selected. Other samples can remain valid, but a specific sample that fails this requirement must be repeated. |
| Effectively Migrated Gel | The running front, or dye, on the gel should be the bottom of the gel |

Two lots of PR006 (AAV9-PGRN) material exhibited a difference in in vitro potency. To investigate this difference, SDS-PAGE as described above is performed to determine if the level of impurities and VP capsid protein ratios are significantly different in these lots. Analytical ultracentrifugation is also performed to investigate the ratio of full to partial particles in these lots.

The scope of this study is to compare two rAAV lots in terms of product purity and full versus empty capsid particles, product attributes which may influence product potency. This will be assessed by two methods: the first will analyze viral protein ratios and the amount of impurities relative to the viral proteins by SDS-PAGE. The second utilizes analytical ultracentrifugation (AUC) in order to separate and quantify the ratio of full to partial particles. The SDS-PAGE will be performed on both lots on the same gel to allow for relative comparisons from test material stored at ≤−60° C.

Sample disposition: Prior to testing, a single vial of G14C0519 will be aliquoted and documented. One 100 μL aliquot will be stored at <−60° C. for use in a single run for SV-AUC as detailed below. A separate 50 μL aliquot will be stored at <−60° C. until analyzed by SDS-PAGE as detailed above.

Testing procedures: The SDS-PAGE of these samples will be analyzed as described above. In addition to loading the samples based on total vg as reported on the CoA for each lot, the samples will also be tested by loading an equivalent amount based on total protein using the protein concentration by micro BCA as reported on the CoA for each lot.

Analytical ultracentrifugation will be performed. Briefly, samples are initially diluted with sample buffer to an OD of 0.5 at 230 nm and run as a single replicate. Samples are run using the following parameters:

TABLE 33

| Process step | Parameter | Setting |
|---|---|---|
| XLI data collection | Rotor speed | 12000 rpm |
| | Scan speed | 90 sec/cell |
| | Scans | 150-200 |
| | Temperature | 20° C. |
| | Wavelength | 230 nm |
| SEDFIT analysis | S range (min-max) | 0-200 (or as evaluated) |
| | Bottom (cm) | 7.15 |
| | Meniscus (cm) | Float |
| | f/f0 | Float |
| | Confidence interval | 0.68/0.95 |
| | Vbar (mL/g)3 | 0.73 |
| | ρ (g/mL) | 1.000 |
| | η (cP) | 0.01002 |
| | RI noise | Float |
| | TI noise | Float |

From the resulting SEDFIT c(s) profiles and to evaluate whether a peak is reproducible or a possible modeling artifact ('false' peak) due to the model fitting, a reproducible threshold criterion is implemented. The reproducible threshold is defined as the percentage of absorbance for capsid species<0.5% and/or <0.002 OD, species below this criteria are not included in the tabulated results. Full details of the analysis will be included with the Bioanalysis report. The resulting ratio of full to partial particles (based on percent of the total as fit in the c(s) distribution) as determined by this analysis will be reported.

Data Analysis and Data Reporting: All data will be recorded and documented. For the SDS-PAGE results, the % composition of VP1 capsid protein will be compared between the batches. Based on the literature (see, Bosma et al. (2018) *Gene Therapy* 25:415-424 and references therein), this ratio of VP proteins is a critical factor in controlling product potency. For the AUC method, a higher % full particles relative to empty and partially packaged capsids would correlate to increased potency.

NUMBERED EMBODIMENTS

Notwithstanding the appended claims, the disclosure sets forth the following numbered embodiments:

1. A method for producing a cellular lysate, the method comprising:
(i) obtaining a bioreactor containing insect cells suspended in a mixture comprising two or more serum free, and/or protein free insect cell culture medias;
(ii) infecting the insect cells with a first population of Baculovirus vectors at a multiplicity of infection (MOI) of between about 1.0 and 2.0, wherein the first population of Baculovirus vectors comprise an expression cassette encoding a gene product of interest;
(iii) infecting the insect cells with one or more additional populations of Baculovirus vectors at a MOI of between about 1.0 and 2.0, wherein the additional populations each comprise an expression cassette encoding AAV Rep protein and/or AAV Cap protein;
(iv) culturing the infected insect cells under conditions under which the infected insect cells produce recombinant adeno-associated virus (rAAV) particles encoding the gene of interest; and
(v) lysing the infected insect cells to produce a cellular lysate comprising the rAAV particles.
2. The method of embodiment 1, wherein each of the two or more serum free and/or protein free insect culture medias are selected from 4Cell Insect CD Medium, ESF-921, ESF-AF, ExpiSf CD Medium, Express Five SFM, baculoGROW, IS SF, and SF900 II SFM.
3. The method of embodiment 1 or 2, wherein the mixture comprises from about 10% v/v to about 50% v/v SF900 II SFM media.
4. The method of any one of embodiments 1 to 3, wherein the insect cells of (i) are obtained after 4-6 passages of a master seed train.
5. The method of any one of embodiments 1 to 4, wherein the infection of (ii) and the infection of (iii) occur simultaneously.
6. The method of any one of embodiments 1 to 5, wherein the insect cells are present in the bioreactor at a cell density of between 8E+06 viable cells per mL (vc/mL) to about 20E+06 vc/mL.
7. The method of any one of embodiments 1 to 6, wherein the culturing of (iv) occurs for between 1 day and 5 days.
8. The method of any one of embodiments 1 to 7, wherein the lysing of (v) comprises contacting the infected insect cells with a detergent.
9. The method of any one of embodiments 1 to 8 further comprising the step of clarifying the cellular lysate by depth filtration.
10. The method of any one of embodiments 1 to 9 further comprising the step of concentrating the rAAV particles in the lysate by tangential flow filtration and/or diafiltration.
11. The method of any one of embodiments 1 to 10, wherein the gene product of interest comprises a peptide, polypeptide, inhibitory nucleic acid, or a combination thereof.

12. The method of embodiment 11, wherein the gene product of interest comprises glucocerebrosidase (GCase), progranulin (PGRN), prosaposin (PSAP), C9orf72, triggering receptor expressed on myeloid cells 2 (TREM2), apolipoprotein E2 (ApoE2) or parkin.
13. The method of any one of embodiments 1 to 12, wherein the rAAV particles comprise an AAV capsid protein that is AAV1, AAV2, AAV3, AAV4, AAV5, AAV6, AAV7, AAV8, AAV9 or a variant of any of the foregoing.
14. The method of any one of embodiments 1 to 13, wherein the cellular lysate comprises
(a) from about 1E+11 viral genomes per milliliter (vg/mL) to about 1.0E+13 vg/mL;
(b) from about 2E+11 viral genomes per milliliter (vg/mL) to about 1.0E+13 vg/mL; or
(c) from about 5E+11 viral genomes per milliliter (vg/mL) to about 1.0E+13 vg/mL.
15. A pharmaceutical composition comprising the cellular lysate produced by the method of any one of embodiments 1 to 14.
16. The composition of embodiment 15 further comprising a cryoprotectant.
17. A method for producing a therapeutic composition, the method comprising:
(i) obtaining a cellular lysate comprising rAAV particles;
(ii) contacting an affinity chromatography column with the cellular lysate, wherein the affinity column comprises a binding agent specific for a capsid protein of the rAAV particles under conditions under which the rAAV particles bind to the affinity chromatography column;
(iii) eluting the bound rAAV particles from the column thereby producing a first eluate;
(iv) performing anion-exchange chromatography on the first eluate to produce a second eluate, wherein the second eluate comprises fewer empty rAAV particles than the first eluate;
(v) concentrating the second eluate by performing tangential flow filtration using a flow buffer comprising Tris, $MgCl_2$, NaCl, and Poloxamer 188, thereby producing a therapeutic composition comprising rAAV particles.
18. The method of embodiment 17, wherein the cellular lysate of (i) is obtained by the method of any one of embodiments 1 to 14.
19. The method of embodiment 17 or 18, wherein the binding agent comprises an affinity resin specific for AAV9 capsid protein.
20. The method of any one of embodiments 17 to 19, wherein the anion-exchange chromatography comprises mixing the first eluate with an equilibration buffer to produce a mixture having a conductivity of between about 0.5 mS/cm to 5 mS/cm, optionally wherein the mixture has a conductivity of 2 mS/cm, binding the mixture to a quaternary amine-containing resin to bind the rAAV particles in the mixture to the resin, and eluting the rAAV particles from the resin to produce the second eluate.
21. The method of any one of embodiments 17 to 20, wherein the second eluate is concentrated to from about 1.0E+12 vg/mL to about 1E+14 vg/mL.
22. The method of any one of embodiments 17 to 21, wherein the therapeutic composition comprises from about 1E+13 vg/mL to about 1E+14 vg/mL.
23. The method of any one of embodiments 17 to 22, wherein the therapeutic composition comprises less than about 15% empty rAAV particles.
24. A therapeutic composition comprising rAAV particles, wherein the rAAV particle comprises an AAV capsid protein and an expression cassette encoding a gene product of interest, wherein the therapeutic composition comprises more than about 1E+13 vg/mL rAAV particles, and wherein the therapeutic composition comprises less than about 15% empty rAAV particles.
25. The therapeutic composition of embodiment 24, wherein the gene product of interest comprises a peptide, polypeptide, inhibitory nucleic acid, or a combination thereof.
26. The therapeutic composition of embodiment 25, wherein the gene product of interest comprises GCase, GRN, PSAP, TREM2, ApoE2 or parkin.
27. The therapeutic composition of any one of embodiments 24-26, wherein the rAAV particles comprise an AAV capsid protein that is AAV1, AAV2, AAV3, AAV4, AAV5, AAV6, AAV7, AAV8, AAV9 or a variant of any of the foregoing.
28. The therapeutic composition of any one of embodiments 24-27, wherein the therapeutic composition comprises from about 1E+13 vg/mL to about 1E+14 vg/mL.
29. The therapeutic composition of any one of embodiments 24-28, wherein the therapeutic composition is in a container.
30. The therapeutic composition of any one of embodiments 24-29, wherein the therapeutic composition is sterile.
31. The therapeutic composition of embodiment 30, wherein the therapeutic composition does not promote microbial growth.
32. The therapeutic composition of any one of embodiments 24 to 31, wherein the therapeutic composition comprises an endotoxin level less than about 0.5 EU/mL.
33. The therapeutic composition of any one of embodiments 24 to 32, wherein the rAAV particle comprises AAV9 capsid protein.
34. The therapeutic composition of any one of embodiments 24 to 33, wherein more than about 1.0E+13 vg/mL of the rAAV comprises the gene product.
35. The therapeutic composition of any one of embodiments 24 to 34, wherein the TCID50 titer of the rAAV is from about 1,000 vg/IU to about 6,000 vg/IU.
36. The therapeutic composition of any one of embodiments 24 to 35, wherein the gene product is GCase.
37. The therapeutic composition of embodiment 36, wherein the GCase activity is at least 110% relative to a reference standard, wherein the reference standard is a purified rAAV encoding GCAse.
38. The therapeutic composition of any one of embodiments 24 to 37, wherein the infectious titer is from about 8.0E+9 IU/mL to about 1.2E+10 IU/mL.
39. The therapeutic composition of any one of embodiments 24 to 38, wherein the osmolality is between about 300 mOsm/kg and about 500 mOsm/kg.
40. The therapeutic composition of any one of embodiments 24 to 39, wherein the pH is between about 7 and about 9.
41. The therapeutic composition of any one of embodiments 24 to 40, wherein the therapeutic composition is free from visible particles.

42. The therapeutic composition of any one of embodiments 24 to 41, wherein the therapeutic composition comprises less than about 6000 particles that are larger than about 10 μm per container, and less than about 600 particles that are larger than about 25 μm per container.
43. The therapeutic composition of any one of embodiments 24 to 42, wherein the therapeutic composition comprises less than or equal to about 3% aggregates.
44. The therapeutic composition of any one of embodiments 24 to 43, wherein the therapeutic composition comprises a total protein level from about 300 μg/mL to about 1000 μg/mL.
45. The therapeutic composition of any one of embodiments 24 to 44, wherein the purity of the rAAV is more than about 90% v/v.
46. The therapeutic composition of embodiment 45, wherein the therapeutic composition does not comprise any single impurity greater than about 5% v/v.
47. The therapeutic composition of any one of embodiments 24 to 46, wherein the therapeutic composition comprises from about 0.0007% to about 0.0012% of Pluronic.
48. The therapeutic composition of any one of embodiments 24 to 47, wherein the therapeutic composition comprises less than about 5.5×104 copies RNA/mL of Rhabdovirus.
49. The therapeutic composition of any one of embodiments 24 to 48, wherein the extractable volume of the therapeutic composition in the container is equal to or greater than about 1.0 mL.

TABLE 34

| Sequence Table | |
|---|---|
| GCase amino acid sequence | MEFSSPSREECPKPLSRVSIMAGSLTGLLLLQAVSWASGARPCIPKSFGYSSVVCVCN<br>ATYCDSFDPPTFPALGTFSRYESTRSGRRMELSMGPIQANHTGTGLLLTLQPEQKFQK<br>VKGFGGAMTDAAALNILALSPPAQNLLLKSYFSEEGIGYNIIRVPMASCDFSIRTYTY<br>ADTPDDFQLHNFSLPEEDTKLKIPLIHRALQLAQRPVSLLASPWTSPTWLKTNGAVNG<br>KGSLKGQPGDIYHQTWARYFVKFLDAYAEHKLQFWAVTAENEPSAGLLSGYPFQCLGF<br>TPEHQRDFIARDLGPTLANSTHHNVRLLMLDDQRLLLPHWAKVVLTDPEAAKYVHGIA<br>VHWYLDFLAPAKATLGETHRLFPNTMLFASEACVGSKFWEQSVRLGSWDRGMQYSHSI<br>ITNLLYHVVGWTDWNLALNPEGGPNWVRNFVDSPIIVDITKDTFYKQPMFYHLGHFSK<br>FIPEGSQRVGLVASQKNDLDAVALMHPDGSAVVVVLNRSSKDVPLTIKDPAVGFLETI<br>SPGYSIHTYLWRRQ<br>(SEQ ID NO: 1) |
| Codon-optimized nucleotide sequence encoding GCase | atggaattcagcagccccagcagagaggaatgccccaagcctctgagccgggtgtcaa<br>tcatggccggatctctgacaggactgctgctgcttcaggccgtgtcttgggcttctgg<br>cgctagaccttgcatccccaagagcttcggctacagcagcgtcgtgtgcgtgtgcaat<br>gccacctactgcgacagcttcgaccctcctacctttcctgctctgggcaccttcagca<br>gatacgagagcaccagatccggcagacggatggaactgagcatgggacccatccaggc<br>caatcacacaggcactggcctgctgctgacactgcagcctgagcagaaattccagaaa<br>gtgaaaggcttcggcggagccatgacagatgccgccgctctgaatatcctggctctgt<br>ctccaccagctcagaacctgctgctcaagagctacttcagcgaggaaggcatcggcta<br>caacatcatcagagtgcccatggccagctgcgacttcagcatcaggacctacacctac<br>gccgacacacccgacgatttccagctgcacaacttcagcctgcctgaagaggacacca<br>agctgaagatccctctgatccacagagccctgcagctggcacaaagacccgtgtcact<br>gctggcctctccatggacatctcccacctggctgaaaacaaatggcgccgtgaatggc<br>aagggcagcctgaaaggccaacctggcgacatctaccaccagacctgggccagatact<br>tcgtgaagttcctggacgcctatgccgagcacaagctgcagttttgggccgtgacagc<br>cgagaacgaaccttctgctggactgctgagcggctacccctttcagtgcctgggcttt<br>acacccgagcaccagcgggactttatcgcccgtgatctgggacccacactggccaata<br>gcacccaccataatgtgcggctgctgatgctggacgaccagagactgcttctgcccca<br>ctgggctaaagtggtgctgacagatcctgaggccgccaaatacgtgcacggaatcgcc<br>gtgcactggtatctggactttctggcccctgccaaggccacactgggagagacacaca<br>gactgttccccaacaccatgctgttcgccagcgaagcctgtgtgggcagcaagttttg<br>ggaacagagcgtgcggctcggcagctgggatagaggcatgcagtacagccacagcatc<br>atcaccaacctgctgtaccacgtcgtcggctggaccgactggaatctggccctgaatc<br>ctgaaggcggccctaactgggtccgaaacttcgtggacagccccatcatcgtggacat<br>caccaaggacaccttctacaagcagcccatgttctaccacctgggacacttcagcaag<br>ttcatccccgagggctctcagcgcgttggactggtggcttcccagaagaacgatctgg<br>acgccgtggctctgatgcaccctgatggatctgctgtggtggtggtcctgaaccgcag<br>cagcaaagatgtgcccctgaccatcaaggatcccgccgtgggattcctggaaacaatc<br>agccctggctactccatccacacctacctgtggcgtagacag<br>(SEQ ID NO: 2) |
| Progranulin amino acid sequence | MWTLVSWVALTAGLVAGTRCPDGQFCPVACCLDPGGASYSCCRPLLDKWPTTLSRHLG<br>GPCQVDAHCSAGHSCIFTVSGTSSCCPFPEAVACGDGHHCCPRGEHCSADGRSCFQRS<br>GNNSVGAIQCPDSQFECPDFSTCCVMVDGSWGCCPMPQASCCEDRVHCCPHGAFCDLV<br>HTRCITPTGTHPLAKKLPAQRTNRAVALSSSVMCPDARSRCPDGSTCCELPSGKYGCC<br>PMPNATCCSDHLHCCPQDTVCDLIQSKCLSKENATTDLLTKLPAHTVGDVKCDMEVSC<br>PDGYTCCRLQSGAWGCCPFTQAVCCEDHIHCCPAGETCDTQKGTCEQGPHQVPWMEKA<br>PAHLSLPDPQALKRDVPCDNVSSCPSSDTCCQLTSGEWGCCPIPEAVCCSDHQHCCPQ<br>GYTCVAEGQCQRGSEIVAGLEKMPARRASLSHPRDIGCDQHTSCPVGQTCCPSLGGSW<br>ACCQLPHAVCCEDRQHCCPAGYTCNVKARSCEKEVVSAQPATFLARSPHVGVKDVECG<br>EGHFCHDNQTCCRDNRQGWACCPYRQGVCCADRRHCCPAGERCAARGTKCLRREAPRW<br>DAPLRDPALRQLL<br>(SEQ ID NO: 3) |

TABLE 34-continued

| Sequence Table | |
|---|---|
| Codon-optimized nucleotide sequence encoding Progranulin | atgtggaccctggtgagctgggtggccctgaccgccggcctggtggccggcacccgct<br>gccccgacggccagttctgccccgtggcctgctgcctggaccccggcggcgccagcta<br>cagctgctgccgccccctgctggacaagtggcccaccaccctgagccgccacctgggc<br>ggcccctgccaggtggacgcccactgcagcgccggccacagctgcatcttcaccgtga<br>gcggcaccagcagctgctgccccttccccgaggccgtggcctgcggcgacggccacca<br>ctgctgcccccgcggcttccactgcagcgccgacggccgcagctgcttccagcgcagc<br>ggcaacaacagcgtgggcgccatccagtgccccgacagccagttcgagtgccccgact<br>tcagcacctgctgcgtgatggtggacggcagctggggctgctgccccatgccccaggc<br>cagctgctgcgaggaccgcgtgcactgctgccccccacggcgccttctgcgacctggtg<br>cacacccgctgcatcacccccaccggcacccaccccctggccaagaagctgcccgccc<br>agcgcaccaaccgcgccgtggccctgagcagcagcgtgatgtgccccgacgcccgcag<br>ccgctgccccgacggcagcacctgctgcgagctgcccagcggcaagtacggctgctgc<br>cccatgcccaacgccacctgctgcagcgaccacctgcactgctgcccccaggacaccg<br>tgtgcgacctgatccagagcaagtgcctgagcaaggagaacgccaccaccgacctgct<br>gaccaagctgcccgcccacaccgtgggcgacgtgaagtgcgacatggaggtgagctgc<br>cccgacggctacacctgctgccgcctgcagagcggcgcctggggctgctgccccttca<br>cccaggccgtgtgctgcgaggaccacatccactgctgccccgccggcttcacctgcga<br>cacccagaagggcacctgcgagcagggcccccaccaggtgccctggatggagaaggcc<br>cccgcccacctgagcctgcccgacccccaggccctgaagcgcgacgtgccctgcgaca<br>acgtgagcagctgccccagcagcgacacctgctgccagctgaccagcggcgagtgggg<br>ctgctgccccatccccgaggccgtgtgctgcagcgaccaccagcactgctgcccccag<br>ggctacacctgcgtggccgagggccagtgccagcgcggcagcgagatcgtggccggcc<br>tggagaagatgcccgcccgccgcgccagcctgagccacccccgcgacatcggctgcga<br>ccagcacaccagctgccccgtgggccagacctgctgccccagcctgggcggcagctgg<br>gcctgctgccagctgccccacgccgtgtgctgcgaggaccgccagcactgctgccccg<br>ccggctacacctgcaacgtgaaggcccgcagctgcgagaaggaggtggtgagcgccca<br>gcccgccaccttcctggcccgcagcccccacgtgggcgtgaaggacgtggagtgcggc<br>gagggccacttctgccacgacaaccagacctgctgccgcgacaaccgccagggctggg<br>cctgctgcccctaccgccagggcgtgtgctgcgccgaccgccgccactgctgccccgc<br>cggcttccgctgcgccgcccgcggcaccaagtgcctgcgccgcgaggcccccgctgg<br>gacgccccctgcgcgaccccgccctgcgccagctgctg<br>(SEQ ID NO: 4) |
| Wild-type AAV2 ITR | aggaacccctagtgatggagttggccactccctctctgcgcgctcgctcgctcactga<br>ggccgggcgaccaaaggtcgcccgacgcccgggctttgcccgggcggcctcagtgagc<br>gagcgagcgcgcagagagggagtggccaa<br>(SEQ ID NO: 5) |
| Nucleotide sequence encoding inhibitory nucleic acid targeting α-synuclein | tggaagacttcgagatacactgt<br>(SEQ ID NO: 12) |

What is claimed is:

1. A therapeutic composition comprising recombinant adeno-associated virus (rAAV) particles, wherein the rAAV particles comprise an adeno-associated virus 9 (AAV9) capsid protein and an expression cassette encoding a gene product of interest, wherein the therapeutic composition comprises more than 1E+13 viral genomes per milliliter (vg/mL) rAAV particles, wherein the therapeutic composition comprises less than 15% empty rAAV particles and at least 80% full rAAV particles, wherein the gene product of interest is human glucocerebrosidase (GCase), and the expression cassette comprises the nucleotide sequence of SEQ ID NO: 2, wherein the therapeutic composition is produced by infecting Sf9 insect cells with a population of Baculovirus vectors and lysing the insect cells to produce a cellular lysate comprising the rAAV particles, wherein the cellular lysate is subjected to a method comprising the steps of:

(i) contacting an affinity chromatography column with the cellular lysate, wherein the affinity column comprises a binding agent specific for a capsid protein of the rAAV particles under conditions under which the rAAV particles bind to the affinity chromatography column;

(ii) eluting the bound rAAV particles from the column thereby producing a first eluate;

(iii) performing anion-exchange chromatography on the first eluate to produce a second eluate, wherein the second eluate comprises fewer empty rAAV particles than the first eluate; and (iv) concentrating the second eluate by performing tangential flow filtration using a flow buffer comprising Tris, $MgCl_2$, NaCl, and Poloxamer 188, thereby producing the therapeutic composition comprising rAAV particles, and wherein the therapeutic composition comprises less than or equal to 1.3 ng residual host cell DNA from the insect cells per 1E+14 vg/ml of the rAAV particles of the therapeutic composition.

2. The therapeutic composition of claim 1, wherein the therapeutic composition comprises from about 1E+13 vg/mL to about 1E+14 vg/mL.

3. The therapeutic composition of claim 1, wherein the therapeutic composition is in a container.

4. The therapeutic composition of claim 3, wherein the therapeutic composition comprises less than 6000 particles that are larger than 10 μm per container, and less than 600 particles that are larger than 25 μm per container.

5. The therapeutic composition of claim 3, wherein the therapeutic composition in the container has an extractable volume equal to or greater than 1.0 mL.

6. The therapeutic composition of claim 1, wherein the therapeutic composition is sterile.

7. The therapeutic composition of claim 1, wherein the therapeutic composition does not promote microbial growth.

8. The therapeutic composition of claim 1, wherein the therapeutic composition comprises an endotoxin level less than 0.5 endotoxin units per milliliter (EU/mL).

9. The therapeutic composition of claim 1, wherein more than 1.0E+13 vg/mL of the therapeutic composition comprises the gene product.

10. The therapeutic composition of claim 1, wherein the therapeutic composition has a 50% cell culture infectious dose (TCID50) titer from about 1,000 viral genomes per infectious unit (vg/IU) to about 6,000 vg/IU or from about 4,500 vg/IU to about 10,000 vg/IU.

11. The therapeutic composition of claim 1, wherein activity of the human GCase is at least 110% relative to a reference standard, wherein the reference standard is a purified rAAV encoding GCase.

12. The therapeutic composition of claim 1, wherein the therapeutic composition has an infectious titer from about 8.0E+9 infectious unit per milliliter (IU/mL) to about 1.2E+10 IU/mL.

13. The therapeutic composition of claim 1, wherein the therapeutic composition has an osmolality between about 300 mOsm/kg and about 500 mOsm/kg.

14. The therapeutic composition of claim 1, wherein the therapeutic composition has a pH between about 7 and about 9.

15. The therapeutic composition of claim 1, wherein the therapeutic composition is free from visible particulate matter.

16. The therapeutic composition of claim 1, wherein the therapeutic composition comprises less than or equal to 3% aggregates.

17. The therapeutic composition of claim 1, wherein the therapeutic composition comprises a total protein level from about 300 μg/mL to about 1000 μg/mL.

18. The therapeutic composition of claim 1, wherein the therapeutic composition has a purity of more than 90% v/v.

19. The therapeutic composition of claim 18, wherein the therapeutic composition does not comprise any single impurity greater than about 5% v/v.

20. The therapeutic composition of claim 1, wherein the therapeutic composition comprises from about 0.0007% to about 0.0012% of Poloxamer 188.

21. The therapeutic composition of claim 1, wherein the therapeutic composition comprises less than 5.5×104 copies of Rhabdovirus RNA per mL of the therapeutic composition.

22. The therapeutic composition of claim 1, wherein the therapeutic composition comprises less than or equal to 45 ng residual host cell protein from the insect cells per 1E+13 viral genomes (vg) of the rAAV particles.

* * * * *